United States Patent [19]

Uchida et al.

[11] 4,372,953

[45] Feb. 8, 1983

[54] TETRAZOLE DERIVATIVES, AND ANTI-ULCER COMPOSITION CONTAINING THE SAME

[75] Inventors: Minoru Uchida, Komatsujima; Takao Nishi; Kazuyuki Nakagawa, both of Tokushima, all of Japan

[73] Assignee: Otsuka Pharmaceutical Company, Limited, Tokyo, Japan

[21] Appl. No.: 239,044

[22] Filed: Feb. 27, 1981

[30] Foreign Application Priority Data

| Feb. 29, 1980 | [JP] | Japan | 55-25521 |
| Mar. 1, 1980 | [JP] | Japan | 55-25707 |
| Mar. 1, 1980 | [JP] | Japan | 55-25708 |
| Mar. 3, 1980 | [JP] | Japan | 55-27084 |
| Sep. 16, 1980 | [JP] | Japan | 55-128160 |
| Sep. 30, 1980 | [JP] | Japan | 55-136902 |
| Oct. 6, 1980 | [JP] | Japan | 55-140051 |

[51] Int. Cl.$^3$ ............ A61K 31/41; A61K 31/44; A61K 31/445; A61K 31/505; C07D 257/04; C07D 401/12; C07D 401/14; C07D 401/06
[52] U.S. Cl. ............ 424/248.5; 546/209; 424/248.51; 546/210; 546/212; 424/248.52; 546/256; 546/172; 424/248.56; 546/176; 546/284; 424/248.57; 546/276; 548/202; 424/251; 548/203; 548/214; 424/258; 548/252; 548/253; 424/272; 548/136; 548/143; 424/273 R; 548/204; 548/205; 424/273 B; 548/254; 548/250; 424/263; 548/251; 424/270; 424/269; 544/132; 544/124; 544/131; 544/122; 544/128; 544/134; 544/138; 544/133; 544/119; 544/357; 544/360; 544/363; 544/366; 544/367; 544/333; 260/243.3; 260/245.5 ; 546/193; 546/201; 546/208

[58] Field of Search ............ 424/263, 270, 269, 248.5, 424/51, 52, 56, 57, 251, 258, 272, 273 R; 546/276, 193, 201, 208, 256, 209, 210, 212, 172, 176, 284; 548/252, 136, 143, 204, 253, 205, 254, 250, 202, 251, 203, 214; 260/243.3, 245.5; 544/132, 124, 131, 122, 128, 134, 138, 133, 119, 357, 360, 363, 366, 367, 333

[56] References Cited

U.S. PATENT DOCUMENTS

| 2,507,337 | 5/1950 | Harvill et al. | 260/308 |
| 3,578,674 | 5/1971 | Buckler | 548/253 |
| 3,743,646 | 7/1973 | Buckler et al. | 548/253 |
| 3,767,667 | 10/1973 | Wehrli | 260/340.9 |
| 4,110,338 | 8/1978 | Kamiya | 260/308 D |

OTHER PUBLICATIONS

LaForge et al., *J. Org. Chem.*, vol. 21, pp. 767–771 (1956).

*Primary Examiner*—John M. Ford
*Attorney, Agent, or Firm*—Wegner & Bretschneider

[57] ABSTRACT

Tetrazole derivatives of the formula:

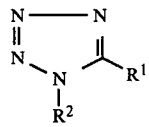

(1)

wherein $R^1$ is a lower alkykl, phenyl or a group of the formula: $-S(O)_l-A-(X)_m-R^3$, and $R^2$ is hydrogen, a lower alkyl, phenyl or a cycloalkyl when $R^1$ is the group $-S(O)_l-A-(X)_m-R^3$, or $R^2$ is a group of the formula: $-B-CO-R^4$ when $R^1$ is a lower alkyl or phenyl and a pharmaceutically acceptable salt thereof, which have prophylactic or therapeutic activities against peptic and/or duodenal ulcers and are useful as an anti-ulcer drug; processes for the preparation of the tetrazole derivatives; and pharmaceutical composition containing said tetrazole derivatives.

24 Claims, No Drawings

TETRAZOLE DERIVATIVES, AND ANTI-ULCER COMPOSITION CONTAINING THE SAME

The present invention relates to novel tetrazole derivatives, process for the preparation thereof and a pharmaceutical composition for treating peptic and duodenal ulcers which contains as the essential ingredient the tetrazole derivatives.

The compounds of the present invention are tetrazole derivatives of the formula:

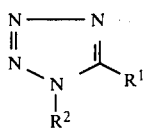  (1)

wherein $R^1$ is a lower alkyl, phenyl or a group of the formula: $-S(O)_l-A-(X)_m-R^3$, and $R^2$ is hydrogen, a lower alkyl, phenyl or a cycloalkyl when $R^1$ is the group $-S(O)_l-A-(X)_m-R^3$, or $R^2$ is a group of the formula: $-B-CO-R^4$ when $R^1$ is a lower alkyl or phenyl; in said formula $-S(O)_l-A-(X)_m-R^3$, X is $-CO-$ or $S-(O)_n-$, l and n are each 0, 1 or 2, m is 0 or 1, A is an alkylene having 1 to 8 carbon atoms, and $R^3$ is a lower alkyl, a cycloalkyl, naphthyl, a group of the formula:

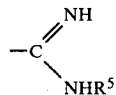

($R^5$ is a lower alkyl), a phenyl(lower)alkyl which may have a halogen substituent on the phenyl ring, a phenyl which may have 1 to 3 substituents selected from the group consisting of a halogen, a lower alkyl, a lower alkoxy, a lower alkanoylamino, hydroxy, carboxy and amino, a heterocyclic group-substituted lower alkyl which may have a substituent selected from a lower alkyl and amino wherein the heterocyclic group is selected from pyridyl, furyl and thiazolyl, or a heterocyclic group containing 1 to 4 hetero atoms selected from nitrogen, oxygen and sulfur which may have 1 to 2 substituents selected from the group consisting of a lower alkyl, a halogen, carboxy, oxo, amino, a lower alkoxycarbonyl, a lower alkoxy, hydroxy, nitro, phenyl, a cycloalkyl and a lower alkylamino, and when m is 0, $R^3$ may also be a group of the formula: $-NR^6R^7$ wherein $R^6$ is hydrogen, a lower alkyl or a phenyl(lower)alkyl, and $R^7$ is hydrogen, a lower alkyl, a group $-CZ-NHR^8$ (Z is sulfur or an imino which may be substituted with a lower alkyl, and $R^8$ is a lower alkyl or amino), a tetrazolyl which may have a lower alkyl substituent, or a group $-CO-R^9$ ($R^9$ is a lower alkyl, a phenyl which may have 1 to 3 lower alkoxy substituents, a cycloalkyl or a 5- or 6-membered unsaturated heterocyclic group containing one hetero atom selected from nitrogen and oxygen), or the $R^6$ and $R^7$ may combine together with the nitrogen atom to which they are joined to form a group

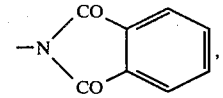

in said formula $-B-CO-R^4$, B is a lower alkylene, and $R^4$ is hydroxy, a lower alkoxy or a group of the formula: $-NR^{10}R^{11}$ wherein $R^{10}$ and $R^{11}$ are the same or different and are each hydrogen, a lower alkyl (which may have a substituent selected from the group consisting of hydroxy, furyl, pyridyl, phenyl and a phenyl having 1 to 2 lower alkoxy substituents), a cycloalkyl (which may have a substituent selected from the group consisting of hydroxy or a lower alkoxy), a phenyl (which may have 1 to 2 substituents selected from the group consisting of a lower alkyl, a lower alkoxy, a halogen, nitro, carboxy and a lower alkylamino), or a thiazolyl, or the $R^{10}$ and $R^{11}$ may combine together with the nitrogen atom to which they are joined with or without being intervened with nitrogen or oxygen to form a 5- or 6-membered saturated heterocyclic group which may have a lower alkyl substituent, provided that when m is 0, $R^3$ is not unsubstituted phenyl(lower)alkyl or unsubstituted phenyl, and a pharmaceutically acceptable salt thereof.

The compounds of the present invention have prophylactic or therapeutic activities against peptic and/or duodenal ulcers and are useful as a medicine for treating peptic and/or duodenal ulcers in human and other animals.

In the present specification, the term "lower alkyl" denotes a straight or branched alkyl group having 1 to 6 carbon atoms and includes, for example, methyl, ethyl, propyl, isopropyl, butyl, tert-butyl, pentyl, and hexyl. The term "cycloalkyl" denotes a cycloalkyl having 3 to 8 carbon atoms and includes, for example, cyclopropyl, cyclobutyl, cyclopentyl, cyclohexyl, cycloheptyl, and cyclooctyl. The term "lower alkoxy" denotes an alkoxy having 1 to 6 carbon atoms and includes, for example, methoxy, ethoxy, propoxy, isopropoxy, butoxy, tert-butoxy, pentyloxy, and hexyloxy. The term "lower alkylene" denotes an alkylene having 1 to 6 carbon atoms and includes, for example, methylene, ethylene, trimethylene, 2-methyltrimethylene, 2,2-dimethyltrimethylene, 1-methyltrimethylene, tetramethylene, pentamethylene, and hexamethylene. The term "alkylene having 1 to 8 carbon atoms" includes heptamethylene, 4-methylheptamethylene and octamethylene in addition to the above lower alkylene. The term "halogen" denotes fluorine, chlorine, bromine and iodine. The term "lower alkanoylamino" denotes an alkanoylamino having 1 to 6 carbon atoms in the alkanoyl moiety and includes, for example, formamido, acetamido, propionamido, butyramido, isobutyramido, pentyramido, and hexyramido. The term "lower alkoxycarbonyl" denotes an alkoxycarbonyl having 1 to 6 carbon atoms in the alkoxy moiety and includes, for example, methoxycarbonyl, ethoxycarbonyl, propoxycarbonyl, isopropoxycarbonyl, butoxycarbonyl, tert-butoxycarbonyl, pentyloxycarbonyl, and hexyloxycarbonyl. The term "lower alkylamino" denotes a monoalkyl- or dialkylamino having 1 to 6 carbon atoms in the alkyl moiety and includes, for example, methylamino, ethylamino, propylamino, isopropylamino, butylamino, tert-butylamino, pentylamino, hexylamino, dimethylamino, diethylamino, methylethylamino, dibutylamino, and dihexylamino.

The "phenyl(lower)alkyl" includes benzyl, 2-phenylethyl, 1-phenylethyl, 3-phenylpropyl, 4-phenylbutyl, 1,1-dimethyl-2-phenylethyl, 5-phenylpentyl, 6-phenylhexyl, and 2-methyl-3-phenylpropyl. The "phenyl(lower)alkyl having a halogen substituent on the phenyl ring" includes 4-chlorobenzyl, 3-bromobenzyl, 2-fluorobenzyl, 2-(2-bromophenyl)ethyl, 2-(3-chlorophenyl)ethyl, 2-(4-iodophenyl)ethyl, 1-(2-iodophenyl)ethyl, 1-(3-chlorophenyl)ethyl, 1-(4-bromophenyl)ethyl, 3-(2-fluorophenyl)propyl, 3-(3-chlorophenyl)propyl, 3-(4-bromophenyl)propyl, 4-(2-chlorophenyl)butyl, 4-(3-bromophenyl)butyl, 4-(4-iodophenyl)butyl, 1,1-dimethyl-2-(4-chlorophenyl)ethyl, 5-(4-bromophenyl)pentyl, 5-(2-chlorophenyl)pentyl, 5-(3-fluorophenyl)pentyl, 6-(2-chlorophenyl)hexyl, 6-(3-iodophenyl)hexyl, 6-(4-bromophenyl)hexyl, and 2-methyl-3-(4-chlorophenyl)propyl. The "lower alkyl having a substituent selected from the group consisting of hydroxy, furyl, pyridyl, phenyl and a phenyl having 1 to 2 lower alkoxy substituents" includes hydroxymethyl, 3-hydroxypropyl, 5-hydroxypentyl, 2-phenylethyl, 3-phenylpropyl, 4-methoxybenzyl, 2-(3,4-diethoxyphenyl)ethyl, 4-(3-ethoxyphenyl)butyl, 2-(2-furyl)ethyl, 3-(2-furyl)propyl, 2-(3-furyl)ethyl, 5-(2-furyl)pentyl, 2-(2-pyridyl)ethyl, 2-(3-pyridyl)ethyl, 3-(3-pyridyl)propyl, 4-(2-pyridyl)butyl, and 6-(2-pyridyl)hexyl. The "cycloalkyl having a substituent selected from hydroxy and a lower alkoxy" includes 2-methoxycyclopropyl, 2-ethoxycyclopropyl, 3-methoxycyclobutyl, 2-methoxycyclopentyl, 2-methoxycyclohexyl, 4-methoxycyclohexyl, 2-ethoxycyclohexyl, 4-butoxycyclohexyl, 5-methoxycyclooctyl, 2-hydroxycyclopropyl, 3-hydroxycyclobutyl, 2-hydroxycyclohexyl, 3-hydroxycyclohexyl, 4-hydroxycyclohexyl, and 5-hydroxycyclooctyl. The "imino which may be substituted with a lower alkyl" includes imino, methylimino, ethylimino, propylimino, isopropylimino, butylimino, pentylimino and hexylimino.

The "phenyl which may have 1 to 3 substituents selected from the group consisting of a halogen, a lower alkyl, a lower alkoxy, a lower alkanoylamino, hydroxy, carboxy and amino" includes phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 3,4,5-trimethoxyphenyl, 2,5-dimethoxyphenyl, 2-acetamidophenyl, 3-acetamidophenyl, 4-acetamidophenyl, 4-formamidophenyl, 2-propionamidophenyl, 3-butyramidophenyl, 4-hexyramidophenyl, 3,4-diacetamidophenyl, 2-hydroxyphenyl, 3-hydroxyphenyl, 4-hydroxyphenyl, 3,4-dihydroxyphenyl, 3,4,5-trihydroxyphenyl, 2-carboxyphenyl, 3-carboxyphenyl, 4-carboxyphenyl, 3,4-dicarboxyphenyl, 2-aminophenyl, 3-aminophenyl, 4-aminophenyl, 2,4-diaminophenyl, 3-methyl-4-chlorophenyl, 2-chloro-6-methylphenyl, 2-methoxy-3-chlorophenyl, and 3,5-di-tert-butyl-4-hydroxyphenyl. The "phenyl which may have 1 to 3 lower alkoxy substituents" includes the above-mentioned alkoxy-substituted phenyl group. The "phenyl which may have 1 to 2 substituents selected from the group consisting of a lower alkyl, a lower alkoxy, a halogen, nitro, carboxy and a lower alkylamino" includes 2-nitrophenyl, 3-nitrophenyl, 4-nitrophenyl, 2,4-dinitrophenyl, 2-(dimethylamino)phenyl, 3-(diethylamino)phenyl, 4-(methylethylamino)phenyl, 3,4-di(dimethylamino)phenyl, as well as the above-mentioned substituted phenyl groups.

The "heterocyclic group-substituted lower alkyl which may have a substituent selected from a lower alkyl and amino on the heterocyclic ring" as defined for the group $R^3$ includes 2-pyridylmethyl, 3-pyridylmethyl, 4-pyridylmethyl, 1-(2-pyridyl)ethyl, 2-(2-pyridyl)ethyl, 3-(4-pyridyl)propyl, 4-(2-pyridyl)butyl, 5-(3-pyridyl)pentyl, 6-(2-pyridyl)hexyl, 1,1-dimethyl-2-(2-pyridyl)ethyl, (2-methyl-6-pyridyl)methyl, (4-methyl-2-pyridyl)methyl, 2-furylmethyl, 3-furylmethyl, 1-(2-furyl)ethyl, 2-(2-furyl)ethyl, 5-(3-furyl)pentyl, 6-(2-furyl)hexyl, 4-(2-furyl)butyl, 3-(2-furyl)propyl, (5-methyl-2-furyl)methyl, (3-methyl-2-furyl)methyl, (2-methyl-3-furyl)methyl, 2-thiazolylmethyl, 4-thiazolylmethyl, (2-methyl-4-thiazolyl)methyl, 2-(2-ethyl-4-thiazolyl)ethyl, 3-(2-thiazolyl)propyl, 4-(2-methyl-5-thiazolyl)butyl, 6-(2-butyl-4-thiazolyl)hexyl, 1,1-dimethyl-2-(2-methyl-4-thiazolyl)ethyl, 2-amino-6-pyridylmethyl, 4-amino-2-pyridylmethyl, 2-(6-amino-2-pyridyl)ethyl, 5-amino-2-furylmethyl, 3-amino-2-furylmethyl, 4-(2-amino-3-furyl)propyl, 4-amino-2-thiazolylmethyl, 2-(2-amino-4-thiazolyl)ethyl, and 1,1-dimethyl-2-(2-methyl-4-thiazolyl)ethyl.

The "heterocyclic group containing 1 to 4 hetero atoms selected from nitrogen, oxygen and sulfur which may have 1 to 2 substituents selected from the group consisting of a lower alkyl, a halogen, carboxy, oxo, amino, a lower alkoxycarbonyl, a lower alkoxy, hydroxy, nitro, phenyl, a cycloalkyl and a lower alkylamino" as defined for the group $R^3$ includes, for example, heterocyclic groups such as thienyl, furyl, pyrrolyl, pyridyl, pyranyl, pyrimidyl, quinolyl, 1,2,3,4-tetrahydroquinolyl, imidazolyl, 1,3,4-thiadiazolyl, 1,3,4-oxadiazolyl, 1H-1,2,4-triazolyl, 4H-1,2,4-triazolyl, thiazolyl, 1,2,3,4-tetrazolyl, benzimidazolyl, quinazolyl, 2,4-dihydroquinazolyl, 3H,4H-1,3,4-benzotriazepinyl, and the heterocyclic groups having 1 to 2 substituents on the ring thereof. Suitable examples of these heterocyclic groups are 2-thienyl, 3-thienyl, 4-methyl-2-thienyl, 5-ethyl-2-thienyl, 5-hexyl-2-thienyl, 3-chloro-2-thienyl, 2-chloro-3-thienyl, 5-bromo-3-thienyl, 5-fluoro-2-thienyl, 4,5-diethyl-2-thienyl, 5-amino-2-thienyl, 4-nitro-2-thienyl, 5-carboxy-2-thienyl, 4-methoxy-2-thienyl, 2-furyl, 3-furyl, 4-methyl-2-furyl, 5-ethyl-2-furyl, 2,5-dimethyl-3-furyl, 4-ethoxy-2-furyl, 5-butoxy-2-furyl, 5-amino-2-furyl, 4-chloro-2-furyl, 5-bromo-3-furyl, 5-carboxy-2-furyl, 5-propoxycarbonyl-2-furyl, 2-pyrrolyl, 3-pyrrolyl, 4-methyl-2-pyrrolyl, 1-methyl-2-pyrrolyl, 5-tert-butyl-2-pyrrolyl, 5-chloro-2-pyrrolyl, 4-iodo-3-pyrrolyl, 2-pyridyl, 3-pyridyl, 4-pyridyl, 3-methyl-2-pyridyl, 3-hydroxy-2-pyridyl, 6-methoxy-2-pyridyl, 6-methyl-2-pyridyl, 2,3-dimethyl-6-pyridyl, 5-nitro-2-pyridyl, 5-chloro-2-pyridyl, 4-hydroxy-2-pyridyl, 6-ethyl-2-pyridyl, 5-hydroxy-2-pyridyl, 4-ethoxy-2-pyridyl, 5-hexyloxy-2-pyridyl, 6-phenyl-2-pyridyl, 3-nitro-2-pyridyl, 4-nitro-2-pyridyl, 4-bromo-2-pyridyl, 6-fluoro-2-pyridyl, 4-amino-2-pyridyl, 3-chloro-2-pyridyl, 3-carboxy-2-pyridyl, 6-carboxy-2-pyridyl, 2-pyranyl, 3-pyranyl, 4-pyranyl, 4-methyl-2-pyranyl, 2-pyrimidyl, 4-pyrimidyl, 5-pyrimidyl, 4-methyl-2-pyrimidyl, 5-hexyl-2-pyrimidyl, 6-propyl-2-pyrimidyl, 5-methyl-2-pyrimidyl, 4-pentyl-2-pyrimidyl, 2-amino-4-methyl-6-pyrimidyl, 4-hydroxy-2-pyrimidyl, 4-amino-2-pyrimidyl, 4-nitro-2-pyrimidyl, 4-carboxy-2-pyrimidyl, 4-methoxy-2-pyrimidyl, 2-quinolyl, 3-methyl-2-quinolyl, 4-methoxy-2-quinolyl, 5-nitro-2-quinolyl, 3-chloro-2-quinolyl, 3-hydroxy-2-quinolyl, 5-amino-2-quinolyl, 4-quinolyl, 2-hydroxy-5-quinolyl, 2-hydroxy-6-quinolyl, 2-hydroxy-7-quinolyl, 2-hydroxy-8-quinolyl, 2-methoxy-7-quinolyl, 2-imidazolyl, 4-imidazolyl, 1-methyl-2-imidazolyl, 4-chloro-2-imidazolyl, 5-methoxy-2-imidazolyl, 5-hydroxy-2-imidazolyl, 4-amino-2-imidazolyl, 1-nitro-2-imidazolyl, 4H-1,2,4-triazol-5-yl, 1H-1,2,4-triazol-5-yl, 4H-1,2,4-triazol-3-yl, 4-methyl-1,2,4-triazol-3-yl, 3,4-dimethyl-1,2,4-triazol-5-yl, 3-methoxy-1,2,4-triazol-5-yl, 3-amino-1,2,4-triazol-5-yl, 3-nitro-1,2,4-triazol-5-yl, 2-thiazolyl, 4-thiazolyl, 5-thiazolyl, 4-methyl-2-thiazolyl, 4-methoxy-2-thiazolyl, 2-amino-4-thiazolyl, 4-nitro-2-thiazolyl, 5-hydroxy-2-thiazolyl, 2-benzimidazolyl, 4-methyl-2-benzimidazolyl, 5-methoxy-2-benzimidazolyl, 6-amino-2-benzimidazolyl, 7-nitro-2-benzimidazolyl, 4-hydroxy-2-benzimidazolyl, 1,2,3,4-tetrazol-1-yl, 1,2,3,4-tetrazol-5-yl, 1-methyl-1,2,3,4-tetrazol-5-yl, 1-ethyl-1,2,3,4-tetrazol-5-yl, 1-prpopyl-1,2,3,4-tetrazol-5-yl, 1-butyl-1,2,3,4-tetrazol-5-yl, 1-pentyl-1,2,3,4-tetrazol-5-yl, 1-hexyl-1,2,3,4-tetrazol-5-yl, 1-cyclohexyl-1,2,3,4-tetrazol-5-yl, 1-cyclopropyl-1,2,3,4-tetrazol-5-yl, 1-cyclobutyl-1,2,3,4-tetrazol-5-yl, 1-cyclopentyl-1,2,3,4-tetrazol-5-yl, 1-cycloheptyl-1,2,3,4-tetrazol-5-yl, 1-cyclooctyl-1,2,3,4-tetrazol-5-yl, 1-phenyl-1,2,3,4-tetrazol-5-yl, 5-methyl-1,2,3,4-tetrazol-1-yl, 5-methylamino-1,2,3,4-tetrazol-1-yl, 5-butylamino-1,2,3,4-tetrazol-1-yl, 3,4-dihydroxyquinazolin-4-on-2-yl (4-hydroxyquinazolin-2-yl), quinazolin-2-yl, quinazolin-4-yl, 3-methyl-3,4-dihydroquinazolin-4-on-2-yl, 5-methyl-1,3,4-oxadiazol-2-yl, 5-amino-1,3,4-oxadiazol-2-yl, 5-methoxy-1,3,4-oxadiazol-2-yl, 5-nitro-1,3,4-oxadiazol-2-yl, 5-hydroxy-1,3,4-oxadiazol-2-yl, 5-chloro-1,3,4-oxadiazol-2-yl, 5-carboxy-1,3,4-oxadiazol-2-yl, 1,3,4-thiadiazol-2-yl, 5-amino-1,3,4-thiadiazol-2-yl, 5-methyl-1,3,4-thiadiazol-2-yl, 5-methoxy-1,3,4-thiadiazol-2-yl, 5-chloro-1,3,4-thiadiazol-2-yl, 5-hydroxy-1,3,4-thiadiazol-2-yl, 5-nitro-1,3,4-thiadiazol-2-yl, 3,4-dihydrocarbostyril-6-yl, 1-methyl-3,4-dihydrocarbostyril-6-yl, 1-propyl-3,4-dihydrocarbostyril-6-yl, 3H,4H-1,3,4-benzotriazepin-5-on-2-yl, and 3-methyl-3H,4H-1,3,4-benzotriazepin-5-on-2-yl.

The "tetrazolyl which may have a lower alkyl substituent" as defined for $R^7$ in the formula —$NR^6R^7$ includes, for example, 1,2,3,4-tetrazol-5-yl, 1-methyl-1,2,3,4-tetrazol-5-yl, 1-ethyl-1,2,3,4-tetrazol-5-yl, 1-propyl-1,2,3,4-tetrazol-5-yl, 1-butyl-1,2,3,4-tetrazol-5-yl, 1-pentyl-1,2,3,4-tetrazol-5-yl, and 1-hexyl-1,2,3,4-tetrazol-5-yl, The "5- or 6-membered unsaturated heteracyclic group containing one hetero atom selected from nitrogen and oxygen" as defined for $R^9$ in the formula —CO—$R^9$ includes, for example, pyridyl, pyranyl, pyrrolyl and furyl, particularly 2-pyridyl, 3-pyridyl, 4-pyridyl, 2H-pyran-2-yl, 2H-pyran-3-yl, 4H-pyran-2-yl, 3,4-dihydro-2H-pyran-2-yl, 3,4-dihydro-2H-pyran-4-yl, 2-pyrrolyl, 3-pyrrolyl, 2-furyl and 3-furyl.

The "thiazolyl" as defined for $R^{10}$ and $R^{11}$ in the formula —$NR^{10}R^{11}$ includes 2-thiazolyl, 4-thiazolyl, and 5-thiazolyl.

The "5- or 6-membered saturated heterocyclic group which may have a lower alkyl substituent" which is formed by combining $R^{10}$ and $R^{11}$ together with the nitrogen atoms to which they are joined with or without being intervened with nitrogen or oxygen in the formula —$NR^{10}R^{11}$ includes, for example, pyrrolidino, morpholino, 1-piperidyl, 1-piperazinyl, 4-methyl-1-piperazinyl, 4-ethyl-1-piperazinyl, 4-propyl-1-piperazinyl, 4-tert-butyl-1-piperazinyl, and 4-hexyl-1-piperazinyl.

The compounds of the present invention can be prepared by various processes. For instance, the compounds of the formula [1] wherein $R^2$ is the group —B—CO—$R^4$ can be prepared by the following Reaction Scheme-I:

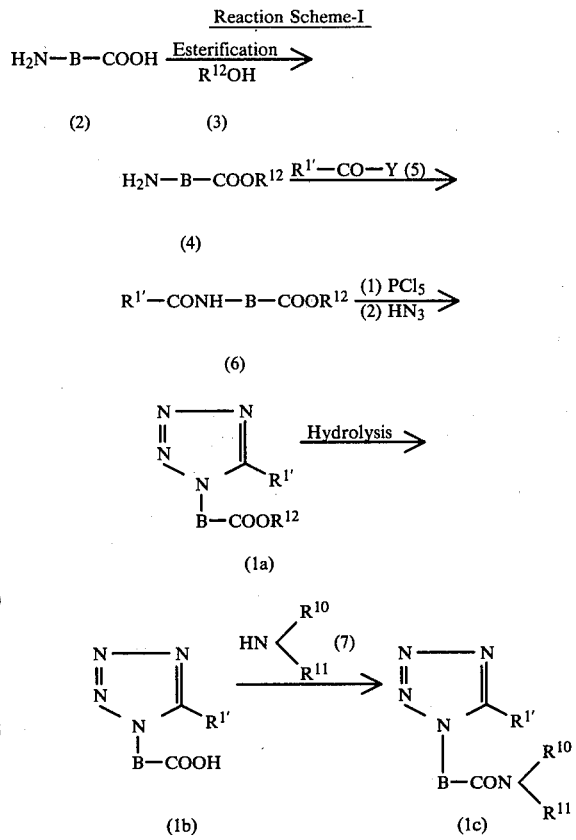

wherein $R^{10}$, $R^{11}$ and B are as defined above, $R^{1'}$ is a lower alkyl or phenyl, $R^{12}$ is a lower alkyl, and Y is a halogen.

In the above Reaction Scheme-I, the reaction of an aminocarboxylic acid (2) and a lower alcohol (3) can be carried out under the conditions which are generally used in the conventional esterification reaction, and is usually carried out in the presence of a catalyst. The catalyst may be anyone which is usually used in the conventional esterification reaction. Suitable examples of the catalyst are inorganic acids (e.g. hydrochloric acid gas, concentrated sulfuric acid, phosphoric acid, polyphosphoric acid, boron trifluoride, perchloric acid), organic acids (e.g. trifluoroacetic acid, trifluoromethanesulfonic acid, naphthalenesulfonic acid, p-toluenesulfonic acid, benzenesulfonic acid, ethanesulfonic acid), trifluoromethanesulfonic anhydride, thionyl chloride, acetone dimethyl acetal, or the like. Acidic ion exchange resins are also used as the catalyst. The amount of these catalysts is not critical, but may be in the range which is used in the conventional esterification reaction.

The above esterification reaction may be carried out in an appropriate solvent or without using any solvent. All solvents which are used in the conventional esterification reaction can be used. Suitable examples of the solvent are aromatic hydrocarbons (e.g. benzene, toluene, xylene), halogenated hydrocarbons (e.g. dichloromethane, dichloroethane, chloroform, carbon tetrachloride), ethers (e.g. diethyl ether, tetrahydrofuran, dioxane, ethylene glycol monomethyl ether), or the like.

The compound (2) and the compound (3) may be used in a wide range of ratio, but in order to obtain the desired compound in a high yield, the latter is used in a far excess amount to the former in case of using no solvent, and the latter is used in an amount of 1 to 5 moles, preferably 1 to 2 moles, to 1 mole of the former in case of using a solvent. The reaction is preferably carried out while removing the produced water from the reaction system by using an appropriate drier such as anhydrous calcium chloride, anhydrous copper sulfate, anhydrous calcium sulfate or phosphorus pentoxide in order to increase the yield of the product. The reaction temperature is not critical, but is preferably in the range of about $-20°$ to $200°$ C., more preferably about $0°$ to $150°$ C. The reaction period of time may vary with the kinds of the starting materials and reaction conditions, but the reaction is usually completed in about 10 minutes to 20 hours.

The aminocarboxylic acid ester (4) obtained in the above esterification reaction is then reacted with a carboxylic halide (5) in the presence of a dehydrohalogenating agent. As the dehydrohalogenating agent, basic compounds are usually used. Suitable examples of the basic compounds are inorganic bases such as sodium hydroxide, potassium hydroxide, sodium carbonate, potassium carbonate, sodium hydrogen carbonate, potassium hydrogen carbonate, or silver carbonate, alcoholates such as sodium methylate and sodium ethylate, and organic bases such as triethylamine, pyridine, N,N-dimethylaniline, N-methylmorpholine, 4-dimethylaminopyridine, 1,5-diazabicyclo[4.3.0]nonene-5 (DBN), 1,5-diazabicyclo[5.4.0]undecene-5 (DBU), 1,4-diazabicyclo[2.2.2]octane (DABCO). The aminocarboxylic acid ester (4) may be used as a solvent by using in an excess amount instead of using any specific solvent.

The above reaction may be carried out in an appropriate solvent or without using any solvent. All inert solvents which do not give undesirable effect on the reaction can be used. Suitable examples of the solvent are halogenated hydrocarbons (e.g. chloroform, methylene chloride, carbon tetrachloride), ethers (e.g. diethyl ether, tetrahydrofuran, dioxane), aromatic hydrocarbons (e.g. benzene, toluene, xylene), esters (e.g. methyl acetate, ethyl acetate), nonprotonic polar solvents (e.g. N,N-dimethylformamide, dimethyl sulfoxide, hexamethylphosphoric triamide), or the like.

The amount of the compound (4) and the compound (5) is not critical, but in case of using a solvent, the latter is usually used in at least equimolar amount, preferably 1 to 2 moles to 1 mole of the former. The reaction temperature and reaction period of time are not critical, but the reaction is usually carried out at a temperature of $-30°$ to $100°$ C., preferably $0°$ to $50°$ C., for 30 minutes to 12 hours.

The compound (6) thus obtained is reacted with $PCl_5$ in an appropriate solvent. All inert solvents which do not give undesirable effect on the reaction can be used. Suitable examples of the solvent are aromatic hydrocarbons (e.g. benzene, xylene, toluene), halogenated aromatic hydrocarbons (e.g. chlorobenzene, bromobenzene), ethers (e.g. diethyl ether, dioxane), aliphatic hydrocarbons (e.g. n-hexane, n-heptane), or the like. $PCl_5$ is usually used in an amount of about 1 to 2 moles, preferably 1 to 1.2 mole, to 1 mole of the compound (6). The reaction is usually carried out at a temperature of $-20°$ to $50°$ C., preferably $0°$ to $25°$ C., for a period about 30 minutes to 5 hours.

The resulting imine derivative is then reacted with $HN_3$ without being isolated from the reaction mixture, by which the desired compound (1a) is obtained. The hydrogen triazide ($HN_3$) is usually used in the form of a solution in benzene, xylene, diethyl ether or n-hexane. The amount of the imine derivative and $NH_3$ is usually in the range of that the latter is about 1 to 5 moles, preferably 1 to 3 moles, to 1 mole of the former. The reaction is carried out at a temperature of $0°$ to $150°$ C. for a period of 3 hours to 2 days.

The compound (1a) can be converted into another compound (1b) of the present invention by hydrolysis thereof. The hydrolysis is usually carried out in the presence of a catalyst. All catalyst which are usually used in the conventional hydrolysis can be used. Suitable examples of the catalyst are basic compounds such as sodium hydroxide, potassium hydroxide and barium hydroxide, and mineral acids such as sulfuric acid, hydrochloric acid and nitric acid. The amount of the catalyst is not critical. The hydrolysis is carried out in usual manner, preferably in an appropriate solvent, such as water or a lower alcohol (e.g. methanol, ethanol, isopropanol). The reaction temperature is not critical, either, but is usually in the range of from room temperature to about $150°$ C., preferably $50°$ to $110°$ C. The reaction is usually completed in a period of about 30 minutes to 10 hours.

The carboxylic acid derivative (1b) can be converted into another compound (1c) of the present invention by subjecting it to the conventional amido bond-forming reaction with an amine (7). In this reaction, a compound having an activated carboxyl group may be used instead of the compound (1b), and further, a compound having an activated amino group may be used instead of the amine (7).

The amido bond-forming reaction can be carried out under the conditions which are used in the conventional amido bond-forming reaction. For instance, it can be carried out by (i) a mixed anhydride method, i.e. a process comprising reacting the carboxylic acid (1b) with an alkyl halocarboxylate to give a mixed acid anhydride, and reacting the resulting mixed acid anhydride with the amine (7); (ii) an active ester method, i.e. a process comprising converting the carboxylic acid (1b) into an active ester, for example, p-nitrophenyl ester, N-hydroxysuccinimide ester, or 1-hydroxybenzotriazole ester, and then reacting the active ester with the amine (7); (iii) a carbodiimide method, i.e. a process comprising condensing the carboxylic acid (1b) with the amine (7) in the presence of a dehydrating agent such as dicyclohexylcarbodiimide or carbonyldiimidazole; (iv) a carboxylic acid halide method, i.e. a process comprising converting the carboxylic acid (1b) into a halide compound thereof, and reacting the halide compound with the amine (7); (v) another methods, for example, a process comprising converting the carboxylic acid (1b) into an acid anhydride compound thereof by treating it with a dehydrating agent such as acetic anhydride and then reacting the acid anhydride compound with the amine (7), or a process comprising converting the carboxylic acid (1b) into an ester with a lower alcohol and reacting the resulting ester with the amine (7) under a high pressure and at a high temperature. Among these processes, the mixed anhydride method and carboxylic acid halide method are preferable. The alkyl halocarboxylate used in the mixed anhydride method includes, for example, methyl chloroformate, methyl bromoformate, ethyl chloroformate, ethyl bromoformate, isobutyl chloroformate, and the like. The mixed acid anhydride may be prepared by the well-known Schotten-Baumann reaction and can be used in the subsequent reaction with the amine (7) without isolation from the reaction mixture to give the compound (1c) of the present invention. The Schotten-Baumann reaction is usually carried out in the presence of a basic compound. The basic compound includes all compounds which are usually used in Schotten-Baumann reaction, for example, organic bases such as triethylamine, trimethylamine, pyridine, dimethylaniline, N-methylmorpholine, 1,5-diazabicyclo[4.3.0]nonene-5 (DBN), 1,5-diazabicyclo[5.4.0]undecene-5 (DBU), 1,4-diazabicyclo[2.2.2]octane (DABCO), and inorganic bases such as potassium carbonate, sodium carbonate, potassium hydrogen carbonate, sodium hydrogen carbonate. The reaction is usually carried out at a temperature of $-20°$ to $100°$ C., preferably $0°$ to $50°$ C., for a period of about 5 minutes to 10 hours. The mixed anhydride method is usually carried out in an appropriate solvent. The solvent includes all solvents which are usually used in the conventional mixed anhydride method. Suitable examples of the solvent are halogenated hydrocarbons (e.g. methylene chloride, chloroform, dichloroethane), aromatic hydrocarbons (e.g. benzene, toluene, xylene), ethers (e.g. diethyl ether, tetrahydrofuran, dimethoxyethane), esters (e.g. methyl acetate, ethyl acetate), non-protonic polar solvents (e.g. dimethylformamide, dimethyl sulfoxide, hexamethylphosphoric triamide), or the like. The carboxylic acid (1b), the alkyl halocarboxylate and the amine (7) are usually used in equimolar amount, but the alkyl halocarboxylate and the amine (7) may be used in an amount of 1 to 1.5 mole to 1 mole of the carboxylic acid (1b).

The carboxylic acid halide method is carried out by reacting the carboxylic acid (1b) with a halogenating agent to obtain a halide compound of the carboxylic acid (1b) and then reacting the resulting carboxylic acid halide with the amine (7) after isolating and purifying the halide from the reaction mixture or without isolation to give the compound (1c) of the present invention.

The reaction of the carboxylic acid (1b) and the halogenating agent is carried out in the presence or absence of a solvent. The solvent includes all solvents which do not give undesirable effect on the reaction, for example, aromatic hydrocarbons (e.g. benzene, toluene, xylene), halogenated hydrocarbons (e.g. chloroform, methylene chloride, carbon tetrachloride), ethers (e.g. dioxane, tetrahydrofuran, diethyl ether), dimethylformamide, dimethyl sulfoxide, and the like. The halogenating agent includes any conventional halogenating agent which can convert the hydroxy group of the carboxyl group into halogen, for example, thionyl chloride, phosphorus oxychloride, phosphorus oxybromide, phosphorus pentachloride, phosphorus pentabromide, or the like.

The ratio of amount of the carboxylic acid (1b) and the halogenating agent is not critical, but when the reaction is carried out in the absence of a solvent, the latter is used in a largely excess amount, and when the reaction is carried out in the presence of a solvent, the latter is used in an equimolar amount or more, preferably 2 to 4 moles to 1 mole of the former. The reaction temperature and reaction period of time are not critical, either, but the reaction is usually carried out at a temperature of from room temperature to about $100°$ C., preferably $50°$ to $80°$ C., for a period of about 30 minutes to 6 hours.

The carboxylic acid halide thus obtained is reacted with the amine (7) under the same conditions as used in the reaction of the compounds (4) and the compound (5).

The compounds of the present invention can also be prepared by a process as shown in the following Reaction Scheme-II:

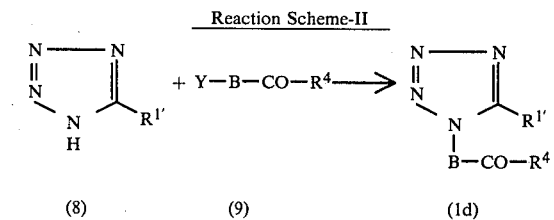

wherein $R^{1'}$, $R^4$, B and Y are as defined above.

The reaction of the compound (8) and the compound (9) in the above Reaction Scheme-II is carried out under the conditions which are usually used in the conventional dehydrohalogenation reaction. The reaction is preferably carried out by using a dehydrohalogenating agent in the presence of an alkali metal iodide such as sodium iodide or potassium iodide. The amount of the compound (9) is not critical, but is usually at least equimolar amount, preferably 1 to 2 moles to 1 mole of the compound (8).

The dehydrohalogenating agent used in the above reaction includes various basic compounds, for example, inorganic bases (e.g. sodium hydroxide, potassium hydroxide, sodium carbonate, potassium carbonate, sodium hydrogen carbonate, potassium hydrogen carbonate), alkali metals (e.g. sodium, potassium), organic bases such as tertiary amines (e.g. triethylamine, pyridine, N,N-dimethylaniline), or the like.

The reaction may be carried out in the presence or absence of a solvent. The solvent includes all solvents which do not give undesirable effect on the reaction, for example, lower alcohols (e.g. methanol, ethanol, propanol), ethers (e.g. diethyl ether, tetrahydrofuran, dioxane, ethylene glycol monomethyl ether), aromatic hydrocarbons (e.g. benzene, toluene, xylene), ketones (e.g. acetone, methyl ethyl ketone), dimethylformamide, dimethyl sulfoxide, hexamethylphosphoric triamide, or the like. The reaction is usually carried out at a temperature of from room temperature to $200°$ C., preferably $50°$ to $150°$ C., for a period of about 30 minutes to 6 hours.

The compounds of the formula (1) wherein $R^1$ is the group $-S(O)_l-A-(X)_m-R^3$ and $l$ is 0 can be prepared, for example, by a process as shown in the following Reaction Scheme-III:

Reaction Scheme-III

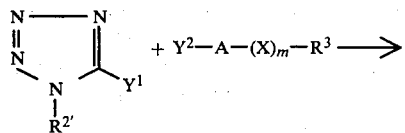

(10)    (11)

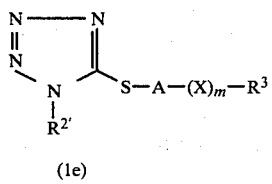

(1e)

wherein $R^3$, X, A and m are as defined above, and $R^{2'}$ is hydrogen, a lower alkyl, phenyl or a cycloalkyl, and either one of $Y^1$ and $Y^2$ is a halogen and another one is mercapto or amidinothio group.

The condensation reaction of the compound (10) and the compound (11) in the above Reaction Scheme-III is carried out under the same conditions as used in the reaction of the compound (8) and the compound (9) as in the above Reaction Scheme-II. When the starting compound (11) is a compound where the group —(X—)$_m$— is —CO—, the keto group may be protected with an appropriate keto-protecting group, and after the condensation reaction thereof with the compound (10), the keto-protecting group is removed by a conventional method. The keto-protecting group includes all groups which are stable under the conditions for the above condensation reaction, for example, lower alcohols (e.g. methanol, ethanol), lower alkylenediols (e.g. ethylene glycol, 1,3-trimethylenediol), lower alkanethiol (e.g. methanethiol, ethanethiol), lower alkylenedithiols (e.g. 1,2-ethylenedithiol, 1,3-trimethylenedithiol), or the like.

The removal of the keto-protecting group can be carried out by any conventional method. For example, the ketal group, which is formed with lower alcohols or lower alkylenediols, can easily be converted into the corresponding carbonyl group by contacting it with an acid catalyst, such as inorganic acids (e.g. hydrochloric acid, sulfuric acid, nitric acid, phosphoric acid perchloric acid) and organic acids (e.g. acetic acid, propionic acid, p-toluenesulfonic acid). The reaction is carried out in an appropriate solvent, such as alcohols (e.g. methanol, ethanol), ketones (e.g. acetone, methyl ethyl ketone), ethers (e.g. dioxane), non-protonic polar solvents (e.g. dimethyl sulfoxide, dimethylformamide), or the like. When an organic solvent is used, no more specific acid catalyst is required. The reaction is usually carried out at a temperature of from room temperature to 200° C., preferably 50° to 100° C., for about 30 minutes to 12 hours. Besides, when the keto group is protected in the form of a thioketal, which is formed by treating with lower alkanethiols or lower alkylenedithiols, the thioketal may be converted into the corresponding carbonyl group by a conventional method. For instance, the thioketal protecting group can easily be removed by treating it with mercuric chloride-mercury oxide, mercuric chloride-cadmium carbonate, silver nitrate-N-chlorosuccinimide, or the like. The removal of the protecting group can be carried out in an appropriate solvent such as water-soluble lower alcohols (e.g. methanol, ethanol), or a mixture of water and an organic solvent such as acetone, acetonitrile, or the like at a temperature of 0° to 100° C., preferably 50° to 80° C., for 1 to 5 hours.

The starting compounds (10) and (11) used in the above Reaction Scheme-III are partly known but include some novel compounds, which can be prepared by the processes as shown in the following Reaction Schemes-IV to VII.

Reaction Scheme-IV

$$R^3-Y^3 + Y^4-A-Y^2 \longrightarrow R^3-S-A-Y^2$$

(12)        (13)                    (11a)

Oxidation    Oxidation $$R^3-SO-A-Y^2 \xrightarrow{\text{Oxidation}} R^3-SO_2-A-Y^2$$

(11b)                    (11c)

wherein $R^3$, and A and $Y^2$ are as defined above, and either one of $Y^3$ and $Y^4$ is a halogen and another one is mercapto or amidinothio group.

The reaction of the compound (12) and the compound (13) in the Reaction Scheme-IV is carried out under the same conditions as used in the reaction of the compound (8) and the compound (9) in Reaction Scheme-II.

The oxidation reaction of the compound (11a) in order to convert it into the compound (11b) is usually carried out by using an oxidating agent in an appropriate solvent. The solvent may be any conventional solvents, for example, water, organic acids (e.g. formic acid, acetic acid, trifluoroacetic acid), alcohols (e.g. methanol, ethanol), halogenated hydrocarbons (e.g. chloroform, dichloromethane), or the like. The oxidating agent may also be any conventional agents which are effective to oxidize a mercapto group to a sulfoxide or sulfone group, for example, peracids (e.g. performic acid, peracetic acid, trifluoroperacetic acid, perbenzoic acid, m-chloroperbenzoic acid, o-carbonylperbenzoic acid), hydrogen peroxide, dichromic acid, dichromates (e.g. sodium dichromate, potassium dichromate), permanganic acid, permanganates (e.g. sodium permanganate, potassium permanganate), or the like. The oxidating agent is usually used in an amount of 1 mole or more, preferably 1 to 1.5 mole, to 1 mole of the compound (11a). The reaction is usually carried out at a temperature of 0° to 40° C., preferably at around room temperature, for about 20 to 50 hours.

The oxidation of the compound (11a) to convert into the corresponding sulfonic acid derivative (11c) is also carried out under the same conditions as used in the oxidation of the compound (11a) to the compound (11b), provided that the oxidating agent is used in an amount of 2 moles or more, preferably 2 to 4 moles, to 1 mole of the compound (11a) and the reaction time is in the range of about 3 to 8 hours.

The oxidation of the compound (11b) to convert into the compound (11c) is also carried out under the same conditions as used in the oxidation of the compound (11a) to the compound (11b).

Besides, the compounds in the above Reaction Scheme-IV wherein $Y^2$ is an amidinothio group may be prepared by reacting the corresponding halogenated compound with thiourea under the same conditions as used in the reaction of the compound (11d) or (11e) with urea as shown in Reaction Scheme-V hereinafter.

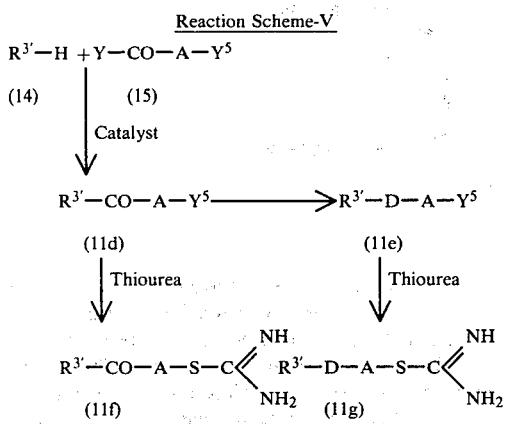

wherein A and Y are as defined above, and $R^{3'}$ is an aromatic group among the groups defined for $R^3$, $Y^5$ is a halogen, and D is a keto group protected with an appropriate keto-protecting group.

The reaction of the compound (14) and the compound (15) is carried out in an appropriate solvent under the conditions that the compound (14) is used in an equimolar or excess amount, preferably 1 to 3 moles to 1 mole of the compound (15), the reaction temperature is in the range of about 0° to 150° C., preferably 0° to room temperature, and the reaction period of time is in the range of about 1 to 5 hours. Suitable examples of the solvent are nitrobenzene, carbon disulfide, dichloromethane, carbon tetrachloride, 1,2-dichloroethane, or the like. The reaction is preferably carried out in the presence of a catalyst which is usually used in Friedel-Crafts reaction. Suitable examples of the catalyst are aluminum chloride, antimony pentachloride, ferric chloride, titanium tetrachloride, boron trifluoride, stannic chloride, zinc chloride, mercuric chloride, hydrogen fluoride, sulfuric acid, polyphosphoric acid, phosphorus pentachloride, or the like, among which aluminum chloride, stannic chloride and zinc chloride are particularly suitable. The catalyst is used in an equimolar or excess amount, preferably 1 to 3 moles to 1 mole of the compound (15).

The reaction of the compound (11d) or (11e) with thiourea is carried out in the presence or absence of a solvent. The solvent may be the same as used in the reaction of the compound (8) and the compound (9) in Reaction Scheme-II. The ratio of amount of the compound (11d) or (11e) and thiourea is not critical, but the latter is usually used in an amount of 1 to 5 moles, preferably 1 to 2 moles, to 1 mole of the former. The reaction temperature is not critical, either, but is usually in the range of from room temperature to 200° C., preferably 40° to 150° C. The reaction may also be carried out in the presence of a dehydrohalogenating agent as used in the reaction of the compounds (8) and (9) in Reaction Scheme-II.

The protection of keto group of the compound (11d) is done in the same manner as described in the above Reaction Scheme-III, that is, by treating the compound (11d) with an appropriate keto-protecting agent such as lower alcohols (e.g. methanol, ethanol), lower alkylenediols (e.g. ethylene glycol, 1,3-trimethylenediol), lower alkanethiols (e.g. methanethiol, ethanethiol), lower alkylenedithiols (e.g. 1,2-ethylenedithiol, 1,3-trimethylenedithiol) in an appropriate solvent or without using any solvent, under anhydrous condition, and in the presence of a catalyst. Suitable examples of the catalyst are sulfonic acids (e.g. ethanesulfonic acid, p-toluenesulfonic acid, benzenesulfonic acid), Lewis acids (e.g. zinc chloride, aluminum chloride, boron trifluoride), or the like. Suitable examples of the solvent are ethers (e.g. dioxane, tetrahydrofuran), aromatic hydrocarbons (e.g. benzene, toluene), halogenated hydrocarbons (e.g. chloroform, methyl chloride), or the like. The keto-protecting agent is used in an amount of at least equimolar to the compound (11d), usually in an excess amount. The reaction is usually carried out at a temperature of from 0° to 80° C., preferably from 0° to room temperature.

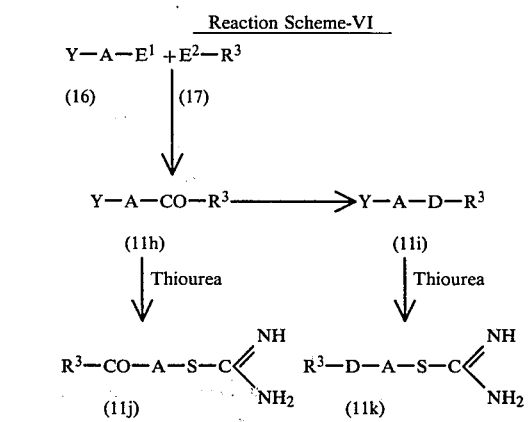

wherein A, D, Y and $R^3$ are as defined above, and either one of $E^1$ and $E^2$ is cyano and another one is the group $MgY^6$, and $Y^6$ is a halogen.

The reaction of the compound (16) and the compound (17) is carried out in an appropriate solvent at a temperature of from $-70°$ to $50°$ C., preferably $-30°$ to room temperature, for a period of about 1 to 6 hours. The solvent may be any inert solvents which are usually used in Grignard reaction, for example, ethers (e.g. diethyl ether, dioxane, tetrahydrofuran), aromatic hydrocarbons (e.g. benzene, toluene), saturated hydrocarbons (e.g. pentane, hexane, heptane, cyclohexane), or the like. The compound (17) is used in at least equimolar amount, preferably 1 to 1.5 mole to 1 mole of the compound (16). The reaction of the compound (11h) or (11i) and thiourea is carried out under the same conditions as used in the reaction of the compound (11d) or (11e) with thiourea in Reaction Scheme-V. Besides, the protection of keto group of the compound (11h) is also done in the same manner as in the protection of keto group of the compound (11d).

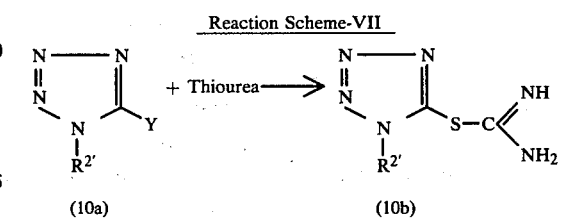

wherein $R^{2'}$ and Y are as defined above.

The reaction of the compound (10a) with thiourea is also carried out under the same conditions as used in the reaction of the compound (11d) or (11e) with thiourea in Reaction Scheme-V.

The compounds (1) of the present invention wherein the group $R^1$ is the group $-S-A-CO-R^3$ may also be prepared by processes as shown in the following Reaction Schemes-VIII to XII.

Reaction Scheme-VIII

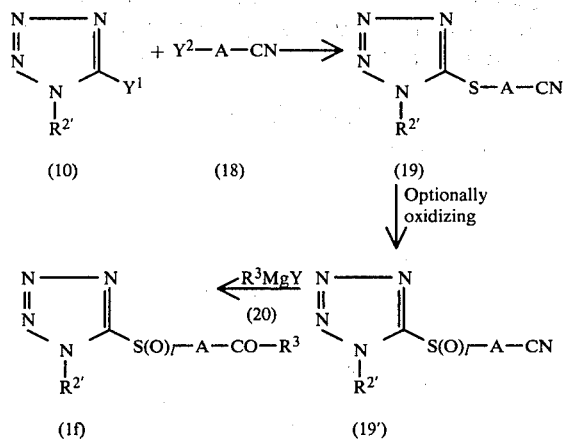

wherein $R^{2'}$, $R^3$, Y, $Y^1$, $Y^2$, A and l are as defined above.

The reaction of the tetrazole derivative (10) and the nitrile (18) is carried out under the same conditions as used in the reaction of the compounds (8) and (9) in Reaction Scheme-II. The oxidation of the compound (19) is also done in the same manner as in Reaction Scheme-IV. The reaction of the compound (19') and the Grignard reagent (20) is also carried out under the same conditions as used in the reaction of the compounds (16) and (17) in Reaction Scheme-VI. In this reaction, the reactive groups of the compound (19') and the Grignard reagent may be exchanged.

Reaction Scheme-IX

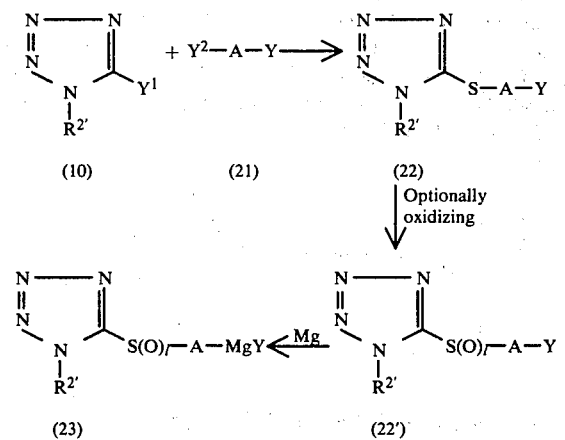

-continued
Reaction Scheme-IX

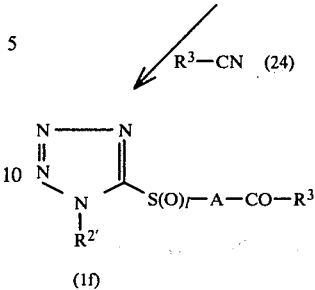

wherein $R^{2'}$, $R^3$, Y, $Y^1$, $Y^2$, A and l are as defined above.

The reaction of the compound (10) and the compound (21) is carried out under the same conditions as used in the reaction of the compounds (8) and (9) in Reaction Scheme-II. The oxidation of the compound (22) is also done in the same manner as in Reaction Scheme-IV. The compound (22') is easily converted into the compound (23) by treating it in the same manner as in the conventional method for the preparation of a Grignard reagent, for example, by treating the compound (22') with magnesium in an appropriate solvent at room temperature to 100° C. for 30 minutes to serveral hours. In this reaction, magnesium is used in an amount of at least equimolar, preferably 1 to 1.5 mole to 1 mole of the compound (22'). Besides, the reaction of the compound (23) and the compound (24) is carried out under the same conditions as used in the reaction of the compounds (16) and (17) in Reaction Scheme-VI.

Reaction Scheme-X

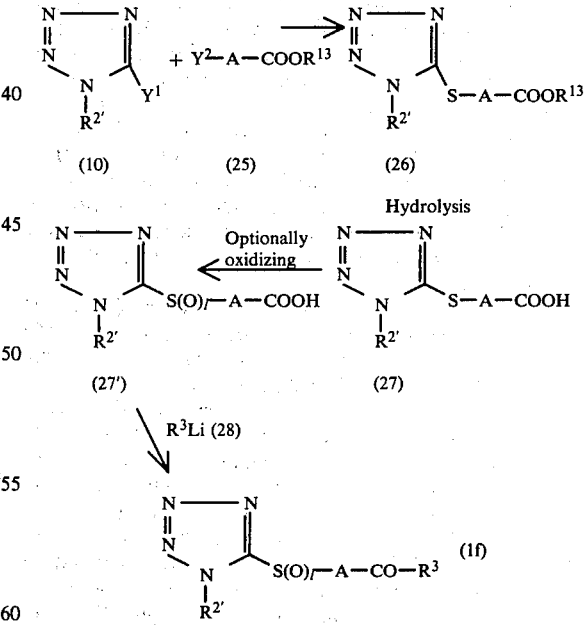

wherein $R^{2'}$, $R^3$, $Y^1$, $Y^2$, A and l are as defined above, and $R^{13}$ is a lower alkyl.

The reaction of the compound (10) and the compound (25) is carried out under the same conditions as used in the reaction of the compounds (8) and (9) in Reaction Scheme-II. The hydrolysis of the compound (26) is done in the same manner as in the hydrolysis of the compound (1a) in Reaction Scheme-I. The oxidation of the compound (27) is also done in the same manner as in Reaction Scheme-IV. The reaction of the compound (27') and the compound (28) is carried out in an appropriate inert solvent at a temperature of −70° C. to room temperature, preferably −30° C. to room temperature, for a period of about 1 to 6 hours. Suitable examples of the inert solvent are ethers (e.g. diethyl ether, dioxane, tetrahydrofuran), aromatic hydrocarbons (e.g. benzene, toluene), saturated hydrocarbons (e.g. hexane, heptane, pentane, cyclohexane), or the like. The compound (28) is used in an amount of at least 2 moles, preferably 2 to 3 moles, to 1 mole of the compound (27').

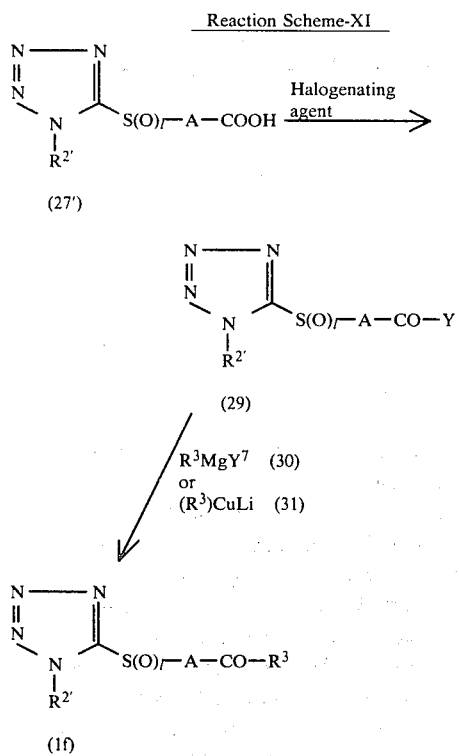

wherein $R^{2'}$, $R^3$, Y, A and l ae as defined above, and $Y^7$ is a halogen, and M is a metal such as zinc, cadmium, or magnesium.

The reaction of the compound (27') with the halogenating agent is carried out in the same manner as in the reaction of the compound (1b) with a halogenating agent in Reaction Scheme-I. The reaction of the compound (29) with the compound (30) or (31) is carried out under the same conditions as used in the reaction of the compound (27') and the compound (28) in Reaction Scheme-X. In this reaction, the compound (30) or (31) is used in an amount of at least equimolar, preferably 1 to 1.5 mole to 1 mole of the compound (29).

Reaction Scheme-XII

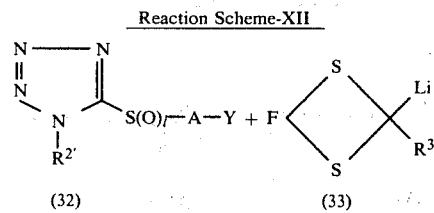

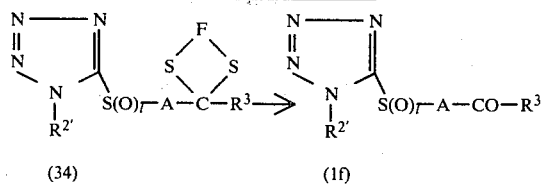

wherein $R^{2'}$, $R^3$, Y, A and l are as defined above, and F is a lower alkylene.

The reaction of the compound (32) and the compound (33) is carried out under the same conditions as used in the reaction of the compound (27') and the compound (28) in Reaction Scheme-X. The conversion of the compound (34) into the compound (1f) can be carried out in the same manner as in the convertion of the thioketal (wherein the keto group is protected with a lower alkanethiol or a lower alkylenedithio) into the corresponding carbonyl group in the Reaction Scheme-I.

The compounds (1) of the present invention wherein the group $R^3$ is a phenyl having hydroxy substituent may also be prepared by hydrolysis of the corresponding compound wherein the group $R^3$ is a phenyl having a lower alkoxy substituent, which is carried out, for example, by refluxing the compound in hydrobromic acid for 1 to 6 hours.

The compounds of the present invention may also be prepared by a process as shown in the following Reaction Scheme-XIII.

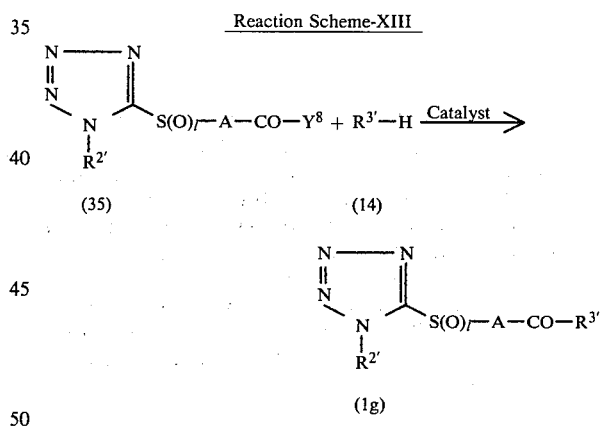

wherein $R^{2'}$, $R^{3'}$, A and l are as defined above, and $Y^8$ is a halogen, hydroxy, or the group

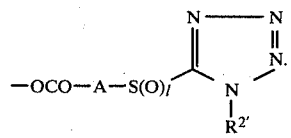

The reaction of the compound (35) and the compound (14) is carried out under the same conditions as used in the reaction of the compound (14) and the compound (15) in Reaction Scheme-V.

Moreover, the compounds (1) of the present invention wherein $R^1$ is the group $-S(O)_l-A-S(O)_n-R^3$ can be prepared by a process as shown in the following Reaction Scheme-XIV.

Reaction Scheme-XIV

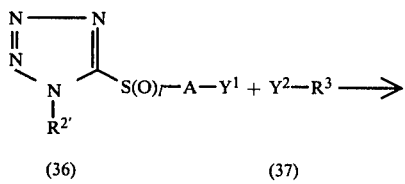

(36)         (37)

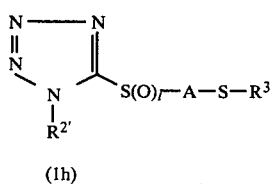

(1h)

wherein $R^{2'}$, $R^3$, A, $Y^1$, $Y^2$ and $l$ are as defined above.

The reaction of the compound (36) and the compound (37) is carried out under the same conditions as used in the reaction of the compound (8) and the compound (9) in Reaction Scheme-II.

The starting compound (36) used in the above Reaction Scheme-XIV can be prepared, for example, by processes as shown in the following Reaction Schemes-XV to XVII.

Reaction Scheme-XV

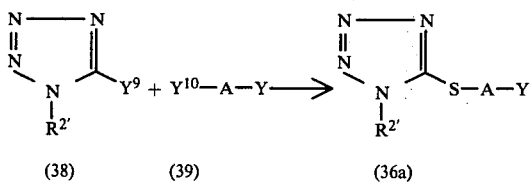

(38)         (39)         (36a)

wherein $R^{2'}$, A and Y are as defined above, $Y^9$ is mercapto or amidinothio group, and $Y^{10}$ is a halogen.

The reaction of the compound (38) and the compound (39) is carried out under the same conditions as used in the reaction of the compounds (8) and (9) in Reaction Scheme-II. In the above reaction, when the compound (38) is used in double or more amount, i.e. in 2 moles or more, preferably 2 to 4 moles, to 1 mole of the compound (39), there can directly be obtained the compounds (Ii) of the present invention having the following formula:

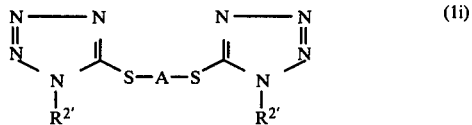  (Ii)

wherein $R^{2'}$ and A are as defined above.

Reaction Scheme-XVI

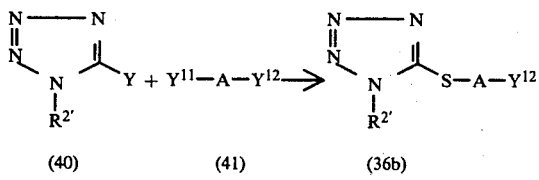

(40)         (41)         (36b)

wherein $R^{2'}$, A and Y are as defined above, $Y^{11}$ and $Y^{12}$ are each mercapto or amidinothio group.

The reaction of the compound (40) and the compound (41) is also carried out under the same conditions as used in the reaction of compounds (8) and (9) in Reaction Scheme-II. Besides, when the compound (40) is used in double or more amount, preferably 2 to 4 moles to 1 mole of the compound (41), the compounds (1i) of the present invention can directly be obtained like in Reaction Scheme-XV.

Reaction Scheme-XVII

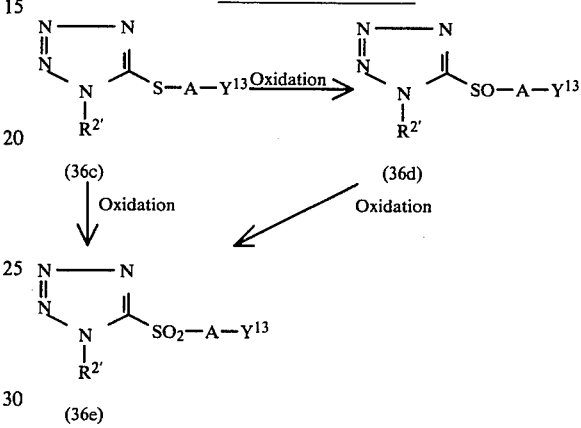

wherein $R^{2'}$ and A are as defined above, and $Y^{13}$ is a halogen, mercapto or amidinothio group.

The oxidation of the compound (36c) to convert into the compound (36d) and the oxidation of the compound (36d) to convert into the compound (36e) are done under the same conditions as used in the oxidation of the compound (11a) to the compound (11b) in Reaction Scheme-IV. Besides, the oxidation of the compound (36c) to convert into the compound (36e) can be done under the same conditions as used in the oxidation of the compound (11a) to the compound (11c) in Reaction Scheme-IV.

The compounds (1) of the present invention wherein the group $R^3$ is the group

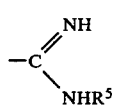

can be prepared by a process as shown in the following Reaction Scheme-XVIII.

Reaction Scheme-XVIII

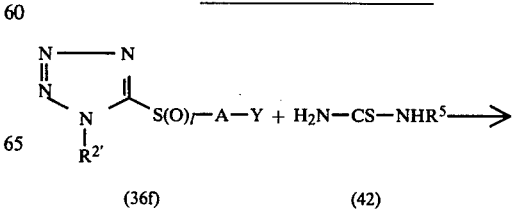

(36f)         (42)

-continued
Reaction Scheme-XVIII (1j)

wherein $R^{2'}$, $R^5$, A, Y and l are as defined above.

The reaction of the compound (36f) and the compound (42) is carried out under the same conditions as used in the reaction of the compound (11d) or (11e) with thiourea in Reaction Scheme-V.

The sulfoxide or sulfone derivatives (1l) of the present compounds can be prepared by a process as shown in the following Reaction Scheme-XIX.

Reaction Scheme-XIX (1k)

(1l)

wherein $R^{2'}$, $R^3$, A and m are as defined above, X' is the group $S(O)_n$, or —CO—, X'' is the group $S(O)_{n''}$ or —CO—, and l', l'', n' and n'' are each 0, 1 or 2, provided that these symbols l', l'', n' and n'' are in the range of $(l''+n'')-(l'+n') \geq 1$.

The oxidation of the compound (1k) to convert into the compound (1l) can be done in the same manner as in the oxidation reaction in Reaction Scheme-IV, wherein the number of oxygen to be introduced can be controlled by regulating the amount of the oxidizing agent. For instance, in case of introducing one oxygen into the compound (1k), the oxidizing agent is used in an amount of 1 mole or more, preferably 1 to 1.5 mole, to 1 mole of the compound (1k); in case of introducing two oxygens, the oxidizing agent is used in an amount of 2 moles or more, preferably 2 to 2.5 moles, to 1 mole of the compound (1k); in case of introducing three oxygens, the oxidizing agent is used in an amount of 3 moles or more, preferably 3 to 3.5 moles, to 1 mole of the compound (1k); and in case of introducing four oxygens, the oxidizing agent is used in an amount of 4 moles or more, preferably 4 to 6 moles, to 1 mole of the compound (1k).

Moreover, the compounds (1) of the present invention can also be prepared by processes as shown in the following Reaction Schemes-XX to XXV.

Reaction Scheme-XX (1r)   (43)

(1s)

wherein $R^{2'}$, $R^6$, $R^9$, A, Y and l are as defined above.

The reaction of the compound (1r) and the compound (43) is carried out under the same conditions as used in the reaction of the compounds (8) and (9) in Reaction Scheme-II.

Reaction Scheme-XXI (36f)   (45)

(1t)

wherein $R^{2'}$, $R^6$, A, Y and l are as defined above, and $R^{14}$ is hydrogen, a lower alkyl or a tetrazolyl which may have a lower alkyl substituent.

The reaction of the compound (36f) and the compound (45) is also carried out under the same conditions as used in the reaction of the compounds (8) and (9) in Reaction Scheme-II.

Reaction Scheme-XXII (36f)   (46)

(1u)

-continued
Reaction Scheme-XXII

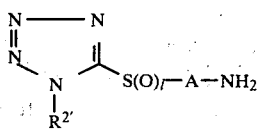

(1v)

wherein R²′, A, Y and l are as defined above.

The reaction of the compound (36f) and the compound (46) is also carried out under the same conditions as used in the reaction of the compounds (8) and (9) in Reaction Scheme-II. The hydrolysis of the compound (1u) is done in the same manner as in the hydrolysis of the compound (1a) in Reaction Scheme-I.

Reaction Scheme-XXIII

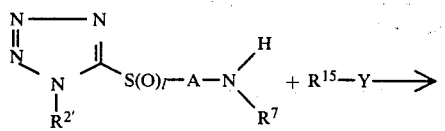

(1w)    (47)

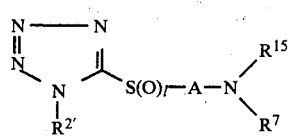

(1x)

wherein R²′, R⁷, A and l are as defined above, and R¹⁵ is a lower alkyl or a phenyl(lower)alkyl.

The reaction of the compound (1w) and the compound (47) is carried out in an appropriate solvent or without using any solvent in the presence of a basic compound at a temperature of −30° to 100° C., preferably room temperature to 70° C., for a period of about 30 minutes to 12 hours. Suitable examples of the basic compound are alkali metal hydrides (e.g. sodium hydride, potassium hydride), alkali metals (e.g. sodium, potassium), alkali metal amides (e.g. sodium amide, potassium amide), or the like. Suitable examples of the solvent are ethers (e.g. dioxane, tetrahydrofuran), aromatic hydrocarbons (e.g. benzene, toluene, xylene), dimethylformamide, dimethyl sulfoxide, hexamethylphosphoric triamide, or the like. The compound (47) is used to an amount of at least 1 mole, preferably 1 to 2 moles, to 1 mole of the compound (1w).

Reaction Scheme-XXIV

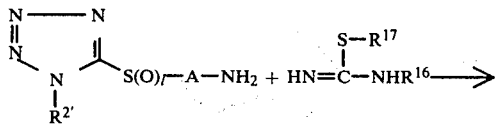

(1v)    (48)

-continued
Reaction Scheme-XXIV

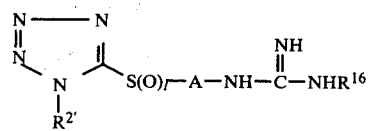

(1y)

wherein R²′, A and l are as defined above, and R¹⁶ and R¹⁷ are each a lower alkyl.

The reaction of the compound (1v) and the compound (48) is carried out in an appropriate inert solvent such as water, alcohols (e.g. methanol, ethanol, isopropanol), fatty acid esters (e.g. methyl acetate, ethyl acetate), dimethylformamide, dimethyl sulfoxide, preferably water or alcohols, at a temperature of from room temperature to 150° C., preferably 50° to 100° C., for a period of about 1 to 5 hours. The amount of the compound (1v) and the compound (48) is not critical, but the latter is usually used in an amount of at least equimole, preferably 1 to 1.5 mole, to 1 mole of the former.

Reaction Scheme-XXV

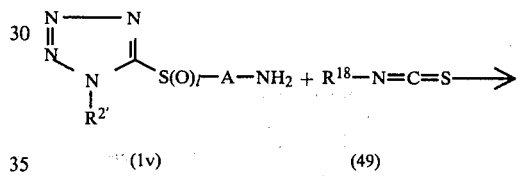

(1v)    (49)

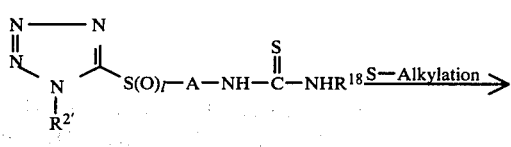

(1z)

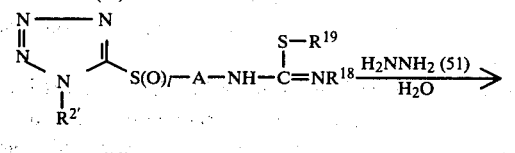

(50)

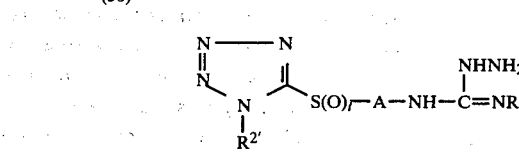

(1aa)

wherein R²′, A and l are as defined above, and R¹⁸ and R¹⁹ are each a lower alkyl.

The reaction of the compound (1v) and the compound (49) is carried out in the presence or absence of a solvent, such as water, alcohols (e.g. methanol, ethanol, isopropanol), aromatic hydrocarbons (e.g. benzene, toluene), halogenated hydrocarbons (e.g. chloroform, dichloromethane, chlorobenzene), acetone, tetrahydrofuran, preferably alcohols. The compound (49) is usually used in an amount of at least equimole, preferably 1 to 1.5 mole, to 1 mole of the compound (1v). The reaction is usually carried out at a temperature of from room temperature to 150° C., preferably room temperature to 100° C., for about 1 to 5 hours. The S-alkylation of the compound (1z) is done under the same conditions as in the reaction of the compounds (1v) and (49). Besides, the reaction of the compound (50) and the compound (51) is also done under the same conditions as in the reaction of the compounds (1v) and (48) in Reaction Scheme-XXIV.

The compounds (1) having an acidic group may be converted into a salt thereof with a pharmaceutically acceptable basic compound. The basic compound includes metal hydroxides such as sodium hydroxide or potassium hydroxide, alkali metal alcoholates such as sodium methylate or potassium ethylate, and the like. The compounds (1) having a basic group may also be converted into a salt with a pharmaceutically acceptable acid. The pharmaceutically acceptable acid includes inorganic acids such as sulfuric acid, nitric acid, hydrochloric acid or hydrobromic acid, and organic acids such as acetic acid, p-toluenesulfonic acid, ethanesulfonic acid, oxalic acid, maleic acid, succinic acid or benzoic acid.

The compounds obtained in the above processes can easily be isolated from the reaction mixture and purified by conventional methods. For instance, the isolation can be carried out by distillation, recrystallization, column chromatography, extraction, and the like.

The compounds (1) or their pharmaceutically acceptable salts of the present invention show excellent inhibiting activities against stress ulcers and indomethacin-induced ulcers with less side effects such as central nervous system activities, anti-cholinergic activity and the rate of gastric empting, and are useful as a medicine for the treatment of peptic and duodenal ulcers.

The compounds (1) or their salts of the present invention are usually used in the form of conventional pharmaceutical preparations. The pharmaceutical preparations can be prepared by using conventional diluents and carriers such as fillers, bulking agents, binding agents, wetting agents, disintegrators, surface active agents, lubricants, or the like. The preparations may be in various forms, such as tablets, pills, powders, solutions, suspentions, emulsions, granules, capsules, suppositories, injections (solution suspension, etc.), and the like. The tablets can be prepared by using conventional carriers, such as excipients (e.g., lactose, sucrose, sodium chloride, glucose, urea, starches, calcium carbonate, kaolin, crystalline cellulose, silicic acid, etc.), binding agents (e.g. water, ethanol, propanol, simple syrup, aqueous glucose solution, aqueous solution of starches, aqueous gelatine solution, carboxymethyl cellulose, shellac, methyl cellulose, potassium phosphate, polyvinyl pyrrolidone, etc.), disintegrators (e.g. dry starches, sodium arginate, agar powder, laminaran powder, sodium hydrogen carbonate, calcium carbonate, polyoxyethylene sorbitan fatty acid esters, sodium laurylsulfate, monoglyceryl stearate, starches, lactose, etc.), disintegration inhibitors (e.g. sucrose, stearin, cacao butter, hydrogenated oils, etc.), absorption accelerators (e.g. quaternary ammonium salt, sodium laurylsulfate, etc.), humectants (e.g. glycerin, starches, etc.), adsorbents (e.g. starches, lactose, kaolin, bentonite, colloidal silica, etc.), lubricants (e.g. purified talc, stearic acid salts, boric acid powder, polyethylene glycol, etc.), and the like. The tablets may be in the forms of sugar coating tablets, gelatine coating tablets, enteric coating tablets, film coating tablets, double or multiple layers tablets, and the like. The pills can be prepared by using conventional carriers, such as excipients (e.g. glucose, lactose, starches, cacao butter, hardened vegetable oils, kaolin, talc, etc.), binding agents (e.g. gum arabic powder, tragacanth powder, gelatin, ethanol, etc.), disintegrators (e.g. laminaran, agar, etc.), and the like. The suppositories can be prepared by using conventional carriers, such as polyethylene glycol, cacao butter, higher alcohols or their esters, gelatin, semi-synthetic glycerides, or the like. When the active compounds are prepared in the form of an injection, a solution or suspension containing the active compounds is sterilized and made isotonic to blood. The injections in the form of a solution, emulsion or suspension can be prepared by using conventional diluents, such as water, ethyl alcohol, propylene glycol, ethoxylated isostearyl alcohol, polyoxy-isostearyl alcohol, polyoxyethylene sorbitan fatty esters, or the like. The injection preparation may be made isotonic by adding thereto a sufficient amount of sodium chloride, glucose, glycerin, or the like and may optionally be incorporated with conventional solubilizers, buffer solutions, pain killers, colorants, preservatives, perfumes, flavors, sweetening agents, and other medicaments.

The anti-ulcer preparations of the present invention may contain a wide range of amount of the active compounds and contains usually about 1 to 70% by weight, preferably 5 to 50% by weight, of the active compounds of the present invention based on the total weight of the preparations.

The administration route of the anti-ulcer preparations of the present invention is not restricted, and suitable administration route is determined by the forms of the preparations, age, sex and other conditions of patients to be treated, severity of disease, and the like. Tablets, pills, solutions, suspensions, emulsions, granules and capsules are usually administered in oral route. Injections are usually administered in intravenous route alone or optionally together with an appropriate adjuvant such as glucose or amino acids or may be administered alone in intramuscular, intracutaneous, subcutaneous, or intraperitoneal route.

The dose of the active compounds of the present invention may vary with the usage, age, sex and other conditions of patients to be treated, severity of disease, or the like, but is usually in the range of 0.6 to 50 mg/kg of body weight per day. The active compounds of the present invention are preferably contained in the anti-ulcer preparations in a dosage unit of 10 to 1000 mg.

Pharmacological tests

The pharmacological activities of the compounds (1) of the present invention were tested by conventional methods as mentioned hereinafter with respect to the following compounds:

1. 1-Methyl-5-[4-(1-methyl-1,2,3,4-tetrazol-5-yl)thiobutyl]thio-1,2,3,4-tetrazole
2. 1-Methyl-5-[3-(2-pyridyl)thiopropyl]thio-1,2,3,4-tetrazole
3. 1-Methyl-5-(3-cyclohexylthiopropyl)thio-1,2,3,4-tetrazole
4. 1-Methyl-5-[3-(5-methyl-1,3,4-oxadiazol-2-yl)thiopropyl]thio-1,2,3,4-tetrazole
5. 1-Methyl-5-[5-(1-methyl-1,2,3,4-tetrazol-5-yl)thiopentyl]thio-1,2,3,4-tetrazole
6. 1-Methyl-5-[3-(1-methyl-1,2,3,4-tetrazol-5-yl)thio-3-methylpropyl]thio-1,2,3,4-tetrazole
7. 1-Methyl-5-(3-ethylthiopropyl)thio-1,2,3,4-tetrazole 8. 1-Methyl-5-(3-butylthiopropyl)thio-1,2,3,4-tetrazole
9. 1-Methyl-5-[2-methyl-3-(1-methyl-1,2,3,4-tetrazol-5-yl)thiopropyl]thio-1,2,3,4-tetrazole
10. 1-Methyl-5-(3-phenylthiopropyl)thio-1,2,3,4-tetrazole
11. 1-Methyl-5-[3-(1-methylimidazol-2-yl)thiopropyl]thio-1,2,3,4-tetrazole
12. 1-Methyl-5-[3-(5-amino-1,3,4-thiadiazol-2-yl)thiopropyl]thio-1,2,3,4-tetrazole
13. 1-Methyl-5-[3-(4-methyl-2-pyrimidyl)thiopropyl]thio-1,2,3,4-tetrazole
14. 1-Methyl-5-[3-(3-hydroxy-2-pyridyl)thiopropyl]thio-1,2,3,4-tetrazole
15. 1-Methyl-5-[3-(4,5-dimethyl-1,2,4-triazol-3-yl)thiopropyl]thio-1,2,3,4-tetrazole
16. 5-(3-Phenylthiopropyl)thio-1,2,3,4-tetrazole
17. 1-Methyl-5-[3-(2-amino-4-thiazolyl)methylthiopropyl]thio-1,2,3,4-tetrazole
18. 1-Methyl-5-[3-(2-quinolyl)thiopropyl]thio-1,2,3,4-tetrazole
19. 1-Methyl-5-[3-(2-benzimidazolyl)thiopropyl]thio-1,2,3,4-tetrazole
20. 1-Methyl-5-[3-(2-naphthyl)thiopropyl]thio-1,2,3,4-tetrazole
21. 1-Methyl-5-[3-(2-furyl)methylthiopropyl]thio-1,2,3,4-tetrazole
22. 1-Methyl-5-(3-benzylthiopropyl)thio-1,2,3,4-tetrazole
23. 1-Methyl-5-[3-(2-pyridyl)methylthiopropyl]thio-1,2,3,4-tetrazole
24. 1-Methyl-5-[3-(4-methyl-2-thiazolyl)thiopropyl]thio-1,2,3,4-tetrazole
25. 1-Methyl-5-[3-(4-pyridyl)thiopropyl]thio-1,2,3,4-tetrazole
26. 1-Methyl-5-[3-(2-amino-6-methyl-4-pyrimidyl)thiopropyl]thio-1,2,3,4-tetrazole
27. 1-Methyl-2-[4-(1-methyl-1,2,3,4-tetrazol-5-yl)thiobutyl]isothiourea hydrobromide
28. 1-Methyl-5-(4-phenylthiobutyl)thio-1,2,3,4-tetrazole
29. 1-Methyl-5-[4-(4-oxo-3,4-dihydroquinazolin-2-yl)thiobutyl]thio-1,2,3,4-tetrazole
30. 1-Cyclohexyl-5-(3-ethylthiopropyl)thio-1,2,3,4-tetrazole
31. 1-Methyl-5-[2-(2-pyridyl)thioethyl]thio-1,2,3,4-tetrazole
32. 1-Methyl-5-[5-(2-pyridyl)thiopentyl]thio-1,2,3,4-tetrazole
33. 1-Methyl-5-[6-(2-pyridyl)thiohexyl]thio-1,2,3,4-tetrazole
34. 1-Methyl-5-[2-methyl-3-(2-pyridyl)thiopropyl]thio-1,2,3,4-tetrazole
35. 1-Methyl-5-[2-(1-methyl-1,2,3,4-tetrazol-5-yl)thioethyl]thio-1,2,3,4-tetrazole
36. 1-Methyl-5-[6-(1-methyl-1,2,3,4-tetrazol-5-yl)thiohexyl]thio-1,2,3,4-tetrazole
37. 1-Methyl-5-[3-(1-methyl-1,2,3,4-tetrazol-5-yl)thiopropyl]thio-1,2,3,4-tetrazole
38. 1-Phenyl-5-[3-(1-phenyl-1,2,3,4-tetrazol-5-yl)thiopropyl]thio-1,2,3,4-tetrazole
39. 1-Methyl-5-[3-(1-phenyl-1,2,3,4-tetrazol-5-yl)thiopropyl]thio-1,2,3,4-tetrazole
40. 1-Methyl-5-[3-(5-nitro-2-pyridyl)thiopropyl]thio-1,2,3,4-tetrazole
41. 1-Methyl-5-[3-(4-chlorobenzyl)thiopropyl]thio-1,2,3,4-tetrazole
42. 1-Methyl-5-[3-methyl-3-(5-methyl-1,3,4-oxadiazol-2-yl)thiopropyl]thio-1,2,3,4-tetrazole
43. 1-Methyl-1,2,3,4-tetrazol-5-yl 3-methyl-3-(5-methyl-1,3,4-oxadiazol-2-yl)thiopropyl sulfoxide
44. 3-(1-Methyl-1,2,3,4-tetrazol-5-yl)thiopropyl 2-pyridyl sulfoxide
45. 1-Methyl-1,2,3,4-tetrazol-5-yl 4-(2-pyridyl)thiobutyl sulfoxide
46. 4-(1-Methyl-1,2,3,4-tetrazol-5-yl)thiobutyl 1-methyl-1,2,3,4-tetrazol-5-yl sulfoxide
47. 4-(1-Methyl-1,2,3,4-tetrazol-5-yl)thiobutyl 1-methyl-1,2,3,4-tetrazol-5-yl sulfone
48. 3-(1-Methyl-1,2,3,4-tetrazol-5-yl)thiopropyl 2-pyridyl sulfone
49. 1-Methyl-1,2,3,4-tetrazol-5-yl 3-methyl-3-(1-methyl-1,2,3,4-tetrazol-5-yl)thiopropyl sulfoxide
50. 1-Methyl-5-(3-propionylpropyl)thio-1,2,3,4-tetrazole
51. 1-Phenyl-5-(3-benzoylpropyl)thio-1,2,3,4-tetrazole
52. 1-Cyclohexyl-5-(3-cyclohexylcarbonylpropyl)thio-1,2,3,4-tetrazole
53. 1-Methyl-5-(3-benzoylpropyl)thio-1,2,3,4-tetrazole
54. 1-Methyl-5-[3-(2-thenoyl)propyl]thio-1,2,3,4-tetrazole
55. 1-Methyl-5-[3-(2-furoyl)propyl]thio-1,2,3,4-tetrazole
56. 1-Methyl-5-[3-(3,4-dimethoxybenzoyl)propyl]thio-1,2,3,4-tetrazole
57. 1-Methyl-5-(3-benzylcarbonylpropyl)thio-1,2,3,4-tetrazole
58. 1-Methyl-5-[3-(4-acetylaminobenzoyl)propyl]thio-1,2,3,4-tetrazole
59. 1-Methyl-5-(3-acetylpropyl)thio-1,2,3,4-tetrazole
60. 1-Methyl-5-[3-($\beta$-phenethylcarbonyl)propyl]thio-1,2,3,4-tetrazole
61. 1-Methyl-5-(benzoylmethyl)thio-1,2,3,4-tetrazole
62. 1-Methyl-5-(3-pentanoylpropyl)thio-1,2,3,4-tetrazole
63. 1-Methyl-5-[3-(4-methoxybenzoyl)propyl]thio-1,2,3,4-tetrazole
64. 1-Methyl-5-[3-(5-methyl-2-thenoyl)propyl]thio-1,2,3,4-tetrazole
65. 1-Methyl-5-(3-cyclopentylcarbonylpropyl)thio-1,2,3,4-tetrazole
66. 1-Methyl-5-(3-cyclohexylcarbonylpropyl)thio-1,2,3,4-tetrazole
67. 1-Methyl-5-acetylmethyl)thio-1,2,3,4-tetrazole
68. 1-Methyl-5-[3-(4-hydroxybenzoyl)propyl]thio-1,2,3,4-tetrazole
69. 1-Methyl-5-[3-(4-ethylbenzoyl)propyl]thio-1,2,3,4-tetrazole
70. 1-Methyl-5-[3-(4-chlorobenzoyl)propyl]thio-1,2,3,4-tetrazole
71. 1-Methyl-5-(4-benzoylbutyl)thio-1,2,3,4-tetrazole
72. 1-Methyl-5-(5-benzoylpentyl)thio-1,2,3,4-tetrazole
73. 1-Methyl-5-[3-(2-pyrrolyl)carbonylpropyl]thio-1,2,3,4-tetrazole
74. 1-Methyl-5-[3-(2-pyridyl)carbonylpropyl]thio-1,2,3,4-tetrazole
75. 1-Methyl-5-[3-(5-chloro-2-thenoyl)propyl]-thio-1,2,3,4-tetrazole
76. 1-Methyl-5-[3-(5-carboxymethyl-2-furoyl)-propyl]thio-1,2,3,4-tetrazole
77. 1-Phenyl-5-(3-cyclohexylcarbonylpropyl)thio-1,2,3,4-tetrazole
78. 5-Acetylmethylthio-1,2,3,4-tetrazole
79. 1-Methyl-5-[3-(4-butoxybenzoyl)propyl]thio-1,2,3,4-tetrazole
80. 1-Methyl-5-[3-(4-methyl-5-thiazolyl)carbonylpropyl]thio-1,2,3,4-tetrazole 81. 1-Methyl-5-(3-cyclohexylcarbonylaminopropyl)thio-1,2,3,4-tetrazole
82. 1-Methyl-5-[3-(N-ethyl-N-propionylamino)propyl]thio-1,2,3,4-tetrazole
83. 1-Methyl-5-[3-(N-methyl-N-acetylamino)propyl]thio-1,2,3,4-tetrazole
84. 1-Methyl-5-[3-(N,N-diethylamino)propyl]thio-1,2,3,4-tetrazole
85. 1-Methyl-5-[3-(phthalimido)propyl]thio-1,2,3,4-tetrazole
86. 1-Methyl-5-(3-acetylaminopropyl)thio-1,2,3,4-tetrazole
87. 1-Methyl-5-(3-propionylaminopropyl)thio-1,2,3,4-tetrazole
88. 1-Methyl-5-(3-benzoylaminopropyl)thio-1,2,3,4-tetrazole
89. 1-Methyl-5-[3-(N-methyl-N-cyclohexylcarbonylamino)propyl]thio-1,2,3,4-tetrazole
90. 1-Methyl-5-[3-(N-ethyl-N-cyclohexylcarbonylamino)propyl]thio-1,2,3,4-tetrazole
91. 1-Methyl-5-[3-(N-ethyl-N-benzoylamino)propyl]thio-1,2,3,4-tetrazole
92. 1-Methyl-5-[3-(N-ethyl-N-cyclopentylcarbonylamino)propyl]thio-1,2,3,4-tetrazole
93. 1-Methyl-5-{3-[N-ethyl-N-(2-furylcarbonyl)amino]propyl}thio-1,2,3,4-tetrazole
94. 1-Methyl-5-[3-(N-benzyl-N-propionylamino)propyl]thio-1,2,3,4-tetrazole
95. 1-Methyl-5-(3-hexanoylaminopropyl)thio-1,2,3,4-tetrazole
96. 1-Methyl-5-[3-(4-methoxybenzoylamino)propyl]thio-1,2,3,4-tetrazole
97. 1-Phenyl-5-[3-(N-ethyl-N-benzoylamino)propyl]thio-1,2,3,4-tetrazole
98. 1-Methyl-5-(2-pyridylmethyl)thio-1,2,3,4-tetrazole
99. 1-[3-(1-Methyl-1,2,3,4-tetrazol-5-yl)thiopropyl]-3-methylthiourea
100. 1-Methyl-[3-(5-methylamino-1,2,3,4-tetrazol-1-yl)propyl]thio-1,2,3,4-tetrazole
101. 1-Methyl-5-[3-(3-methylguanidino)propyl]thio-1,2,3,4-tetrazole hydroiodide
102. 1-Amino-2-methyl-3-[3-(1-methyl-1,2,3,4-tetrazol-5-yl)thiopropyl]guanidine hydroiodide
103. 1-Methyl-5-cyclohexylmethylthio-1,2,3,4-tetrazole
104. 1-Methyl-5-(4-methoxybenzyl)thio-1,2,3,4-tetrazole
105. N,N-Diethyl-4-(5-methyl-1,2,3,4-tetrazol-1-yl)butyramide
106. N-Ethyl-N-cyclohexyl-4-(5-methyl-1,2,3,4-tetrazol-1-yl)butyramide
107. N,N-Dipropyl-4-(5-methyl-1,2,3,4-tetrazol-1-yl)butyramide
108. N-Butyl-4-(5-methyl-1,2,3,4-tetrazol-1-yl)butyramide
109. 4-(5-Methyl-1,2,3,4-tetrazol-1-yl)butyric acid
110. Methyl 4-(5-Methyl-1,2,3,4-tetrazol-1-yl)butyrate
111. N,N-Diethyl-4-(5-phenyl-1,2,3,4-tetrazol-1-yl)butyramide
112. 5-Methyl-1-[3-(4-methyl-1-piperazinylcarbonyl)propyl]-1,2,3,4-tetrazole
113. N-(2-Furyl)methyl-4-(5-methyl-1,2,3,4-tetrazol-1-yl)butyramide
114. N-[2-(3,4-Dimethoxyphenyl)ethyl]-4-(5-methyl-1,2,3,4-tetrazol-1-yl)butyramide
115. N-(2-Methyl-3-chlorophenyl)-4-(5-methyl-1,2,3,4-tetrazol-1-yl)butyramide
116. N-Ethyl-N-(2-hydroxycyclohexyl)-4-(5-methyl-1,2,3,4-tetrazol-1-yl)butyramide
117. 5-Methyl-1-(3-morpholinocarbonylpropyl)-1,2,3,4-tetrazole Pharmacological Test 1

The pharmacological activities of the compounds (1) were tested by a Shay rat pylorus ligation method (cf. H. Shay et al: Gastroenterol., Vol. 5, page 43, 1945) which is the most popular method for testing of gastric juice secretion-inhibiting activity. The test was carried out by using male Wistar rats, weighing about 170 g and fasting for 24 hours.

Test compounds were administered 30 minutes before the pylorus ligation in a dose of 100 mg/kg in subcutaneous route in case of test compounds 37, 38, 50, 51 and 52, in a dose of 200 mg/kg in subcutaneous route in case of test compounds 105 and 106 and in dose of 100 mg/kg in duodenal route in case of other test compounds, and the volume, total acidity and pepsin activity of the gastric juice were measured 4 hours after the ligation. As a control, a saline solution was administered instead of the test compound. The inhibitory ratio (%) of the test compounds were calculated when the inhibitory activities of the control were counted as zero (0). The results are shown in the following Table 1.

In the table, the inhibitory ratio (%) was evaluated as follows:

+: 10 to less than 50%
++: more than 50% while in case of the test compounds star-marked (*), it was evaluated as follows:

+: 30 to less than 60%
++: more than 60%.

TABLE 1

| Test compound No. | Inhibitory ratio | | |
|---|---|---|---|
| | Volume of gastric juice | Total acidity | Pepsin activity |
| 1* | ++ | ++ | + |
| 2* | ++ | ++ | + |
| 3* | ++ | ++ | − |
| 4* | ++ | ++ | + |
| 5* | ++ | ++ | + |
| 6* | ++ | ++ | − |
| 7 | ++ | | |
| 8 | ++ | | |
| 10 | + | | |
| 11 | ++ | | |
| 13 | ++ | | |
| 16 | + | | |
| 18 | + | | |
| 19 | + | | |
| 20 | + | | |
| 21 | ++ | | |
| 22 | ++ | | |
| 23 | + | | |
| 24 | ++ | | |
| 25 | ++ | | |
| 27 | ++ | | |
| 28 | + | | |
| 12 | + | | |
| 17 | + | | |
| 29 | + | | |
| 31 | ++ | | |
| 32 | + | | |
| 33 | + | | |
| 34 | ++ | | |
| 35 | ++ | | |
| 36 | ++ | | |
| 37 | ++ | ++ | ++ |
| 38 | + | + | + |
| 39 | + | | |
| 44 | ++ | | |
| 45 | + | | |
| 46 | + | | |
| 47 | ++ | | |

TABLE 1-continued

| Test compound No. | Inhibitory ratio | | |
|---|---|---|---|
| | Volume of gastric juice | Total acidity | Pepsin activity |
| 48 | + | | |
| 50 | ++ | ++ | ++ |
| 51 | + | + | ++ |
| 52 | + | + | + |
| 53 | ++ | ++ | + |
| 54 | ++ | ++ | − |
| 55 | ++ | ++ | + |
| 56 | + | + | + |
| 43 | + | | |
| 49 | + | | |
| 57 | ++ | + | + |
| 58 | + | − | + |
| 59 | ++ | ++ | + |
| 60 | ++ | + | − |
| 61 | ++ | + | − |
| 62 | + | + | + |
| 63 | + | − | − |
| 64 | + | + | + |
| 65 | + | | |
| 66 | + | | |
| 67 | ++ | | |
| 68 | + | | |
| 71 | + | | |
| 72 | ++ | | |
| 73 | ++ | | |
| 74 | ++ | | |
| 77 | + | | |
| 78 | + | | |
| 81 | + | + | + |
| 82 | ++ | ++ | + |
| 83 | ++ | ++ | + |
| 84 | + | + | + |
| 85 | ++ | ++ | ++ |
| 86 | + | | |
| 87 | ++ | | |
| 88 | ++ | | |
| 90 | ++ | | |
| 91 | + | | |
| 93 | + | | |
| 94 | + | | |
| 96 | ++ | | |
| 97 | + | | |
| 98 | ++ | | |
| 99 | ++ | | |
| 101 | + | | |
| 102 | + | | |
| 103 | + | | |
| 105 | + | + | + |
| 106 | + | + | + |
| 108 | + | | |
| 109 | + | | |
| 110 | + | | |
| 80 | ++ | | |
| 92 | + | | |
| 104 | ++ | | |

Pharmacological Test 2: Stress ulcer

After male Wistar rats weighing about 170 g was fasted for 24 hours, the rats were restrained in a stress cage and dipped in water bath at 23° C. till chest of the animals. After 7 hours, the rats were killed and the stomach was isolated. Into the isolated stomach 10% formalin (8 ml) was poured and settled. The stomach was cut open at the greater curvature, and the length of each ulcer on the membrane was measured. Sum of the length of all ulcers was shown as ulcer index (UI). The test compound was orally administered to the rats before restraint in a stress cage in a dose of 300 mg/kg in the form of 0.5% CMC suspension in case of test compounds 3, 4, 6, 15 and 27 and in a concentration of 1×10⁻³ mole in case of other test compounds. As a control, only the solvent (CMC solution) was administered likewise. The inhibitory ratio (%) of stress ulcer of the test compounds was calculated by the following equation:

$$\text{Inhibitory ratio} = \frac{(UI \text{ of rats of control}) - (UI \text{ of rats administered test compound})}{UI \text{ of rats of control}} \times 100$$

The results are shown in Table 2. In the table, the inhibitory ratio (%) was evaluated as follows:
+: 30 to less than 60%
++: more than 60%.

TABLE 2

| Test comp. No. | Inhibitory ratio | Test comp. No. | Inhibitory ratio | Test comp. No. | Inhibitory ratio |
|---|---|---|---|---|---|
| 3 | ++ | 41 | ++ | 84 | ++ |
| 4 | ++ | 42 | ++ | 87 | ++ |
| 6 | ++ | 43 | ++ | 88 | ++ |
| 7 | ++ | 44 | ++ | 89 | ++ |
| 8 | ++ | 45 | ++ | 90 | ++ |
| 12 | ++ | 46 | ++ | 91 | ++ |
| 14 | ++ | 49 | ++ | 92 | ++ |
| 15 | ++ | 54 | ++ | 95 | + |
| 17 | ++ | 55 | + | 98 | ++ |
| 21 | ++ | 56 | + | 100 | ++ |
| 24 | ++ | 57 | ++ | 104 | ++ |
| 25 | ++ | 59 | + | 105 | ++ |
| 26 | ++ | 62 | ++ | 107 | ++ |
| 27 | ++ | 63 | ++ | 111 | ++ |
| 30 | ++ | 64 | + | 112 | ++ |
| 31 | ++ | 67 | ++ | 113 | + |
| 33 | ++ | 74 | ++ | 114 | + |
| 34 | ++ | 75 | ++ | 115 | + |
| 36 | ++ | 79 | ++ | 116 | + |
| 40 | ++ | 80 | ++ | 117 | + |
| 2 | ++ | 82 | ++ | | |
| 5 | ++ | 83 | ++ | | |

Pharmacological Test 3: Indomethacin-induced ulcer

After male Wistar rats weighing about 160 g was fasted for 24 hours, indomethacin was subcutaneously administered to the rats in a dose of 20 mg/kg in the form of a suspension in a mixture of 0.5% CMC and a small amount of Tween 80 (i.e. polyoxyethylene sorbitan monooleate). After 5 hours, the rats were killed and the stomach was isolated. Into the isolated stomach 10% formalin (8 ml) was poured and settled. The stomach was cut open at the greater curvature, and the length of each ulcer on the membrane was measured, based on which results the inhibitory ratio of the indomethacin-induced ulcer of the test compounds was calculated in the same manner as in Pharmacological Test 2. The test compound was orally administered to the rats in a dose of 100 mg/kg in the form of 0.5% CMC suspension 30 minutes before the administration of indomethacin.

The results are shown in Table 3. In the table, the inhibitory ratio (%) was evaluated as follows:
+: 30 to less than 60%
++: more than 60%.

TABLE 3

| Test compound No. | Inhibitory ratio | Test compound No. | Inhibitory ratio |
|---|---|---|---|
| 3 | + | 63 | ++ |
| 4 | ++ | 64 | ++ |
| 5 | ++ | 67 | ++ |
| 6 | ++ | 69 | ++ |
| 9 | ++ | 70 | ++ |
| 53 | ++ | 76 | ++ |

TABLE 3-continued

| Test compound No. | Inhibitory ratio | Test compound No. | Inhibitory ratio |
|---|---|---|---|
| 54 | ++ | 84 | ++ |
| 55 | ++ | 105 | + |
| 61 | + | 106 | + |
| 62 | + | | |

Acute toxicity

The test compounds were orally administered to male Wistar rats, and the half lethal dose ($LD_{50}$) was measured. The results are shown in Table 4.

TABLE 4

| Test compound No. | $LD_{50}$ (mg/kg, p.o.) |
|---|---|
| 4 | >500 |
| 7 | >500 |
| 25 | >500 |
| 44 | >500 |
| 54 | >500 |
| 67 | >500 |
| 90 | >500 |
| 92 | >500 |
| 105 | >500 |
| 106 | >500 |

The following Reference Examples and Examples further illustrate the present invention in detail.

REFERENCE EXAMPLE 1

1-Methyl-5-mercapto-1,2,3,4-tetrazole (4.6 g) and 1-bromo-3-chloropropane (9.4 g) are dissolved in acetone (100 ml). Potassium carbonate (6.8 g) is added to the solution and the mixture is refluxed for 3 hours. Acetone is distilled off and water is added to the residue. The mixture is extracted with chloroform and the chloroform solution is washed with saturated aqueous sodium chloride and dried over magnesium sulfate. Chloroform is distilled off and the residue is purified by silica gel column chromatography (Wakogel C-200 made by Wako Jun Yaku Co., Ltd.). The column is eluted with benzene-ether (5:1, V/V) to obtain 1-methyl-5-(3-chloropropyl)thio-1,2,3,4-tetrazole (8.5 g) as colorless liquid. $n_D^{14} = 1.5396$

REFERENCE EXAMPLE 2

According to the same procedure as described in Reference Example 1, the following compounds are obtained:
1-Cyclohexyl-5-(3-chloropropyl)thio-1,2,3,4-tetrazole, colorless liquid, $n_D^{14} = 1.5387$
1-Methyl-5-(4-bromobutyl)thio-1,2,3,4-tetrazole, colorless liquid, $n_D^{19} = 1.5530$

REFERENCE EXAMPLE 3

2-Merocaptopyridine (5.6 g) and 1-bromo-3-chloropropane (11.7 g) are dissolved in acetone (100 ml) and potassium carbonate (6.9 g) is added to the solution. The mixture is refluxed for 5 hours. After acetone is distilled off, water is added to the residue and the mixture is extracted with chloroform. The chloroform solution is washed with saturated aqueous sodium chloride and dried over magnesium sulfate. Chloroform is distilled off and the residue is purified by column chromatography (Kieselgel 60 made by Merck & Co.). After the column is eluted with chloroform-methanol, the eluate is distilled off to obtain 2-(3-chloropropyl)thiopyridine (8.2 g) as red oil.

NMR (90 MHz, CDCl$_3$): δ2.00–2.40 (2H, m), 3.30 (2H, t, J=6 Hz), 3.70 (2H, t, J=6 Hz), 6.80–7.60 (3H, m), 8.30–8.50 (1H, m)

REFERENCE EXAMPLE 4

According to the same procedure as described in Reference Example 3, the following compounds are obtained:
5-Amino-2-(3-chloropropyl)thio-1,3,4-thiadiazole, pale yellow needles, m.p. 121–121.5 (ethanol-water)
5-Methyl-2-(4-bromobutyl)thio-1,3,4-oxadiazole, brown liquid, NMR (90 MHz, CDCl$_3$): δ1.70–2.30 (4H, m), 2.43 (3H, s), 3.17 (2H, t, J=6 Hz), 3.43 (2H, t, J=6 Hz), 6.79 (1H, d, J=4.5 Hz), 8.32 (1H, d, J=4.5 Hz)

REFERENCE EXAMPLE 5

1-Methyl-5-(4-bromobutyl)thio-1,2,3,4-tetrazole prepared in Reference Example 2 is dissolved in formic acid (50 ml). 30% Aqueous hydrogen peroxide (2.3 g) is added to the solution with stirring at room temperature and the mixture is allowed to stand at room temperature for 2 overnights. The mixture is diluted with water and extracted with chloroform. The chloroform solution is washed with water, saturated aqueous sodium bicarbonate and then saturated aqueous sodium chloride and dried over magnesium sulfate. Chloroform is distilled off to obtain 1-methyl-1,2,3,4-tetrazol-5-yl 4-bromobutyl sulfoxide (5.5 g) as colorless liquid.

NMR (90 MHz, CDCl$_3$): δ1.80–2.30 (4H, m), 3.30–3.70 (4H, m), 4.34 (3H, s)

REFERENCE EXAMPLE 6

1-Methyl-5-(4-bromobutyl)thio-1,2,3,4-tetrazole prepared in Reference Example 2 is dissolved in formic acid (50 ml). 30% Aqueous hydrogen peroxide (6.9 g) is added to the solution and the mixture is stirred for 6 hours. Sodium hydrogen sulfite is added to the mixture with ice-cooling to destroy excess formic acid. Water is added to the mixture and the mixture is extracted with chloroform. The chloroform solution is washed with water and saturated aqueous sodium bicarbonate and dried over magnesium sulfate. Chloroform is distilled off and the residue is recrystallized from ethanol to obtain 1-methyl-1,2,3,4-tetrazole-5-yl 4-bromobutyl sulfone (2.9 g) as colorless flakes, m.p. 83.5°–85.5° C.

REFERENCE EXAMPLE 7

2-(3-Chloropropyl)thiopyridine (4.4 g) prepared in Reference Example 3 is dissolved in formic acid (40 ml). 30% Aqueous hydrogen peroxide (2.7 g) is added to the solution and the mixture is stirred at room temperature for 3 hours. The mixture is allowed to stand at room temperature for overnight, diluted with water and extracted with chloroform. The chloroform solution is washed with water, saturated aqueous sodium bicarbonate and saturated aqueous sodium chloride and dried over magnesium sulfate. Chloroform is distilled off and the residue is purified by column chromatography (Kieselgel 60). The column is eluted with chloroform-methanol (50:1) to obtain 2-pyridyl 3-chloropropyl sulfoxide (2.7 g) as colorless liquid.

NMR (90 MHz, CDCl$_3$): δ1.80–2.60 (2H, m), 2.80–3.50 (2H, m), 3.60 (2H, t, J=6 Hz), 7.30–7.50 (1H, m), 7.80–8.10 (2H, m), 8.50–8.70 (1H, m)

REFERENCE EXAMPLE 8

2-(3-Chloropropyl)thiopyridine (3.7 g) prepared in Reference Example 3 is dissolved in formic acid (30 ml). 30% Aqueous hydrogen peroxide (6.9 g) is added to the solution and the mixture is stirred at room temperature for 4 hours. After dilution with water, sodium hydrogen sulfite is added to the mixture with ice-cooling to destroy excess formic acid. The mixture is extracted with chloroform and the extract is washed with water, saturated aqueous sodium bicarbonate and saturated aqueous sodium chloride and dried over magnesium sulfate. Chloroform is distilled off and the residue is purified by column chromatography (Kieselgel 60). The column is eluted with chloroform-methanol (50:1) to obtain 2-pyridyl 3-chloropropyl sulfone (4 g) as colorless liquid.

NMR (90 MHz, CDCl$_3$): $\delta$2.10–2.50 (2H, m), 3.40–4.70 (4H, m), 7.50–7.70 (1H, m), 7.80–8.20 (2H, m), 8.70–8.80 (1H, m)

REFERENCE EXAMPLE 9

According to the same procedure as described in Reference Example 8, the following compounds are obtained:

1-Methyl-5-(2-chloroethyl)thio-1,2,3,4-tetrazole, colorless prisms (ether), m.p. 48°–49.5° C.

5-Methyl-2-(3-chloropropyl)thio-1,3,4-oxadiazole, colorless liuqid, $n_D^{26}=1.5147$ 5-Methyl-2-(3-chloropropyl)sulfinyl-1,3,4-oxadiazole, colorless liquid, $n_D^{26}=1.5279$

REFERENCE EXAMPLE 10

1-Methyl-5-mercapto-1,2,3,4-tetrazole (0.9 g) and 3-chloropropyl ethyl ketone ethylene ketal (1.3 g) are dissolved in acetone (50 ml). Potassium iodide (0.1 g) and potassium carbonate (1.1 g) are added to the solution and the mixture is refluxed for 6 hours. Acetone is distilled off and water is added to the residue. The mixture is extracted with chloroform and the chloroform solution is washed with saturated aqueous sodium chloride and dried over magnesium sulfate. The residue is purified by silica gel column chromatography (Kieselgel 60). The column is eluted with benzene-ether (5:1) to obtain 1-methyl-5-(4,4-ethylenedioxyhexyl)thio-1,2,3,4-tetrazole (0.6 g) as colorless liquid.

NMR (60 MHz, CDCl$_3$): $\delta$0.87 (3H, t, J=7 Hz), 1.30–2.00 (6H, m), 3.32 (2H, t, J=6 Hz), 3.90 (3H, s)

REFERENCE EXAMPLE 11

1-Methyl-5-mercapto-1,2,3,4-tetrazole (11.6 g) is dissolved in acetone (100 ml). Methyl 4-bromobutyrate (21.7 g) and potassium carbonate (15 g) are added to the solution and the mixture is refluxed for 4 hours. Acetone is distilled off under reduced pressure and water is added to the residue. The mixture is extracted with chloroform and the chloroform solution is washed with saturated aqueous sodium chloride and dried over magnesium sulfate. Chloroform is distilled off and the residue is subjected to silica gel column chromatography (Wakogel C-200). The column is eluted with benzene-ether (5:1) and the eluate is distilled under reduced pressure to obtain methyl 4-(1-methyl-1,2,3,4-tetrazol-5-yl)thiobutyrate (20 g) as colorless liquid, b.p. 175°–177° C./0.80 mmHg.

REFERENCE EXAMPLE 12

20% Hydrochloric acid (150 ml) is added to methyl 4-(1-methyl-1,2,3,4-tetrazol-5-yl)thiobutyrate (17 g) and the mixture is refluxed for 2 hours. After cooling, the reaction mixture is diluted with water and extracted with chloroform. The chloroform solution is washed with saturated aqueous sodium chloride and dried over magnesium sulfate. Chloroform is distilled off to obtain 4-(1-methyl-1,2,3,4-tetrazol-5-yl)thiobutyric acid as colorless liquid, $n_D^{26}=1.5133$

REFERENCE EXAMPLE 13

1-Methyl-5-mercapto-1,2,3,4-tetrazole (2.3 g) and 4-bromobutyronitrile (3.6 g) are dissolved in acetone (50 ml). Potassium carbonate (3 g) is added to the solution and the mixture is refluxed for 3 hours. Acetone is distilled off and water is added to the residue. The aqueous mixture is extracted with chloroform and the chloroform solution is washed with saturated aqueous sodium chloride and dried over magnesium sulfate. Chloroform is distilled off and the residue is purified by column chromatography (Wakogel C-200). The column is eluted with benzene-ether (5:1) to obtain 4-(1-methyl-1,2,3,4-tetrazol-5-yl)thiobutyronitirile (3.5 g).

Elemental analysis for C$_5$H$_9$N$_5$S: Calcd (%): C, 35.07; H, 5.30; N, 40.90. Found (%): C, 35.26; H, 5.41; N, 40.98.

REFERENCE EXAMPLE 14

Acetoanilide (20 g, 0.15 ml) is dissolved in carbon disulfide (110 ml) and 4-chlorobutyric acid chloride (37 g, 0.27 mol) is added to the solution. Aluminum chloride (60 g, 0.45 mol) is slowly added to the mixture with stirring at room temperature. The resulting mixture is refluxed for 30 minutes and allowed to stand at room temperature for 2.5 hours. Carbon disulfide is decanted off and the residue is poured into ice-conc. hydrochloric acid (20 ml). The precipitated crystals are collected by filtration and washed with water. The crude crystals thus obtained are suspended in ethanol. After stirring, the crystals are collected by filtration, washed with water and recrystallized from ethanol to obtain $\gamma$-chloro-4-acetamido butyrophenone (10 g) as colorless granules (ethanol), m.p. 157°–163° C.

REFERENCE EXAMPLE 15

Aluminum chloride (16 g, 0.12 mol) is suspended in carbon tetrachloride (80 ml) and 6-chlorohexanoyl chloride (20 g, 0.12 mol) is added dropwise to the suspension with ice-cooling. After completion of addition, the mixture is stirred for 15 minutes and benzene (7.8 g, 0.1 mol) is added dropwise to the mixture with ice-cooling. After stirring with ice-cooling for 1 hour, the mixture is poured into ice-hydrochloric acid and extracted with carbon tetrachloride. The carbon tetrachloride extract is washed with water, saturated aqueous sodium bicarbonate, water and then saturated aqueous sodium chloride and dried over anhydrous magnesium sulfate. The dried solution is distilled to obtain 5-chloropentyl phenyl ketone (7.3 g), b.p. 143°–150° C./0.5 mmHg.

REFERENCE EXAMPLE 16

Aluminum chloride (26.7 g) is added to nitrobenzene (20 ml) and 4-chlorobutyric acid chloride (15.5 g) is added dropwise to the mixture with ice-cooling. Naphthalene (12.8 g) is slowly added to the mixture with ice-cooling and stirring is continued at the same temperature for 30 minutes. After stirring at room temperature for additional 2 hours, the reaction mixture is poured into ice-hydrochloric acid and extracted with chloroform. The chloroform extract is washed with water, saturated aqueous sodium bicarbonate, water and then saturated aqueous sodium chloride and dried over anhydrous sodium sulfate. The dried solution is distilled. A fraction having b.p. 187°–191° C./1.6 mmHg is separated and purified by silica gel column chromatography. The product thus obtained is crystallized from hexane and then further recrystallized from hexane-petroleum ether to obtain 2-(4-chlorobutyryl)naphthalene (4.2 g) as colorless flakes, m.p. 43°–44° C.

REFERENCE EXAMPLE 17

Aluminum chloride (16 g, 0.12 mol) is suspended in carbon tetrachloride (80 ml). To the suspension is added dropwise 4-chlorovaleric acid chloride (18.6 g, 0.12 mol) with ice-cooling. The mixture is stirred for 15 minutes and benzene (7.8 g, 0.1 mol) is added dropwise to the mixture at below 5° C. Stirring is continued at the same temperature for 1 hour. The mixture is poured into ice-hydrochloric acid and extracted with chloroform. The chloroform layer is washed with water, saturated aqueous sodium bicarbonate, water and then saturated aqueous sodium chloride solution and dried over anhydrous magnesium sulfate. Chloroform is distilled off and the resulting crude crystals are recrystallized from hexane to obtain 4-chlorobutyl phenyl ketone (8.3 g) as colorless flakes, m.p. 49°–50° C.

REFERENCE EXAMPLE 18

According to the same procedure as described in above Reference Examples, the following compounds are obtained:

γ-Chloro-3,4-dimethoxybutyrophenone, pale yellow prisms (recrystallized from ligroin), m.p. 90°–92° C.

2-(γ-Chlorobutyryl)furan, NMR $\delta_{ppm}^{CDCl_3}$ 2.0–2.5 (2H, m), 3.00 (2H, t, J=7 Hz), 3.62 (2H, t, J=6 Hz), 6.47 (1H, m), 7.14 (1H, d, J=4 Hz), 7.51 (1H, d, J=2 Hz)

γ-Chloro-4-chlorobutyrophenone, colorless granules (recrystallized from methanol-water), m.p. 30° C.

γ-Chloro-4-ethylbutyrophenone, colorless liquid, b.p. 141°–148° C./0.9 mmHg

γ-Chloro-4-methoxybutyrophenone, colorless flakes (recrystallized from petroleum ether-ethyl acetate), m.p. 31° C.

2-(γ-Chlorobutyryl)pyrrole, NMR $\delta_{ppm}^{CDCl_3}$ 2.0–2.5 (2H, m), 2.96 (2H, t, J=7 Hz), 3.63 (2H, t, J=6 Hz), 6.25 (1H, m), 6.85–7.18 (2H, m), 10.2 (1H, br, 1H)

2-(γ-Chlorobutyryl)-5-methylthiophene, NMR $\delta_{ppm}^{CDCl_3}$ 2.0–2.5 (2H, m), 2.52 (3H, s), 3.04 (2H, t, J=7 Hz), 3.62 (2H, t, J=6 Hz), 6.74 (1H, d, J=4 Hz), 7.48 (1H, d, J=4 Hz)

3-(γ-Chlorobutyryl)-2,5-dimethylfuran, NMR $\delta_{ppm}^{CDCl_3}$ 2.0–2.5 (2H, m), 2.27 (3H, s), 2.54 (3H, s), 2.84 (2H, t, J=7 Hz), 3.16 (1H, s), 3.60 (2H, t, J=6 Hz)

2-(γ-Chlorobutyryl)-5-chlorothiophene, colorless liquid, b.p. 139°–144° C./0.75 mmHg 2-(γ-Chlorobutyryl)pyridine, colorless liquid, NMR $\delta_{ppm}^{CDCl_3}$ 2.23 (2H, m), 3.43 (2H, t, J=7 Hz), 3.68 (2H, t, J=7 Hz), 7.2–8.1 (3H, m), 8.63 (1H, d)

REFERENCE EXAMPLE 19

A Grignard reagent is prepared from magnesium (1.9 g), n-butyl bromide (11.2 g) and dried ether (80 ml) and a solution of 4-chlorobutyronitrile (7 g) in ether (15 ml) is added dropwise to the reagent with ice-cooling. The mixture is stirred at the same temperature for 2 hours and then at room temperature for additional 2 hours. 10% Hydrochloric acid is slowly added dropwise to the mixture with ice-cooling to decompose the product and to acidify the mixture to pH about 1. After stirring at room temperature for 1 hour, the mixture is extracted with ether. The ether layer is washed with saturated aqueous sodium bicarbonate and saturated aqueous sodium chloride and dried over magnesium sulfate. The solvent is distilled off and the residue is distilled to obtain 3-chloropropyl butyl ketone (1.6 g), b.p. 104°–106° C./30 mmHg.

REFERENCE EXAMPLE 20

According to the same procedure as described in Reference Example 12, the following compounds are obtained:

3-Chloropropyl cyclophentyl ketone, colorless liquid, b.p. 127°–137° C./22 mmHg

3-Chloropropyl benzyl ketone, colorless liquid, b.p. 108°–119° C./0.15 mmHg

3-Bromopropyl cyclohexyl ketone, NMR $\delta_{ppm}^{CDCl_3}$ 1.2–2.4 (11H, m), 2.0–2.5 (2H, m), 2.64 (2H, t, J=7 Hz), 3.44 (2H, t, J=6 Hz)

REFERENCE EXAMPLE 21

3-Chloropropyl ethyl ketone (1.5 g) is dissolved in ethylene glycol (10 ml) and methyl orthoformate (2 g) and p-toluenesulfonic acid (0.2 g) are added to the solution. The mixture is stirred at room temperature for 5 hours. After neutralization with sodium hydroxide, water is added to the mixture and the mixture is extracted with ether. The ether solution is washed with water and saturated aqueous sodium chloride and dried over magnesium sulfate. Ether is distilled off and the residue is distilled under reduced pressure to obtain 3-chloropropyl ethyl ketone ethylene ketal (1.3 g), b.p. 98°–102° C./33 mmHg.

REFERENCE EXAMPLE 22

According to the same procedure as described in Reference Example 21, the following compounds are obtained:

4-Chlorobutyrophenone ethylene ketal, NMR $\delta_{ppm}^{CDCl_3}$ 1.8–2.2 (4H, m), 3.43 (2H, t, J=6 Hz), 3.65–4.0 (4H, m), 7.1–7.5 (5H, m)

3-Bromopropyl cyclohexyl ketone ethylene ketal, NMR $\delta_{ppm}^{CDCl_3}$ 0.9–2.2 (15H, m), 3.40 (2H, t, J=6 Hz), 3.93 (4H, s)

3-Chloropropyl β-phenethyl ketone, b.p. 130°–139° C./0.25 mmHg 2-(4-Chlorobutyryl)-5-methoxycarbonylfuran, NMR $\delta_{ppm}^{CDCl_3}$ 2.0–2.5 (2H, m), 3.11 (2H, t, J=7 Hz), 3.63 (2H, t, J=6 Hz), 3.92 (3H, s), 7.1–7.3 (2H)

6-(4-Chlorobutyryl)-3,4-dihydrocarbostyril, pale yellow needles (acetone), m.p. 158°–160° C.

REFERENCE EXAMPLE 23

γ-Aminobutyric acid (15.5 g) is suspended in methanol (200 ml) and thionyl chloride (53.6 g) is added dropwise to the suspension with stirring and ice-cooling. The mixture is allowed to stand for overnight and methanol and thionyl chloride are distilled off. Benzene is added the mixture is concentrated under reduced pressure. The resulting residue (25 g) is dissolved in acetone (200 ml) and water (50 ml). Potassium carbonate (22.8 g) is added to the solution and then acetyl chloride (13 g) is added dropwise to the mixture with stirring and ice-cooling. Stirring is continued for 1 hour with ice-cooling and then at room temperature for additional 2 hours. Acetone is distilled off and water is added to the residue. The mixture is extracted with chloroform. The chloroform solution is washed with saturated aqueous sodium chloride and dried over magnesium sulfate. Chloroform is distilled off and the residue is distilled under reduced pressure to obtain methyl 4-acetamidobutyrate (1.6 g) as colorless liquid, b.p. 130°–132° C./0.7 mmHg.

EXAMPLE 1A

Methyl 4-acetamidobutyrate (8 g) is dissolved in benzene (80 ml). Phosphorus pentachloride (12 g, 0.055 mol) is added to the solution with stirring and ice-cooling. The mixture is stirring at room temperature for 1.5 hours and then concentrated to about ⅓ volume under reduced pressure. To the resulting iminochloride solution is added dropwise a solution of hydrogen azide in benzene (0.0173 mol/10 ml, 57.8 ml) with stirring and ice-cooling. The mixture is stirred at room temperature for 1 hour, allowed to stand for overnight and gently refluxed for 2 hours. The reaction mixture is concentrated and ice-water is added to the mixture. The mixture is extracted with chloroform. The chloroform solution is washed with water, dil. aqueous sodium hydroxide and then water and dried over magnesium sulfate. Chloroform is distilled off and the residue is purified by silica gel column chromatography (Wakogel C-200). The column is eluted with chloroform-methanol (50:1) to obtain methyl 4-(5-methyl-1,2,3,4-tetrazol-1-yl)butyrate (5.7 g) as colorless liquid.

NMR $\delta_{ppm}^{CDCl_3}$ 1.90–2.80 (4H, m), 2.58 (3H, s), 3.67 (3H, s), 4.35 (2H, t, J=7 Hz)

Elemental analysis for $C_7H_{12}N_4O_2$: Calcd (%): C, 45.64; H, 6.57; N, 30.42. Found (%): C, 45.79; H, 6.63; N, 30.56.

EXAMPLE 1B

According to the same manner as described in Example 1A, the following compounds are obtained:

Methyl 4-(5-phenyl-1,2,3,4-tetrazol-1-yl)butyrate, colorless prisms (ether), m.p. 52°–54° C.

Methyl 4-(5-butyl-1,2,3,4-tetrazol-1-yl)butyrate, pale yellow liquid, NMR $\delta_{ppm}^{CDCl_3}$ 0.97 (3H, t, J=7 Hz), 1.20–2.60 (6H, m), 2.85 (2H, t, J=7.5 Hz), 3.65 (3H, s), 4.34 (2H, t, J=6 Hz)

Methyl 5-(5-methyl-1,2,3,4-tetrazol-1-yl)valerate, pale yellow liquid, NMR $\delta_{ppm}^{CDCl_3}$ 1.50–2.30 (4H, m), 2.37 (2H, t, J=6 Hz), 2.54 (3H, s), 3.64 (3H, s), 4.28 (2H, t, J=7.5 Hz)

EXAMPLE 2A

20% Hydrochloric acid (30 ml) is added to methyl 4-(5-methyl-1,2,3,4-tetrazol-1-yl)butyrate (5.5 g) and the mixture is refluxed for 2 hour. The mixture is concentrated to dryness under reduced pressure. Acetone and benzene are added to the residue and water is removed by azeotropic distillation to obtain 4-(5-methyl-1,2,3,4-tetrazol-1-yl)butyric acid (4.7 g) as colorless liquid.

NMR $\delta_{ppm}^{d6-DMSO}$ 1.90–2.70 (4H, m), 2.58 (3H, s), 4.38 (2H, t, J=7 Hz), 10.10 (1H, s)

Elemental analysis for $C_6H_{10}N_4O_2$: Calcd (%): C, 42.35; H, 5.92; N, 32.93. Found (%): C, 42.18; H, 5.72; N, 33.24.

The liquid product thus obtained crystallizes on standing for 1 week and the crystalline product is further recrystallized from ether-acetone to obtain colorless needles, m.p. 71°–72.5° C.

EXAMPLE 2B

According to the same manner as described in Example 2A, the following compounds are obtained:

4-(5-Phenyl-1,2,3,4-tetrazol-1-yl)butyric acid, colorless prisms (ether), m.p. 134°–137° C.

4-(5-Butyl-1,2,3,4-tetrazol-1-yl)butyric acid, colorless prisms (acetone-ether), m.p. 77°–79° C.

5-(5-Methyl-1,2,3,4-tetrazol-1-yl)valeric acid, colorless needles (acetone), m.p. 109.5°–113° C.

EXAMPLE 3

4-(5-Methyl-1,2,3,4-tetrazol-1-yl)butyric acid (1.7 g) is dissolved in dimethylformamide (50 ml) and triethylamine (1.1 g) is added to the solution. Isobutyl chloroformate (1.5 g) is added dropwise to the mixture with stirring and ice-cooling and the mixture is stirred at room temperature for 30 minutes. Diethylamine (0.9 g) is added dropwise to the mixture with stirring at room temperature. The mixture is stirred for 3 hours. Dimethylformamide is distilled off and the residue is purified by silica gel column chromatography (silica gel made of Merck & Co.). The column is eluted with chloroform-methanol (50:1) to obtain N,N-diethyl-4-(5-methyl-1,2,3,4-tetrazol-1-yl)butyric acid amide (1.4 g), b.p. 190°–200° C. (bath temperature)/0.04 mmHg, $n_D^{25}$=1.4908.

Elemental analysis for $C_{10}H_{19}N_5O$: Calcd (%): C, 53.31; H, 8.50; N, 31.09. Found (%): C, 53.46; H, 8.61; N, 31.21.

EXAMPLE 4

According to the same manner as described in Example 3, the following compounds are obtained:

N-Ethyl-N-cyclohexyl-4-(5-methyl-1,2,3,4-tetrazol-1-yl)butyric acid amide, colorless liquid, $n_D^{18}$=1.5044

N-Butyl-4-(5-methyl-1,2,3,4-tetrazol-1-yl)butyric acid amide, colorless needles, m.p. 86°–88° C. (ethyl acetate-hexane)

N,N-Dipropyl-4-(5-methyl-1,2,3,4-tetrazol-1-yl)butyric acid amide, pale yellow liquid, $n_D^{22.5}$=1.4855

N,N-Dimethyl-4-(5-methyl-1,2,3,4-tetrazol-1-yl)butyric acid amide, colorless prisms (hexane-ethyl acetate), m.p. 64°–64.5° C.

N,N-Dibutyl-4-(5-methyl-1,2,3,4-tetrazol-1-yl)butyric acid amide, brown liquid, $n_D^{15}$=1.4871

N-Hexyl-4-(5-methyl-1,2,3,4-tetrazol-1-yl)-butyric acid amide, colorless needles (hexane-ethyl acetate), m.p. 92°–93° C.

N,N-Diethyl-5-(5-methyl-1,2,3,4-tetrazol-1-yl)valeric acid amide, pale yellow liquid, $n_D^{13}$=1.4940

N-(4-Nitrophenyl)-4-(5-methyl-1,2,3,4-tetrazol-1-yl)butyric acid amide, pale yellow flakes (methanol-water), m.p. 167°–168° C.

N-Ethyl-N-cyclohexyl-4-(5-phenyl-1,2,3,4-tetrazol-1-yl)butyric acid amide, colorless granules (ethyl acetate-hexane), m.p. 68°–71.5° C.

N-tert-Butyl-N-benzyl-4-(5-methyl-1,2,3,4-tetrazol-1-yl)butyric acid amide, brown liquid, $n_D^{17.5}$=1.5400

N-[(2-Furyl)methyl]-4-(5-methyl-1,2,3,4-tetrazol-1-yl)butyric acid amide, colorless needles (hexane-ethyl acetate), m.p. 90.5°–91.5° C.

N-Ethyl-N-(2-hydroxycyclohexyl)-4-(5-methyl-1,2,3,4-tetrazol-1-yl)butyric acid amide, pale yellow liquid, $n_D^{18}$=1.5121

N-Cyclohexyl-N-(2-hydroxyethyl)-4-(5-methyl-1,2,3,4-tetrazol-1-yl)butyric acid amide, pale yellow liquid, $n_D^{17.5}$=1.5120

EXAMPLE 5

Thionyl chloride (10 ml) is added to 4-(5-methyl-1,2,3,4-tetrazol-1-yl)butyric acid (2 g) and the mixture is refluxed for 1 hour. Excess thionyl chloride is distilled off under reduced pressure. Dried benzene is added to the residue and trace amount of thionyl chloride is removed by azeotropic distillation. The residue is dissolved in dried benzene (50 ml). 4-Methoxyaniline (3 g) is added dropwise to the solution with stirring and ice-cooling and the mixture is stirred at room temperature for 1 hour. Benzene is added to the reaction mixture and the mixture is washed with dil. hydrochloric acid, saturated aqueous sodium bicarbonate and then saturated aqueous sodium chloride and dried over sodium sulfate. Benzene is distilled off and the residue is recrystallized from ethanol to obtain N-(4-methoxyphenyl)-4-(5-methyl-1,2,3,4-tetrazol-1-yl)butyric acid amide (2.4 g) as colorless prisms, m.p. 132°-134° C.

EXAMPLE 6

According to the same manner as described in Example 5, the following compounds are obtained:

N-(4-Methoxycyclohexyl)-4-(5-methyl-1,2,3,4-tetrazol-1-yl)butyric acid amide, brown liquid, NMR $\delta_{ppm}^{CDCl_3}$ 1.40-2.00 (8H, m), 2.00-2.40 (4H, m), 2.56 (3H, s), 3.27 (3H, s), 3.20-3.40 (1H, m), 3.50-4.00 (1H, m), 4.35 (2H, t, J=6 Hz), 5.60-6.00 (1H, m)

N,N-Diethyl-4-(5-methyl-1,2,3,4-tetrazol-1-yl)butyric acid amide, colorless liquid, b.p. 190°-200° C. (bath temperature)/0.04 mmHg, $n_D^{25}$=1.4908

5-Methyl-1-[3-(4-methyl-1-piperazinylcarbonyl)propyl]-1,2,3,4-tetrazole, brown liquid, $n_D^{20}$=1.5085

N-(2-Furyl)methyl-4-(5-methyl-1,2,3,4-tetrazol-1-yl)butyric acid amide, colorless needles (hexane-ethyl acetate), m.p. 90.5°-91.5° C.

N-[2-(3,4-Dimethoxyphenyl)ethyl]-4-(5-methyl-1,2,3,4-tetrazol-1-yl)butyric acid amide, colorless needles (hexane-ethyl acetate), m.p. 75°-76° C.

N-(4-Dimethylaminophenyl)-4-(5-methyl-1,2,3,4-tetrazol-1-yl)butyric acid amide monohydrate, pale yellow powder (hexane-ethyl acetate), m.p. 139.5°-140.5° C.

N-(2-Methyl-3-chlorophenyl)-4(5-methyl-1,2,3,4-tetrazol-1-yl)butyric acid amide, colorless needles (hexane-ethyl acetate), m.p. 116°-117° C.

N-(4-Nitrophenyl)-4-(5-methyl-1,2,3,4-tetrazol-1-yl)butyric acid amide, pale yellow flakes (methanol-water), m.p. 167°-168° C.

N-(2-Thiazolyl)-4-(5-methyl-1,2,3,4-tetrazol-1-yl)butyric acid amide, pale yellow needles (ethanol), m.p. 200°-202° C.

N-(2-Carboxyphenyl)-4-(5-methyl-1,2,3,4-tetrazol-1-yl)butyric acid amide, pale yellow powder (hexane-ethyl acetate), m.p. 176°-178° C.

N-Ethyl-N-(2-hydroxycyclohexyl)-4-(5-methyl-1,2,3,4-tetrazol-1-yl)butyric acid amide, pale yellow liquid, $n_D^{18}$=1.5121

N-Cyclohexyl-N-(2-hydroxyethyl)-4-(5-methyl-1,2,3,4-tetrazol-1-yl)butyric acid amide, pale yellow liquid, $n_D^{17.5}$=1.5120

5-Methyl-1-(3-morpholinocarbonylpropyl)-1,2,3,4-tetrazole, brown liquid, $n_D^{19}$=1.5130

5-Methyl-1-[3-(1-piperidylcarbonyl)propyl]-1,2,3,4-tetrazole, brown liquid, $n_D^{17}$=1.5162

N-tert-Butyl-N-benzyl-4-(5-methyl-1,2,3,4-tetrazol-1-yl)butyric acid amide, brown liquid, $n_D^{17.5}$=1.5400

N-Ethyl-N-(3-pyridyl)methyl-4-(5-methyl-1,2,3,4-tetrazol-1-yl)butyric acid amide, brown liquid, $n_D^{19}$=1.5429

N,N-Diethyl-5-(5-methyl-1,2,3,4-tetrazol-1-yl)valeric acid amide, pale yellow liquid, $n_D^{13}$=1.4940

N,N-Diethyl-4-(5-butyl-1,2,3,4-tetrazol-1-yl)butyric acid amide, colorless liquid, $n_D^{14.5}$=1.4895

N,N-Diethyl-4-(5-phenyl-1,2,3,4-tetrazol-1-yl)butyric acid amide, colorless prisms (ethyl acetate-hexane), m.p. 62.5°-63.5° C.

EXAMPLE 7

1-Methyl-4-(4-chlorobutyryl)piperazine (6.2 g) is dissolved in dry benzene (50 ml). To the solution are added 5-methyl-1,2,3,4-tetrazole (2.6 g), potassium carbonate (4.5 g) and sodium iodide (0.2 g) and the mixture is refluxed for 5 hours. The reaction mixture is diluted with benzene, washed with water, saturated aqueous sodium bicarbonate and then saturated aqueous sodium chloride and dried over sodium sulfate. Benzene is distilled off and the residue is purified by column chromatography (Wakogel C-200). The column is eluted with benzene-chloroform (4:1) to obtain 5-methyl-1-[3-(4-methyl-1-piperazinyl)carbonyl]propyl-1,2,3,4-tetrazole (4.2 g) as brown liquid, $n_D^{20}$=1.5085.

EXAMPLE 8

According to the same manner as described in Example 7, the following compounds are obtained:

N-(4-Methoxycyclohexyl)-4-(5-methyl-1,2,3,4-tetrazol-1-yl)butyric acid amide, brown liquid, NMR $\delta_{ppm}^{CDCl_3}$ 1.40-2.00 (8H, m), 2.00-2.40 (4H, m), 2.56 (3H, s), 3.27 (3H, s), 3.20-3.40 (1H, m), 3.50-4.00 (1H, m), 4.35 (2H, t, J=6 Hz), 5.60-6.00 (1H, m)

N,N-Diethyl-4-(5-methyl-1,2,3,4-tetrazol-1-yl)butyric acid amide, colorless liquid, b.p. 190°-200° C. (bath temperature)/0.04 mmHg, $n_D^{25}$=1.4908

N-(4-Methoxyphenyl)-4-(5-methyl-1,2,3,4-tetrazol-1-yl)butyric acid amide, colorless prisms (ethanol), m.p. 132°-134° C.

N-(2-Furyl)methyl-4-(5-methyl-1,2,3,4-tetrazol-1-yl)butyric acid amide, colorless needles (hexane-ethyl acetate), m.p. 90.5°-91.5° C.

N-[2-(3,4-Dimethoxyphenyl)ethyl]-4-(5-methyl-1,2,3,4-tetrazol-1-yl)butyric acid amide, colorless needles (hexane-ethyl acetate), m.p. 75°-76° C.

N-(4-Dimethylaminophenyl)-4-(5-methyl-1,2,3,4-tetrazol-1-yl)butyric acid amide monohydrate, pale yellow powder (hexane-ethyl acetate), m.p. 139.5°-140.5° C.

N-(2-Methyl-3-chlorophenyl)-4-(5-methyl-1,2,3,4-tetrazol-1-yl)butyric acid amide, colorless needles (hexane-ethyl acetate), m.p. 116°-117° C.

N-(4-Nitrophenyl)-4-(5-methyl-1,2,3,4-tetrazol-1-yl)butyric acid amide, pale yellow flakes (methanol-water), m.p. 167°-168° C.

N-(2-Thiazolyl)-4-(5-methyl-1,2,3,4-tetrazol-1-yl)butyric acid amide, pale yellow needles (ethanol), m.p. 200°-202° C.

N-(2-Carboxyphenyl)-4-(5-methyl-1,2,3,4-tetrazol-1-yl)butyric acid amide, pale yellow powder (hexane-ethyl acetate), m.p. 176°-178° C.

N-Ethyl-N-(2-hydroxycyclohexyl)-4-(5-methyl-1,2,3,4-tetrazol-1-yl)butyric acid amide, pale yellow liquid, $n_D^{18}$=1.5121

N-Cyclohexyl-N-(2-hydroxyethyl)-4-(5-methyl-1,2,3,4-tetrazol-1-yl)butyric acid amide, pale yellow liquid, $n_D^{17.5}$=1.5120

5-Methyl-1-(3-morphlinocarbonylpropyl)-1,2,3,4-tetrazole, brown liquid, $n_D^{19}=1.5130$ 5-Methyl-1-[3-(1-piperidylcarbonyl)propyl]-1,2,3,4-tetrazole, brown liquid, $n_D^{17}=1.5162$ N-tert-Butyl-N-benzyl-4-(5-methyl-1,2,3,4-tetrazol-1-yl)butyric acid amide, brown liquid, $n_D^{17.5}=1.5400$ N-Ethyl-N-(3-pyridyl)methyl-4-(5-methyl-1,2,3,4-tetrazol-1-yl)butyric acid amide, brown liquid, $n_D^{19}=1.5429$ N,N-Diethyl-5-(5-methyl-1,2,3,4-tetrazol-1-yl)valeric acid amide, brown liquid, $n_D^{13}=1.4940$ N,N-Diethyl-4-(5-butyl-1,2,3,4-tetrazol-1-yl)butyric acid amide, colorless liquid, $n_D^{14.5}=1.4895$ N,N-Diethyl-4-(5-phenyl-1,2,3,4-tetrazol-1-yl)butyric acid amide, colorless prisms (ethyl acetate-hexane), m.p. 62.5°–63.5° C.

N-Butyl-4-(5-methyl-1,2,3,4-tetrazol-1-yl)butyric acid amide, colorless needles (ethyl acetate-hexane), m.p. 86°–88° C.

N,N-Dipropyl-4-(5-methyl-1,2,3,4-tetrazol-1-yl)butyric acid amide, pale yellow liquid, $n_D^{22.5}=1.4855$ N,N-Dimethyl-4-(5-methyl-1,2,3,4-tetrazol-1-yl)butyric acid amide, colorless prisms, (hexane-ethyl acetate), m.p. 64°–64.5° C.

Methyl 4-(5-methyl-1,2,3,4-tetrazol-1-yl)butyrate, colorless liquid, NMR $\delta_{ppm}^{CDCl_3}$ 1.90–2.80 (4H, m), 2.58 (3H, s), 3.67 (3H, s), 4.35 (2H, t, J=7 Hz)

4-(5-Methyl-1,2,3,4-tetrazol-1-butyric acid, colorless liquid, NMR $\delta_{ppm}^{d6-DMSO}$ 1.90–2.70 (4H, m), 2.58 (3H, s), 4.38 (2H, t, J=7 Hz), 10.10 (1H, s)

N-Ethyl-N-cyclohexyl-4-(5-methyl-1,2,3,4-tetrazol-1-yl)butyric acid amide, colorless liquid, $n_D^{18}=1.5044$ N,N-Dibutyl-4-(5-methyl-1,2,3,4-tetrazol-1-yl)butyric acid amide, brown liquid, $n_D^{15}=1.4871$ N-Hexyl-4-(5-methyl-1,2,3,4-tetrazol-1-yl)butyric acid amide, colorless needles (hexane-ethyl acetate), m.p. 92°–93° C.

EXAMPLE 9

1-Methyl-5-mercapto-1,2,3,4-tetrazole (1.2 g) is dissolved in acetone (50 ml). To the solution are added 3-bromopropyl phenyl sulfide (2.5 g) and potassium carbonate (1.5 g) and the mixture is refluxed for 4 hours. Acetone is distilled off and water is added to the residue. The mixture is extracted with chloroform. The chloroform solution is washed with saturated aqueous sodium chloride and dried over magnesium sulfate. Chloroform is distilled off and the residue is purified by column chromatography (Kieselgel 60). The column is eluted with benzenechloroform (3:2) to obtain 1-methyl-5-(3-phenylthiopropyl)thio-1,2,3,4-tetrazole (1.8 g) as colorless liquid, $n_D^{18}=1.6008$.

Elemental analysis for $C_{11}H_{14}N_4S_2$: Calcd (%): C, 49.60; H, 5.30; N, 21.03. Found (%): C, 49.70; H, 5.13; N, 20.94.

EXAMPLE 10

According to the same manner as described in Example 9, the following compounds are obtained:

1-Methyl-5-(3-cyclohexylthiopropyl)thio-1,2,3,4-tetrazole, colorless liquid, $n_D^{18}=1.5433$ 1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°–128.5° C.

1-Methyl-5-[3-(1-cyclohexyl-1,2,3,4-tetrazol-5-yl)thiopropyl]thio-1,2,3,4-tetrazole, pale yellow liquid, $n_D^{18}=1.5653$ 1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°–82° C.

1-Methyl-2-[3-(1-methylimidazol-2-yl)thiopropyl]thio-1,2,3,4-tetrazole, colorless needles (recrystallized from ether), m.p. 59.5°–60.5° C.

1-Methyl-5-[3-(2-pyridyl)thiopropyl]thio-1,2,3,4-tetrazole, pale yellow liquid, $n_D^{18}=1.6022$ 1-Methyl-5-[2-(1-methyl-1,2,3,4-tetrazol-5-yl)thioethyl]thio-1,2,3,4-tetrazole, colorless prisms (recrystallized from ethanol-chloroform), m.p. 145°–147° C.

1-Methyl-5-[3-methyl-3-(5-methyl-1,3,4-oxadiazol-2-yl)thiopropyl]thio-1,2,3,4-tetrazole, colorless liquid, $n_D^{22.5}=1.5553$ 1-Methyl-5-[(1-methyl-1,2,3,4-tetrazol-5-yl)-thiomethyl]thio-1,2,3,4-tetrazole, colorless flakes (recrystallized from methanol-chloroform), m.p. 156°–159° C.

1-Methyl-5-[3-(5-methyl-1,3,4-oxadiazol-2-yl)sulfinylpropyl]thio-1,2,3,4-tetrazole, pale yellow liquid, $n_D^{23.5}=1.5598$ 1-Cyclohexyl-5-(3-ethylthiopropyl)thio-1,2,3,4-tetrazole, colorless liquid, $n_D^{14}=1.5433$ 1-Methyl-5-B [3-(1-methyl-1,2,3,4-tetrazol-5-yl)thiopropyl]thio-1,2,3,4-tetrazole, colorless prisms (recrystallized from ethanol), m.p. 141.5°–143.5° C.

1-Methyl-5-[4-(1-methyl-1,2,3,4-tetrazol-5-yl)thiobutyl]thio-1,2,3,4-tetrazole, colorless needles (recrystallized from ethanol), m.p. 122°–123° C.

EXAMPLE 11

1-Methyl-5-mercapto-1,2,3,4-tetrazole (1.2 g) is dissolved in acetone (50 ml). To the solution are added 2-(3-chloropropyl)thiopyridine (2.0 g) and potassium carbonate (1.5 g) and the mixture is refluxed for 4 hours. Acetone is distilled off and water is added to the residue. The mixture is extracted with chloroform. The chloroform solution is washed with saturated aqueous sodium chloride and dried over magnesium sulfate. Chloroform is distilled off and the residue is purified by column chromatography (Kieselgel 60). The column is eluted with chloroform-methanol and the product is recrystallized from ethanol to obtain 1-methyl-5-[2-(2-pyridyl)thioethyl]thio-1,2,3,4-tetrazole (1.5 g) as colorless prisms, m.p. 77°–79.5° C.

Elemental analysis for $C_9H_{11}N_5S_2$: Calcd (%): C, 42.67; H, 4.38; N, 27.64. Found (%): C, 42.43; H, 4.30; N, 27.53.

EXAMPLE 12

According to the same manner as described in Example 11, the following compounds are obtained:

1-Methyl-5-[4-(2-pyridyl)thiobutyl]thio-1,2,3,4-tetrazole, pale yellow prisms, m.p. 49°–51.5° C. (ethanol-water)

1-Methyl-5-[5-(2-pyridyl)thiopentyl]thio-1,2,3,4-tetrazole, colorless liquid, $n_D^{19}=1.5853$ 1-Methyl-5-[6-(2-pyridyl)thiohexyl]thio-1,2,3,4-tetrazole, colorless prisms, m.p. 58°–60° C. (ethanol)

1-Methyl-5-[3-(3-hydroxy-2-pyridyl)thiopropyl]thio-1,2,3,4-tetrazole, pale yellow granules, m.p. 87.5°–88.5° C. (hexane-ethyl acetate)

1-Methyl-5-[3-(4-methyl-2-pyrimidyl)thiopropyl]-thio-1,2,3,4-tetrazole, colorless liquid, $n_D^{25.5}=1.5853$ 1-Methyl-2-[4-(1-methyl-1,2,3,4-tetrazol-5-yl)thiobutyl]isothiourea hydrobromide, white powder (acetone), m.p. 116.5°–118° C. (dec.)

1-Methyl-5-[3-[2-benzimidazolyl)thiopropyl]thio-1,2,3,4-tetrazole, colorless needles (ethanol), m.p. 137°-139° C.

1-Methyl-5-[3-(3,5-di-tert-butyl-4-hydroxyphenyl)thiopropyl]thio-1,2,3,4-tetrazole, pale yellow needles (methanol-water), m.p. 76°-77° C.

1-Methyl-5-[3-(5-amino-1,3,4-thiadiazol-2-yl)thiopropyl]thio-1,2,3,4-tetrazole, colorless prisms (ethanol), m.p. 120.5°-122° C.

1-Methyl-5-[3-(5-methyl-1,3,4-oxadiazol-2-yl)thiopropyl]thio-1,2,3,4-tetrazole, colorless liquid, $n_D^{25.5}=1.5644$ 1-Methyl-5-[3-(β-naphthyl)thiopropyl]thio-1,2,3,4-tetrazole, colorless needles (ethanol), m.p. 56°-58° C.

1-Methyl-5-[3-(2-quinolyl)thiopropyl]thio-1,2,3,4-tetrazole, pale yellow needles (methanol), m.p. 87°-89° C.

1-Methyl-5-(4-phenylthiobutyl)thio-1,2,3,4-tetrazole, colorless columns (ethanol), m.p. 51.5°-53° C.

1-Methyl-5-[4-(2-carboxyphenyl)thiobutyl]thio-1,2,3,4-tetrazole, pale yellow prisms (ethanol), m.p. 143.5°-144.5° C.

1-Methyl-5-[4-(2-methylphenyl)thiobutyl]thio-1,2,3,4-tetrazole, colorless liquid, $n_D^{29}=1.5786$ 1-Methyl-5-[4-(2-aminophenyl)thiobutyl]thio-1,2,3,4-tetrazole, yellow liquid, $n_D^{29}=1.5961$ 1-Methyl-5-[4-(4-chlorophenyl)thiobutyl]thio-1,2,3,4-tetrazole, colorless liquid, $n_D^{29}=1.5971$ 1-Methyl-5-[3-(2-furylmethyl)thiopropyl]thio-1,2,3,4-tetrazole, brown liquid, $n_D^{26.5}=1.5641$ 1-Methyl-5-(3-benzylthiopropyl)thio-1,2,3,4-tetrazole, colorless liquid, $n_D^{26.5}=1.5856$ 1-Methyl-5-[3-(4-chlorobenzyl)thiopropyl]thio-1,2,3,4-tetrazole, colorless liquid, $n_D^{29}=1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°-77° C.

1-Methyl-5-[3-(quinazolin-4-on-2-yl)thiopropyl]thio-1,2,3,4-tetrazole, colorless flakes (ethanol-hexane), m.p. 132.5°-134.5° C.

1-Methyl-5-[4-(3H,4H-1,3,4-benzotriazepin-5-on-2-yl)thiobutyl]thio-1,2,3,4-tetrazole, colorless prisms, m.p. 94°-95° C. (methanol)

1-Methyl-5-(3-ethylthiopropyl)thio-1,2,3,4-tetrazole, colorless liquid, $n_D^{29}=1.5385$ 1-Methyl-5-(3-n-butylthiopropyl)thio-1,2,3,4-tetrazole, yellow liquid, $n_D^{29}=1.5192$ 1-Methyl-5-(3-cycloheptylthiopropyl)thio-1,2,3,4-tetrazole, pale yellow liquid, $n_D^{29}=1.5469$ 1-Methyl-5-[3-(2-pyridylmethyl)thiopropyl]thio-1,2,3,4-tetrazole, brown liquid, $n_D^{29}=1.5820$ 1-Methyl-5-[3-(4-methyl-2-thiazolyl)thiopropyl]thio-1,2,3,4-tetrazole, colorless liquid, $n_D^{29}=1.5919$ 1-Methyl-5-[3-(4-pyridyl)thiopropyl]thio-1,2,3,4-tetrazole, pale yellow liquid, $n_D^{26}=1.6017$ 1-Methyl-5-[3-(5-nitro-2-pyridyl)thiopropyl]thio-1,2,3,4-tetrazole, pale brown liquid, $n_D^{29}=1.6289$ 1-Methyl-5-[3-(2-amino-4-methyl-6-pyrimidyl)thiopropyl]thio-1,2,3,4-tetrazole, colorless powder (methanol), m.p. 119°-120° C.

1-Methyl-5-[2-(2-furylmethyl)thioethyl]thio-1,2,3,4-tetrazole, pale brown liquid, $n_D^{29}=1.5711$ 1-Methyl-5-{3-[(2-amino-4-thiazolyl)methyl]thiopropyl}thio-1,2,3,4-tetrazole, yellow prisms (methanol-water), m.p. 117°-118.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°-89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°-90.5° C.

1-Methyl-5-[5-(1-methyl-1,2,3,4-tetrazol-5-yl)thiopentyl]thio-1,2,3,4-tetrazole, colorless prisms (ethanol), m.p. 64°-65° C.

1-Methyl-5-[6-(1-methyl-1,2,3,4-tetrazol-5-yl)thiohexyl]thio-1,2,3,4-tetrazole, colorless prisms (acetone), m.p. 91°-93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°-89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°-70.5° C.

1-Methyl-5-[2-methyl-3-(2-pyridyl)thiopropyl]thio-1,2,3,4-tetrazole, pale yellow liquid, $n_D^{25.5}=1.5936$ 1-Methyl-5-[4-(4-methoxyphenyl)thiobutyl]thio-1,2,3,4-tetrazole, colorless liquid, NMR (90 MHz, CDCl₃) δ1.50–2.20 (4H, m), 2.83 (2H, t, J=6 Hz), 3.30 (2H, t, J=6 Hz), 3.77 (3H, s), 3.87 (3H, s), 6.82 (2H, d, J=9 Hz), 7.32 (2H, d, J=9 Hz)

EXAMPLE 13

1-Methyl-5-mercapto-1,2,3,4-tetrazole (1.2 g) is dissolved in acetone (50 ml). To the solution are added 1-methyl-5-(8-chlorooctyl)thio-1,2,3,4-tetrazole (4.1 g) and potassium carbonate (1.5 g) and the mixture is refluxed for 4 hours. Acetone is distilled off and water is added to the residue. The mixture is extracted with chloroform. The chloroform solution is washed with saturated aqueous sodium chloride and dried over magnesium sulfate. Chloroform is distilled off and the residue is recrystallized from ethyl acetate-hexane to obtain 1-methyl-5-[8-(1-methyl-1,2,3,4-tetrazol-5-yl)thiooctyl]thio-1,2,3,4-tetrazole (2.0 g) as colorless needles, m.p. 52°-54° C.

EXAMPLE 14

According to the same manner as described in Example 13, the following compounds are obtained:

1-Methyl-5-[3-(3-methoxy-2-pyridyl)thiopropyl]thio-1,2,3,4-tetrazole, colorless needles (ethanol), m.p. 53.5°-55° C.

1-Methyl-5-[3-(2aminothiazol-5-yl)methylthiopropyl]thio-1,2,3,4-tetrazole, yellow prisms (methanol-water), m.p. 117°-118.5° C.

EXAMPLE 15

1-Methyl-5-chloro-1,2,3,4-tetrazole (1.18 g) and thiourea (0.8 g) are dissolved in ethanol (50 ml) and the solution is refluxed for 3 hours. After cooling, precipated crystals are filtered off and dried. The crystals are dissolved in ethanol (50 ml) and 2-(2-chloroethyl)thiopyridine (1.7 g) and 10% aqueous sodium hydroxide (5 ml) are added to the solution. The mixture is refluxed for 3 hours. Ethanol is distilled off and water is added to the residue. The mixture is extracted with chloroform and the extract is washed with saturated aqueous sodium chloride and dried over magnesium sulfate. Chloroform is distilled off and the residue is purified by column chromatography (Kieselgel 60, eluant: Chloroform). The product is recrystallized from ethanol to obtain 1-methyl-5-[2-(2-pyridyl)thioethyl]thio-1,2,3,4-tetrazole, (0.7 g) as colorless prisms, m.p. 77°-79.5° C.

Elemental analysis for $C_9H_{11}N_5S_2$: Calcd (%): C, 42.67; H, 4.38; N, 27.64. Found (%): C, 42.53; H, 4.29; N, 27.38.

EXAMPLE 16

According to the same manner as described in Example 15, the following compounds are obtained:

1-Methyl-5-[4-(2-pyridyl)thiobutyl]thio-1,2,3,4-tetrazole, pale yellow prisms, m.p. 49°–51.5° C. (ethanol-water)

1-Methyl-5-[5-(2-pyridyl)thiopentyl]thio-1,2,3,4-tetrazole, colorless liquid, $n_D^{19} = 1.5853$ 1-Methyl-5-[6-(2-pyridyl)thiohexyl]thio-1,2,3,4-tetrazole, colorless prisms, m.p. 58°–60° C. (ethanol)

1-Methyl-5-[3-(4-methyl-2-pyrimidyl)thiopropyl]thio-1,2,3,4-tetrazole, colorless liquid, $n_D^{25.5} = 1.5853$ 1-Methyl-5-[3-[2-benzimidazolyl)thiopropyl]thio-1,2,3,4-tetrazole, colorless needles (ethanol), m.p. 137°–139° C.

1-Methyl-5-[3-(3,5-di-tert-butyl-4-hydroxyphenyl)thiopropyl]thio-1,2,3,4-tetrazole, pale yellow needles (methanol-water), m.p. 76°–77° C.

1-Methyl-5-[3-(5-amino-1,3,4-thiadiazol-2-yl)thiopropyl]thio-1,2,3,4-tetrazole, colorless prisms (ethanol), m.p. 120.5°–122° C.

1-Methyl-5-[3-(5-methyl-1,3,4-oxadiazol-2-yl)thiopropyl]thio-1,2,3,4-tetrazole, colorless liquid, $n_D^{25.5} = 1.5644$ 1-Methyl-5-[3-(β-naphthyl)thiopropyl]thio-1,2,3,4-tetrazole, colorless needles (ethanol), m.p. 56°–58° C.

1-Methyl-5-[3-(2-quinolyl)thiopropyl]thio-1,2,3,4-tetrazole, pale yellow needles (methanol), m.p. 87°–89° C.

1-Methyl-5-(4-phenylthiobutyl)thio-1,2,3,4-tetrazole, colorless prisms (ethanol), m.p. 51.5°–53° C.

1-Methyl-5-[4-(2-carboxyphenyl)thiobutyl]thio-1,2,3,4-tetrazole, pale yellow prisms (ethanol), m.p. 143.5°–144.5° C.

1-Methyl-5-[4-(2-methylphenyl)thiobutyl]thio-1,2,3,4-tetrazole, colorless liquid, $n_D^{29} = 1.5786$ 1-Methyl-5-[4-(2-aminophenyl)thiobutyl]thio-1,2,3,4-tetrazole, yellow liquid, $n_D^{29} = 1.5961$ 1-Methyl-5-[4-(4-chlorophenyl)thiobutyl]thio-1,2,3,4-tetrazole, colorless liquid, $n_D^{29} = 1.5971$ 1-Methyl-5-[3-(2-furylmethyl)thiopropyl]thio-1,2,3,4-tetrazole, brown liquid, $n_D^{26.5} = 1.5641$ 1-Methyl-5-(3-benzylthiopropyl)thio-1,2,3,4-tetrazole, colorless liquid, $n_D^{26.5} = 1.5856$ 1-Methyl-5-[3-(4-chlorobenzyl)thiopropyl]thio-1,2,3,4-tetrazole, colorless liquid, $n_D^{29} = 1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°–77° C.

1-Methyl-5-[3-(quinazolin-4-one-2-yl)thiopropyl]thio-1,2,3,4-tetrazole, colorless flakes (ethanol-hexane), m.p. 132.5°–134.5° C.

1-Methyl-5-[4-(3H,4H-1,3,4-benzotriazepin-5-on-2-yl)thiobutyl]thio-1,2,3,4-tetrazole, colorless prisms, m.p. 94°–95° C. (methanol)

1-Methyl-5-(3-ethylthiopropyl)thio-1,2,3,4-tetrazole, colorless liquid, $n_D^{29} = 1.5385$ 1-Methyl-5-(3-n-butylthiopropyl)thio-1,2,3,4-tetrazole, yellow liquid, $n_D^{29} = 1.5192$ 1-Methyl-5-(3-cycloheptylthiopropyl)thio-1,2,3,4-tetrazole, pale yellow liquid, $n_D^{29} = 1.5469$ 1-Methyl-5-[3-(2-pyridylmethyl)thiopropyl]thio-1,2,3,4-tetrazole, brown liquid, $n_D^{29} = 1.5820$ 1-Methyl-5-[3-(4-methyl-2-thiazolyl)thiopropyl]thio-1,2,3,4-tetrazole, colorless liquid, $n_D^{29} = 1.5919$ 1-Methyl-5-[3-(4-pyridyl)thiopropyl]thio-1,2,3,4-tetrazole, pale yellow liquid, $n_D^{26} = 1.6017$ 1-Methyl-5-[3-(5-nitro-2-pyridyl)thiopropyl]thio-1,2,3,4-tetrazole, pale brown liquid, $n_D^{29} = 1.6289$ 1-Methyl-5-[3-(2-amino-4-methyl-6-pyrimidyl)thiopropyl]thio-1,2,3,4-tetrazole, colorless powder (methanol), m.p. 119°–120° C.

1-Methyl-5-[2-(2-furylmethyl)thioethyl]thio-1,2,3,4-tetrazole, pale brown liquid, $n_D^{29} = 1.5711$ 1-Methyl-5{3-[(2-amino-4-thiazolyl)methyl]thiopropyl}thio-1,2,3,4-tetrazole, yellow prisms (methanol-water), m.p. 117°–118.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°–89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°–90.5° C.

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

1-Methyl-5-[2-methyl-3-(2-pyridyl)thiopropyl]thio-1,2,3,4-tetrazole, pale yellow liquid, $n_D^{25.5} = 1.5936$ 1-Methyl-5-[4-(4-methoxyphenyl)thiobutyl]thio-1,2,3,4-tetrazole, colorless liquid, NMR (90 MHz, CDCl₃) δ1.50–2.20 (4H, m), 2.83 (2H, t, J=6 Hz), 3.30 (2H, t, J=6 Hz), 3.77 (3H, s), 3.87 (3H, s), 6.82 (2H, d, J=9 Hz), 7.32 (2H, d, J=9 Hz)

1-Methyl-5-(3-phenylthiopropyl)thio-1,2,3,4-tetrazole, colorless liquid, $n_D^{18} = 1.6008$ 1-Methyl-5-(3-cyclohexylthiopropyl)thio-1,2,3,4-tetrazole, colorless liquid, $n_D^{18} = 1.5433$ 1-Methyl-5-[3-(2-pyridyl)thiopropyl]thio-1,2,3,4-tetrazole, pale yellow liquid, $n_D^{18} = 1.6022$ 1-Cyclohexyl-5-(3-ethylthiopropyl)thio-1,2,3,4-tetrazole, colorless liquid, $n_D^{14} = 1.5433$ 1-Methyl-5-[3-(1-methyl-1,2,3,4-tetrazol-5-yl)thiopropyl]thio-1,2,3,4-tetrazole, colorless prisms (recrystallized from ethanol), m.p. 141.5°–143.5° C.

1-Methyl-5-[4-(1-methyl-1,2,3,4-tetrazol-5-yl)thiobutyl]thio-1,2,3,4-tetrazole, colorless needles (recrystallized from ethanol), m.p. 122°–123° C.

1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°–128.5° C.

1-Methyl-5-[3-(1-cyclohexyl-1,2,3,4-tetrazol-5-yl)thiopropyl]thio-1,2,3,4-tetrazole, pale yellow liquid, $n_D^{18} = 1.5653$ 1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°–82° C.

1-Methyl-2-[3-(1-methylimidazol-2-yl)thiopropyl]thio-1,2,3,4-tetrazole, colorless needles (recrystallized from ether), m.p. 59.5°–60.5° C.

EXAMPLE 17

2-Pyridyl 3-chloropropyl sulfone (2.2 g) and 1-methyl-5-mercapto-1,2,3,4-tetrazole (1.2 g) are dissolved in acetone (50 ml). Potassium carbonate (1.4 g) is added to the solution and the mixture is refluxed for 5 hours. Acetone is distilled off and water is added to the residue. The mixture is extracted with chloroform. The chloroform solution is washed with saturated aqueous sodium chloride and dried over magnesium sulfate. Chloroform is distilled off and the residue is purified by column chromatography (Kieselgel 60). The column is eluted with chloroform-methanol and the product is recrystallized from ethanol to obtain 3-(1-methyl-1,2,3,4-tetrazol-5-yl)thiopropyl 2-pyridyl sulfone (1 g) as colorless prisms, m.p. 98.5°–101° C.

Elemental analysis for $C_{10}H_{13}N_5S_2O_2$: Calcd (%): C, 40.12; H, 4.38; N, 23.39. Found (%): C, 40.02; H, 4.46; N, 23.29.

EXAMPLE 18

According to the same manner as described in Example 17, the following compound is obtained:

3-(1-Methyl-1,2,3,4-tetrazol-5-yl)thiopropyl 2-pyridyl sulfoxide, colorless prisms (ethanol), m.p. 88.5°–90.5° C.

EXAMPLE 19

1-Methyl-5-(4,4-ethylenedioxyhexyl)thio-1,2,3,4-tetrazole (0.6 g) is dissolved in acetic acid (5 ml). Water (2.5 ml) and conc. hydrochloric acid (0.5 ml) are added to the solution and the mixture is heated on a water bath for 1 hour. Water is added to the reaction mixture and the mixture is extracted with chloroform. The chloroform solution is washed with water, saturated aqueous sodium bicarbonate and then saturated aqueous sodium chloride and dried over magnesium sulfate. Chloroform is distilled off and the residue is purified by silica gel column chromatography (Kieselgel 60). The column is eluted with benzene-ether (10:1) to obtain 1-methyl-5-(3-propionylpropyl)thio-1,2,3,4-tetrazole (0.4 g) as colorless liquid, $n_D^{25} = 1.5042$.

Elemental analysis for $C_8H_{14}N_4OS$: Calcd (%): C, 44.84; H, 6.59; N, 26.15. Found (%): C, 44.89; H, 6.63; N, 26.23.

EXAMPLE 20

According to the same manner as described in Example 19, the following compounds are obtained:

1-Methyl-5-(3-cyclohexylcarbonylpropyl)thio-1,2,3,4-tetrazole, colorless liquid, $n_D^{12} = 1.5267$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid, $n_D^{12} = 1.5282$ 1-Methyl-5-acetylmethylthio-1,2,3,4-tetrazole, colorless needles (recrystallized from methanol-ether), m.p. 31° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-(3-acetylpropyl)thio-1,2,3,4-tetrazole, colorless liquid, $n_D^{20} = 1.5194$ 1-Methyl-5-(3-pentanoylpropyl)thio-1,2,3,4-tetrazole, colorless liquid, $n_D^{23.5} = 1.5059$ 1-Methyl-5-(3-cyclopentylcarbonylpropyl)thio-1,2,3,4-tetrazole, colorless liquid, $n_D^{25} = 1.5256$

EXAMPLE 21

1-Methyl-5-[4,4-ethylenedioxy-4-(4-ethylphenyl)-butyl]thio-1,2,3,4-tetrazole (0.8 g) is dissolved in acetic acid (5 ml). Water (2.5 ml) and conc. hydrochloric acid (0.5 ml) are added to the solution and the mixture is heated on a water bath for 1 hour. Water is added to the reaction mixture and the mixture is extracted with chloroform. The chloroform is washed with water, saturated aqueous sodium bicarbonate and then saturated aqueous sodium chloride and dried over magnesium salfate. Chloroform is distilled off and the residue is purified by silica gel column chromatography (Kieselgel 60). The column is eluted with benzene-ether (10:1) to obtain 1-methyl-5-[3-(4-ethylbenzoyl)propyl]thio-1,2,3,4-tetrazole (0.5 g) as colorless needles, m.p. 68°–69° C. (recrystallized from hexane-ether).

Elemental analysis for $C_{14}H_{18}N_4OS$: Calcd (%): C, 57.91; H, 6.25; N, 19.90. Found (%): C, 57.68; H, 6.20; N, 19.81.

EXAMPLE 22

According to the same manner as described in Example 21, the following compounds are obtained:

1-Methyl-5-[3-(4-acetylaminobenzoyl)propyl]thio-1,2,3,4-tetrazole, colorless needles (recrystallized from ethanol), m.p. 170°–172° C.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-chlorobenzoyl)propyl]thio-1,2,3,4-tetrazole, colorless prisms (recrystallized from methanol-water), m.p. 139°–140° C.

1-Methyl-5-[3-(4-methoxybenzoyl)propyl]thio-1,2,3,4-tetrazole, colorless flakes (recrystallized from hexane-ethyl acetate), m.p. 107°–108° C.

1-Methyl-5-[3-(4-hydroxybenzoyl)propyl]thio-1,2,3,4-tetrazole, colorless needles (recrystallized from water), m.p. 128.5°–129.5° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25} = 1.5610$ 1-Methyl-5-[3-β-phenethylcarbonyl)propyl]thio-1,2,3,4-tetrazole, colorless liquid, $n_D^{25.5} = 1.5561$

EXAMPLE 23

1-Methyl-5-[4,4-ethylenedioxy-4-(2-pyridyl)-butyl]thio-1,2,3,4-tetrazole (0.7 g) is dissolved in acetic acid (5 ml). Water (2.5 ml) and conc. hydrochloric acid (0.5 ml) are added to the solution and the mixture is heated on a water bath for 1 hour. Water is added to the reaction mixture and the mixture is extracted with chloroform. The chloroform solution is washed with water, saturated aqueous sodium bicarbonate and saturated aqueous sodium chloride and dried over magnesium sulfate. Chloroform is distilled off and the residue is purified by silica gel column chromatography (Kieselgel 60). The column is eluted with benzene-ether (10:1) and the product is recrystallized from hexane-ether to obtain 1-methyl-5-[3-(2-pyridylcarbonyl)propyl]thio-1,2,3,4-tetrazole, (0.5 g) as colorless needles, m.p. 73°–75° C.

Elemental analysis for $C_{11}H_{13}N_5OS$: Calcd (%): C, 50.17; H, 4.97; N, 26.60. Found (%): C, 50.12; H, 4.97; N, 26.90.

EXAMPLE 24

According to the same manner as described in Example 23, the following compounds are obtained:

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(5-chloro-2-thenoyl)propyl]thio-1,2,3,4-tetrazole, pale yellow needles (recrystallized from hexane-ethyl acetate), m.p. 91°–92° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]-thio-1,2,3,4-tetrazole, colorless plates (recrystallized from hexane-ether), m.p. 67°–68.5° C.

1-Methyl-5-{3-[(3,4-dihydrocarbostyril-6-yl) carbonyl]propyl}thio-1,2,3,4-tetrazole, colorless needles (recrystallized from ethanol), m.p. 188°–190° C.

1-Methyl-5-{3-[(1-methyl-3,4-dihydrocarbostyril-6-yl)carbonyl]propyl}thio-1,2,3,4-tetrazole, colorless needles (recrystallized from hexane-ethyl acetate), m.p. 110°–113.5° C.

EXAMPLE 25A

1-Methyl-5-mercapto-1,2,3,4-tetrazole (0.01 mol), potassium carbonate (0.015 mol) and α-chloroacetone (0.015 mol) are added to acetone (50 ml) and the mixture is refluxed with stirring for 2 hours. The reaction mixture is concentrated to dryness under reduced pressure and the residue is dissolved in chloroform. Insolubles are filtered off. The filtrate is concentrated under reduced pressure and the residue is purified by silica gel column chromatography [Kieselgel 60, eluant: benzene-ether (10:1)] and the product is recrystallized from methanol-ether to obtain 1-methyl-5-acetylmethylthio-1,2,3,4-tetrazole (yield 48%) as colorless needles, m.p. 31° C.

Elemental analysis for $C_5H_8N_4OS$: Calcd (%): C, 34.87; H, 4.68; N, 32.54. Found (%): C, 34.43; H, 4.54; N, 38.83.

EXAMPLE 25B

5-Mercapto-1,2,3,4-tetrazole (1 g), potassium carbonate (2 g) and β-chloroacetone (1.4 g) are added to acetone (50 ml) and the solution is refluxed with stirring for 2 hours. The reaction mixture is concentrated to dryness under reduced pressure and the residue is dissolved in chloroform. Insolubles are filtered off and the filtrate is concentrated under reduced pressure. The residue is purified by silica gel column chromatography (Kieselgel 60, eluant: benzene-ether (10:1) to obtain 5-acetylmethylthio-1,2,3,4-tetrazole (0.4 g) as colorless liquid.

Elemental analysis for $C_4H_6ON_4S$: Calcd (%): C, 30.37; H, 3.82; N, 35.42. Found (%): C, 30.35; H, 3.81; N, 35.50.

EXAMPLE 26

According to the same manner as described in Example 25A, the following compounds are obtained:

1-Methyl-5-(3-cyclohexylcarbonylpropyl)thio-1,2,3,4-tetrazole, colorless liquid, $n_D^{12}=1.5267$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid, $n_D^{12}=1.5282$ 1-Methyl-5-(3-propionylpropyl)thio-1,2,3,4-tetrazole, colorless liquid, $n_D^{25}=1.5042$ 1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-(3-acetylpropyl)thio-1,2,3,4-tetrazole, colorless liquid, $n_D^{20}=1.5194$ 1-Methyl-5-(3-pentanoylpropyl)thio-1,2,3,4-tetrazole, colorless liquid, $n_D^{23.5}=1.5059$ 1-Methyl-5-(3-cyclopentylcarbonylpropyl)thio-1,2,3,4-tetrazole, colorless liquid, $n_D^{25}=1.5256$

EXAMPLE 27

1-Methyl-5-mercapto-1,2,3,4-tetrazole (1.2 g), potassium carbonate (2.1 g) and 3-chloropropyl 4-ethylphenyl ketone (3.2 g) are added to acetone (50 ml) and the mixture is refluxed with stirring for 2 hours. The reaction mixture is concentrated to dryness under reduced pressure and the residue is dissolved in chloroform. Insolubles are filtered off. The filtrate is concentrated under reduced pressure and the residue is purified by cilica gel column chromatography (Kieselgel 60, eluant: benzene-ether (10:1) and the product is recrystallized from hexane-ether to obtain 1-methyl-5-[3-(4-ethylbenzoyl)propyl]thio-1,2,3,4-tetrazole (yield 49%) as colorless needles, m.p. 68°–69° C.

Elemental analysis for $C_{14}H_{18}N_4OS$: Calcd (%): C, 57.91; H, 6.25; N, 19.90. Found (%): C, 57.78; H, 6.23; N, 19.71.

EXAMPLE 28

According to the same manner as described in Example 27, the following compounds are obtained:

1-Methyl-5-[3-(4-acetylaminobenzoyl)propyl]thio-1,2,3,4-tetrazole, colorless needles (recrystallized from ethanol), m.p. 170°–172° C.

1-Methyl-5-[3-(3,4-dimethoxybenzoyl)propyl]thio-1,2,3,4-tetrazole, colorless prisms (recrystallized from hexane-ethyl acetate), m.p. 86°-87° C.

1-Methyl-5-[3-(4-chlorobenzoyl)propyl]thio-1,2,3,4-tetrazole, colorless prisms (recrystallized from methanol-water), m.p. 139°-140° C.

1-Methyl-5-[3-(4-butoxybenzoyl)propyl]thio-1,2,3,4-tetrazole, colorless prisms (recrystallized from ethanol), m.p. 73.5°-75.5° C.

1-Methyl-5-[3-(2-methoxybenzoyl)propyl]thio-1,2,3,4-tetrazole, colorless needles (recrystallized from ethyl acetate-hexane), m.p. 98°-100° C.

1-Methyl-5-[3-(3-methoxybenzoyl)propyl]thio-1,2,3,4-tetrazole, colorless plates (recrystallized from ether-hexane), m.p. 48°-49° C.

1-Methyl-5-[3-(4-methoxybenzoyl)propyl]thio-1,2,3,4-tetrazole, colorless flakes (recrystallized from hexane-ethyl acetate), m.p. 107°-108° C.

1-Methyl-5-[3-(4-hydroxybenzoyl)propyl]thio-1,2,3,4-tetrazole, colorless needles (recrystallized from water), m.p. 128.5°-129.5° C.

EXAMPLE 29

1-Methyl-5-mercapto-1,2,3,4-tetrazole (1.2 g), potassium carbonate (2.1 g) and 3-chloropropyl 2-pyridyl ketone (2.8 g) are added to acetone (50 ml) and the mixture is refluxed with stirring for 2 hours. The reaction mixture is concentrated to dryness under reduced pressure and the residue is dissolved in chloroform. Insolubles are filtered off and the filtrated is concentrate under reduced pressure. The residue is purified by silica gel column chromatography (Kieselgel 60, eluant: benzene-ether (10:1)) and the product is recrystallized from hexane-ether to obtain 1-methyl-5-[3-(2-pyridylcarbonyl)propyl]thio-1,2,3,4-tetrazole (yield 50%) as colorless needles, m.p. 73°-75° C.

Elemental analysis for $C_{11}H_{13}N_5OS$: Calcd (%): C, 50.17; H, 4.97; N, 26.60. Found (%): C, 50.21; H, 4.89; N, 26.72.

EXAMPLE 30

According to the same manner as described in Example 29, the following compounds are obtained:

1-Methyl-5-[3-(2-thenoyl)propyl]thio-1,2,3,4-tetrazole, colorless needles (recrystallized from hexane-ether), m.p. 55°-56° C.

1-Methyl-5-[3-(2-furoyl)propyl]thio-1,2,3,4-tetrazole, colorless needles (recrystallized from hexane-ether), m.p. 41°-42° C.

1-Methyl-5-[3-(5-methyl-2-thenoyl)propyl]thio-1,2,3,4-tetrazole, pale yellow needles (recrystallized from hexane-ethyl acetate), m.p. 78°-80° C.

1-Methyl-5-[3-(5-chloro-2-thenoyl)propyl]thio-1,2,3,4-tetrazole, pale yellow needles (recrystallized from hexane-ethyl acetate), m.p. 91°-92° C.

1-Methyl-5-[3-(2-pyrrolylcarbonyl)propyl]thio-1,2,3,4-tetrazole, pale yellow prisms (recrystallized from hexane-ethyl acetate), m.p. 94°-96° C.

1-Methyl-5-[3-(2,5-dimethyl-3-furoyl)propyl]thio-1,2,3,4-tetrazole, colorless plates (recrystallized from hexane-ether), m.p. 67°-68.5° C.

1-Methyl-5-{3-[(3,4-dihydrocarbostyril-6-yl)carbonyl]propyl}thio-1,2,3,4-tetrazole, colorless needles (recrystallized from ethanol), m.p. 188°-190° C.

1-Methyl-5-{3-[(1-methyl-3,4-dihydrocarbostyril-6-yl)carbonyl]propyl}thio-1,2,3,4-tetrazole, colorless needles (recrystallized from hexane-ethyl acetate), m.p. 110°-113.5° C.

1-Methyl-5-[3-(5-methoxycarbonyl-2-furoyl)propyl]thio-1,2,3,4-tetrazole, colorless needles (recrystallized from hexane-ethyl acetate), m.p. 96°-97° C.

EXAMPLE 31

1-Methyl-5-mercapto-1,2,3,4-tetrazole (1.2 g), potassium carbonate (2.1 g) and 3-chloropropyl 4-methyl-5-thiazolyl ketone (3.1 g) are added to acetone (50 ml) and the mixture is refluxed with stirring for 2 hours. The reaction mixture is concentrated to dryness under reduced pressure and the residue is dissolved in chloroform. Insolubles are filtered off and the filtrated is concentrated under reduced pressure. The residue is purified by silica gel column chromatography [Kieselgel 60, eluant: benzene-ether (10:1)] and the product is recrystallized from hexane-ether to obtain 1-methyl-5-[3-(4-methyl-5-thiazolylcarbonyl)propyl]thio-1,2,3,4-tetrazole (2.6 g) as colorless needles, m.p. 64°-65° C.

EXAMPLE 32

According to the same manner as described in Example 31, 1-Methyl-5-[3-(5-carboxy-2-furoyl)propyl]thio-1,2,3,4-tetrazole is obtained as colorless prisms (hexane-ethyl acetate), m.p. 154°-157° C.

EXAMPLE 33

1-Methyl-5-mercapto-1,2,3,4-tetrazole (1.2 g), potassium carbonate (2.1 g) and 3-chloropropyl 2-naphthyl ketone (3.5 g) are added to acetone (50 ml) and the mixture is refluxed with stirring for 2 hours. The reaction mixture is concentrated to dryness under reduced pressure and the residue dissolved in chloroform. Insolubles are filtered off. The filtrated is concentrated and the residue is purified by silica gel column chromatography [Kieselgel 60, eluant: benzene-ether (10:1)] and the product is recrystallized from ethanol to obtain 1-methyl-5-[3-(2-naphthoyl)propyl]thio-1,2,3,4-tetrazole (yield 51%) as colorless prisms, m.p. 118°-120° C.

Elemental analysis for $C_{16}H_{16}N_4OS$: Calcd (%): C, 61.52; H, 5.16; N, 17.94. Found (%): C, 61.59; H, 5.08; N, 18.06.

EXAMPLE 34

1-Methyl-5-mercapto-1,2,3,4-tetrazole (1.2 g), potassium carbonate (2.1 g) and 3-chloropropyl benzyl ketone (2.9 g) are added to acetone (50 ml) and the mixture is refluxed with stirring for 2 hours. The reaction mixture is concentrated to dryness under reduced pressure and the residue is dissolved in chloroform. Insolubles are filtered off. The filtrate is concentrated under reduced pressure. The residue is purified by silica gel column chromatography [Kieselgel 60, eluant: benzene-ether (10:1)] to obtain 1-methyl-5-[3-(benzylcabonyl)propyl]thio-1,2,3,4-tetrazole (yield 50%) as colorless liquid, $n_D^{25}=1.5610$.

Elemental analysis for $C_{13}H_{16}N_4OS$: Calcd (%): C, 56.50; H, 5.84; N, 20.27. Found (%): C, 56.40; H, 5.83; N, 20.17.

EXAMPLE 35

According to the same manner as described in Example 34, 1-Methyl-5-[3-(β-phenethylcarbonyl)propyl]thio-1,2,3,4-tetrazole is obtained as colorless liquid, $n_D^{22.5}=1.5561$.

EXAMPLE 36

1-Methyl-5-chloro-1,2,3,4-tetrazole (2.4 g) is dissolved in ethanol (30 ml). Thiourea (1.5 g) is added to the solution and the mixture is refluxed for 2 hours. 3-Bromopropyl cyclohexyl ketone (4.7 g) and 10% aqueous sodium hydroxide (10 ml) are added to the mixture is further refluxed for 3 hours. Ethanol is distilled off and water is added to the residue. The mixture is extracted with chloroform. The chloroform solution is washed with water and then saturated aqueous sodium chloride and dried over magnesium sulfate. Chloroform is distilled off and the residue is purified by column chromatography (Wakogel C-200, eluant: chloroform) to obtain 1-methyl-5-(3-cyclohexylcarbonyl-propyl)thio-1,2,3,4-tetrazole (1.4 g) as colorlss liquid, $n_D^{12} = 1.5267$.

EXAMPLE 37

According to the same manner as described in Example 36, the following compounds are obtained:

1-Methyl-5-(3-propionylpropyl)thio-1,2,3,4-tetrazole, colorless liquid, $n_D^{25} = 1.5042$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid, $n_D^{12} = 1.5282$ 1-Methyl-5-acetylmethylthio-1,2,3,4-tetrazole, colorless needles (recrystallized from methanol-ether), m.p. 31° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-[3-(4-acetylaminobenzoyl)propyl]thio-1,2,3,4-tetrazole, colorless needles (recrystallized from ethanol), m.p. 170°–172° C.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-chlorobenzoyl)propyl]thio-1,2,3,4-tetrazole, colorless prisms (recrystallized from methanol-water), m.p. 139°–140° C.

1-Methyl-5-[3-(4-methoxybenzoyl)propyl]thio-1,2,3,4-tetrazole, colorless flakes (recrystallized from hexane-ethyl acetate), m.p. 107°–108° C.

1-Methyl-5-[3-(4-hydroxybenzoyl)propyl]thio-1,2,3,4-tetrazole, colorless needles (recrystallized from water), m.p. 128.5°–129.5° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25} = 1.5610$ 1-Methyl-5-[3-(β-phenethylcarbonyl)propyl]thio-1,2,3,4-tetrazole, colorlss liquid, $n_D^{25.5} = 1.5561$

EXAMPLE 38

S-(1-Methyl-1,2,3,4-tetrazole-5-yl)isothiourea hydrochloride (1.9 g) is dissolved in ethanol (50 ml). To the solution are added 10% aqueous sodium hydroxide (5 ml) and 3-chloropropyl 2-pyridyl ketone (1.8 g) and the mixture is refluxed for 2 hours. Ethanol is distilled off and water is added to the residue. The mixture is extracted with chloroform. The chloroform solution is washed with water and saturated aqueous sodium chloride and dried over magnesium sulfate. Chloroform is distilled off and the residue is purified by column chromatography (Wakogel C-200, eluant: chloroform) and the product is recrystallized from hexane-ether to obtain 1-methyl-5-[3-(2-pyridylcarbonyl)propyl]thio-1,2,3,4-tetrazole (0.5 g) as colorless needles, m.p. 73°–75° C.

EXAMPLE 39

According to the same manner as described in Example 38, the following compounds are obtained:

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(5-chloro-2-thenoyl)propyl]thio-1,2,3,4-tetrazole, pale yellow needles (recrystallized from hexane-ethyl acetate), m.p. 91°–92° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recrystallized from hexane-ether), m.p. 67°–68.5° C.

1-Methyl-5-{3-[(3,4-dihydrocarbostyril-6-yl)carbonyl]propyl}thio-1,2,3,4-tetrazole, colorless needles (recrystallized from ethanol), m.p. 188°–190° C.

1-Methyl-5-{3-[(1-methyl-3,4-dihydrocarbostyril-6-yl)carbonyl]propyl}thio-1,2,3,4-tetrazole, colorless needles (recrystallized from hexane-ethyl acetate), m.p. 110°–113.5° C.

EXAMPLE 40

1-Methyl-5-chloro-1,2,3,4-tetrazole (1.4 g) and 3-mercaptopropyl cyclohexyl ketone (1.9 g) are dissolved in methanol (50 ml) and potassium hydroxide (0.8 g) is added to the solution. The mixture is refluxed for 5 hours. Methanol is distilled off and water is added to the residue. The mixture is extracted with chloroform. The chloroform solution is washed with dil. aqueous sodium hydroxide, water and saturated aqueous sodium chloride and dried over sodium sulfate. Chloroform is distilled off and the residue is purified by column chromatography (Wakogel C-200, eluant: chloroform) to obtain 1-methyl-5-(3-cyclohexylcarbonylpropyl)thio-1,2,3,4-tetrazole (0.6 g) as colorless liquid, $n_D^{12} = 1.5267$.

EXAMPLE 41

According to the same manner as described in Example 40, the following compounds are obtained:

1-Methyl-5-(3-propionylpropyl)thio-1,2,3,4-tetrazole, colorless liquid, $n_D^{25} = 1.5042$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid, $n_D^{12} = 1.5282$ 1-Methyl-5-acetylmethylthio-1,2,3,4-tetrazole, colorless needles (recrystallized from methanol-ether), m.p. 31° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroine), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-[3-(4-acetylaminobenzoyl)propyl]thio-1,2,3,4-tetrazole, colorless needles (recrystallized from ethanol), m.p. 170°–172° C.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-chlorobenzoyl)propyl]thio-1,2,3,4-tetrazole, colorless prisms (recrystallized from methanol-water), m.p. 139°–140° C.

1-Methyl-5-[3-(4-methoxybenzoyl]propyl]thio-1,2,3,4-tetrazole, colorless flakes (recrystallized from hexane-ethyl acetate), m.p. 107°–108° C.

1-Methyl-5-[3-(4-hydroxybenzoyl)propyl]thio-1,2,3,4-tetrazole, colorless needles (recrystallized from water), m.p. 128.5°–129.5° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25} = 1.5610$ 1-Methyl-5-[3-(β-phenethylcarbonyl)propyl]thio-1,2,3,4-tetrazole, colorless liquid, $n_D^{25.5} = 1.5561$.

EXAMPLE 42

1-Methyl-5-chloro-1,2,3,4-tetrazole (1.4 g) and 3-mercaptopropyl 2-pyridyl ketone (1.8 g) is dissolved in methanol (100 ml). Sodium hydroxide (0.6 g) is added to the solution and the mixture is refluxed for 3 hours. Methanol is distilled off and water is added to the residue. The mixture is extracted with chloroform. The chloroform solution is washed with dil. aqueous sodium hydroxide, water and saturated aqueous sodium chloride and dried over sodium sulfate. Chloroform is distilled off and the residue is purified by column chromatography (Wakogel C-200, eluant: chloroform) and the product is recrystallized from hexane-ether to obtain 1-methyl-5-[3-(2-pyridylcarbonyl)propyl]thio-1,2,3,4-tetrazole (0.2 g) as colorless needles, m.p. 73°–75° C.

EXAMPLE 43

According to the same manner as described in Example 42, the following compounds are obtained:

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(5-chloro-2-thenoyl)propyl]thio-1,2,3,4-tetrazole, pale yellow needles (recrystallized from hexane-ethyl acetate), m.p. 91°–92° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recrystallized from hexane-ether), m.p. 67°–68.5° C.

1-Methyl-5-{3-[(3,4-dihydrocarbostyril-6-yl)carbonyl]propyl}thio-1,2,3,4-tetrazole, colorless needles (recrystallized from ethanol), m.p. 188°–190° C.

1-Methyl-5-{3-[(1-methyl-3,4-dihydrocarbostyril-6-yl)carbonyl]propyl}thio-1,2,3,4-tetrazole, colorless needles (recrystallized from hexane-ethyl acetate), m.p. 110°–113.5° C.

EXAMPLE 44

4-Chlorobutyrophenone (1.8 g) and thiourea (0.8 g) is dissolved in ethanol (50 ml) and the solution is refluxed for 2 hours. To the mixture are added 1-methyl-5-chloro-1,2,3,4-tetrazole (1.2 g) and 10% aqueous sodium hydroxide (5 ml) and the mixture is further refluxed for 3 hours. Ethanol is distilled off and water is added to the residue. The mixture is extracted with chloroform. The chloroform solution is washed with water and saturated aqueous sodium chloride and dried over magnesium sulfate. Chloroform is distilled off. The residue is purified by column chromatography (Wakogel C-200, eluatn: chloroform) and the product is recrystallized from methanol-water to obtain 1-methyl-5-(3-benzoylpropyl)thio-1,2,3,4-tetrazole (0.3 g) as colorless needles, m.p. 57.5°–58° C.

EXAMPLE 45

According to the same manner as described in Example 44, the following compounds are obtained:

1-Methyl-5-(3-propionylpropyl)thio-1,2,3,4-tetrazole, colorless liquid, $n_D^{25} = 1.5042$ 1-Methyl-5-(3-cyclohexylcarbonylpropyl)thio-1,2,3,4-tetrazole, colorless liquid, $n_D^{12} = 1.5267$ 1-Phenyl-5-(3-cyclohexylcarbonylpropyl)thio-1,2,3,4-tetrazole, colorless granules (recrystallized from methanol-water), m.p. 57.5°–58.5° C.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid, $n_D^{12} = 1.5282$ 1-Methyl-5-acetylmethylthio-1,2,3,4-tetrazole, colorless needles (recrystallized from methanol-ether), m.p. 31° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-[3-(4-acetylaminobenzoyl)propyl]thio-1,2,3,4-tetrazole, colorless needles (recrystallized from ethanol), m.p. 170°–172° C.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-chlorobenzoyl)propyl]thio-1,2,3,4-tetrazole, colorless prisms (recrystallized from methanol-water), m.p. 139°–140° C.

1-Methyl-5-[3-(4-methoxybenzoyl]thio-1,2,3,4-tetrazole, colorless flakes (recrystallized from hexane-ethyl acetate), m.p. 107°–108° C.

1-Methyl-5-[3-(4-hydroxybenzoyl)propyl]thio-1,2,3,4-tetrazole, colorless needles (recrystallized from water), m.p. 128.5°–129.5° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25}=1.5610$ 1-Methyl-5-[3-($\beta$-phenethylcarbonyl)propyl]thio-1,2,3,4-tetrazole, colorless liquid, $n_D^{25.5}=1.5561$

EXAMPLE 46

3-Chloropropyl 2-pyridyl ketone (1.8 g) and thiourea (0.8 g) are dissolved in ethanol (50 ml), and the solution is refluxed with stirring for 2 hours. To the mixture are added 1-methyl-5-chloro-1,2,3,4-tetrazole (1.2 g) and 10% aqueous sodium hydroxide (5 ml), and the mixture is refluxed for 3 hours. After evaporating ethanol under reduced pressure, water is added to the residue. The mixture is extracted with chloroform, and the extract is washed with water and saturated aqueous sodium chloride and dried over magnesium sulfate. After chloroform is distilled off, the residue is purified by column chromatography (Wakogel C-200, eluting agent, chloroform), followed by recrystallized from hexane-ether to give 1-methyl-5-[3-(2-pyridylcarbonyl)propyl]thio-1,2,3,4-tetrazole (0.2 g) as colorless crystals, m.p. 73°–75° C.

EXAMPLE 47

In the same manner as described in Example 47, the following compounds are prepared.

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(5-chloro-2-thenoyl)propyl]thio-1,2,3,4-tetrazole, pale yellow needles (recrystallized from hexane-ethyl acetate), m.p. 91°–92° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recrystallized from hexane-ether), m.p. 67°–68.5° C.

1-Methyl-5-{3-[(3,4-dihydrocarbostyril-6-yl)carbonyl]propyl}thio-1,2,3,4-tetrazole, colorless needles (recrystallized from ethanol), m.p. 188°–190° C.

1-Methyl-5-{3-[(1-methyl-3,4-dihydrocarbostyril-6-yl)carbonyl]propyl}thio-1,2,3,4-tetrazole, colorless needles (recrystallized from hexane-ethyl acetate), m.p. 110°–113.5° C.

EXAMPLE 48

1-Methyl-5-mercapto-1,2,3,4-tetrazole (2.4 g) and N-ethyl-N-propionyl-3-chloropropylamine (3.6 g) are dissolved in acetone (50 ml). To the mixture are added potassium carbonate (2.8 g) and potassium iodide (0.1 g), and the mixture is refluxed for 4 hours. After acetone is distilled off, the residue is added to water and extracted with chloroform. The chloroform solution is washed with saturated aqueous sodium chloride and dried over sodium sulfate. After chloroform is distilled off, the residue is purified by column chromatography (neutral alumina, made by Merck) and eluted with n-hexane to give 1-methyl-5-[3-(N-ethyl-N-propionylamino)propylthio]-1,2,3,4-tetrazole (1.2 g) as pale yellow liquid, $n_D^{21.5}=1.5220$.

EXAMPLE 49

In the same manner as described in Example 48, the following compounds are prepared.

1-Methyl-5-[3-(N-propionylamino)propylthio]-1,2,3,4-tetrazole, pale yellow liquid, $n_D^{8.5}=1.5311$ 1-Methyl-5-[3-(N-ethyl-N-cyclohexylcarbonylamino)propylthio]-1,2,3,4-tetrazole, colorless liquid, $n_D^{23.5}=1.5267$ 1-Methyl-5-[3-(N-cyclohexylcarbonylamino)propylthio]-1,2,3,4-tetrazole, colorless flakes (hexane-ethyl acetate), m.p. 86.5°–88° C.

1-Phenyl-5-[3-(N-ethyl-N-benzoylamino)propylthio]-1,2,3,4-tetrazole, colorless liquid, $n_D^{24}=1.5898$ 1-phenyl-5-[3-(N-benzoylamino)propylthio]-1,2,3,4-tetrazole, colorless needles (hexane-ethyl acetate), m.p. 105°–107° C.

1-Methyl-5-[3-(N-methyl-N-acethylamino)propylthio]-1,2,3,4-tetrazole, pale yellow prisms (hexane-ethyl acetate), m.p. 80°–81° C.

1-Methyl-5-[3-(N-acetylamino)propylthio]-1,2,3,4-tetrazole, colorless liquid, $n_D^{26.5}=1.5280$ 1-Methyl-5-[3-(N-methyl-N-cyclohexylcarbonylamino)propylthio]-1,2,3,4-tetrazole, colorless liquid, $n_D^{19}=1.5268$ 1-Methyl-5-[3-(N-ethyl-N-cyclopentylcarbonylamino)propylthio]-1,2,3,4-tetrazole, colorless liquid, $n_D^{28.5}=1.5240$ 1-Methyl-5-[3-(N-cyclopentylcarbonylamino)propylthio]-1,2,3,4-tetrazole, colorless prisms (ether), m.p. 70°–72° C.

1-Methyl-5-[2-(N-cyclohexylcarbonylamino)ethylthio]-1,2,3,4-tetrazole, colorless needles (ether-ligroin), m.p. 115.5°–116.5° C.

1-Methyl-5-[3-(N-ethyl-N-benzoylamino)propylthio]-1,2,3,4-tetrazole, colorless liquid, $n_D^{26.5}=1.5454$ 1-Methyl-5-{3-[N-(2-pyridylcarbonyl)amino]propylthio}-1,2,3,4-tetrazole, brown liquid, $n_D^{26.5}=1.5782$ 1-Methyl-5-{3-[N-ethyl-N-(2-furylcarbonyl)amino]-propylthio}-1,2,3,4-tetrazole, colorless liquid, $n_D^{28.5} = 1.5495$ 1-Methyl-5-{3-[N-(2-furylcarbonyl)amino]propylthio}-1,2,3,4-tetrazole, colorless prisms (ethanol-hexane), m.p. 80.5°–83° C.

1-Methyl-5-[3-(N-benzyl-N-propionylamino)propylthio]-1,2,3,4-tetrazole, colorless liquid, $n_D^{26} = 1.5538$ 1-Methyl-5-[3-(N-benzoylamino)propylthio]-1,2,3,4-tetrazole, colorless prisms (ethanol-hexane), m.p. 76°–77.5° C.

1-Methyl-5-[3-(N-hexanoylamino)propylthio]-1,2,3,4-tetrazole, pale yellow liquid, $n_D^{21} = 1.5133$

EXAMPLE 50

1-Methyl-5-mercapto-1,2,3,4-tetrazole (2.4 g) and N,N-diethyl-3-chloropropylamine (3.0 g) are dissolved in acetone (50 ml). To the mixture are added potassium carbonate (2.8 g) and potassium iodide (0.1 g), and the mixture is refluxed for 4 hours. After acetone is distilled off, water is added to the residue and extracted with chloroform. The chloroform solution is washed with saturated aqueous sodium chloride and dried over sodium sulfate. After chloroform is distilled off, the residue is purified by column chromatography (neutral alumina, made by Merck) and eluted with n-hexane to give 1-methyl-5-[3-(N,N-diethylamino)propylthio]-1,2,3,4-tetrazole (1.09 g) as colorless liquid, $n_D^{25} = 1.5040$.

EXAMPLE 51

In the same manner as described in Example 50, the following compounds are prepared.

1-Methyl-5-[4-(N-benzyl-N-ethylamino)butyl]thio-1,2,3,4-tetrazole, brown liquid, $n_D^{26.5} = 1.5520$ 1-Methyl-5-[3-(N,N-dimethylamino)propyl]thio-1,2,3,4-tetrazole, colorless liquid, $n_D^{21} = 1.5120$ 1-Methyl-5-[3-(5-methylamino-1,2,3,4-tetrazol-1-yl)propyl]thio-1,2,3,4-tetrazole, colorless prisms (ethanol), m.p. 122°–124.5° C.

EXAMPLE 52

1-Methyl-5-mercapto-1,2,3,4-tetrazole (2.4 g) and 2-chloromethylpyridine (2.6 g) are dissolved in acetone (50 ml). To the mixture are added potassium carbonate (2.8 g) and patassium iodide (0.1 g), and the mixture is refluxed for 4 hours. After acetone is distilled off, water is added to the residue and extracted with chloroform. The chloroform solution is washed with saturated aqueous sodium chloride and dried over sodium sulfate. After chloform is distilled off, the residue is purified by column chromatography (neutral alumina, made by Merck) and eluted with n-hexane to give 1-methyl-5-(2-pyridyl)methylthio-1,2,3,4-tetrazole (1.0 g) as colorless prisms (ethanol), m.p. 78°–81° C.

EXAMPLE 53

In the same manner as described in Example 52, following compounds are prepared.

1-Methyl-5-(3-pyridyl)methylthio-1,2,3,4-tetrazole, colorless liquid, $n_D^{29} = 1.5845$ 1-Methyl-5-(2-amino-thiazol-4-yl)methylthio-1,2,3,4-tetrazole, colorless needles (ethanol), m.p. 114°–118° C.

1-Methyl-5-(4-methoxybenzyl)thio-1,2,3,4-tetrazole, colorless liquid, $n_D^{22.5} = 1.5878$ 1-Methyl-5-cyclohexylmethylthio-1,2,3,4-tetrazole, colorless liquid, $n_D^{22.5} = 1.5298$

EXAMPLE 54

Ethylmagnesium bromide is prepared from magnesium (0.25 g), ethyl bromide (1.2 g) and dried tetrahydrofuran (10 ml). To the product is added dropwise a solution of 4-(1-methyl-1,2,3,4-tetrazol-5-yl)thiobutyronitrile (1.8 g) in dried tetrahydrofuran (10 ml) with stirring under ice-cooling. After the solution is added, the mixture is stirred at room temperature for 3 hours. To the mixture is added 1 N-HCl (50 ml) under ice-cooling and the mixture is stirred for 1 hour. The reaction mixture is diluted with water and extracted with chloroform. The chloroform solution is washed with saturated aqueous sodium bicarbonate and saturated aqueous sodium chloride and dried over sodium sulfate. After chloroform is distilled off, the residue is purified by column chromatography (Kieselgel 60) and eluted with benzene-ether (10:1) to give 1-methyl-5-(3-propionylpropyl)thio-1,2,3,4-tetrazole (0.5 g) as colorless liquid, $n_D^{25} = 1.5042$.

EXAMPLE 55

In the same manner as described in Example 54, the following compounds are prepared.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid $n_D^{12} = 1.5282$ 1-Methyl-5-acetylmethylthio-1,2,3,4-tetrazole, colorless needles (recrystallized from methanol-ether), m.p. 31° C.

1-Methyl-5-(3-cyclohexylcarbonylpropyl)thio-1,2,3,4-tetrazole, colorless liquid, $n_D^{12} = 1.5267$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-(3-acetylpropyl)thio-1,2,3,4-tetrazole, colorless liquid, $n_D^{20} = 1.5194$ 1-Methyl-5-(3-pentanoylpropyl)thio-1,2,3,4-tetrazole, colorless liquid, $n_D^{23.5} = 1.5059$ 1-Methyl-5-(3-cyclopentylcarbonylpropyl)thio-1,2,3,4-tetrazole, colorless liquid, $n_D^{25} = 1.5256$

EXAMPLE 56

4-Ethylphenylmagnesium bromide is prepared from magnesium (0.25 g), 4-ethyl-1-bromobenzene (2.6 g) and dried tetrahydrofuran (10 ml). To the product is added dropwise a solution of 1-methyl-5-(3-cyanopropyl)thio-1,2,3,4-tetrazole (1.8 g) in dried tetrahydrofuran (10 ml) with stirring under ice-cooling. After the solution is added, the mixture is stirred at room temperature for 3 hours. To the mixture is added 1 N-HCl (50 ml) under ice-cooling and the mixture is stirred for 1 hour. The reaction mixture is diluted with water and extracted with chloroform. The chloroform solution is washed with saturated aqueous sodium bicarbonate and saturated aqueous sodium chloride and dried over sodium sulfate. After chloroform is distilled off, the residue is purified by column chromatography (Kieselgel 60) and eluted with benzene-ether (10:1) to give 1-methyl-5-[3-(4-ethylbenzoyl)propyl]thio-1,2,3,4-tetrazole (0.7 g) as colorless needles (recrystallized from hexane-ether), m.p. 68°–69° C.

EXAMPLE 57

In the same manner as described in Example 56, the following compounds are prepared.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-methoxybenzoyl)propyl]thio-1,2,3,4-tetrazole, colorless flakes (recrystallized from hexane-ethyl acetate), m.p. 107°–108° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25} = 1.5610$ 1-Methyl-5-[3-($\beta$-phenethylcarbonyl)propyl]thio-1,2,3,4-tetrazole, colorless liquid, $n_D^{25.5} = 1.5561$

EXAMPLE 58

Pyridylmagnesium bromide is prepared from magnesium (0.25 g), 2-bromopyridine (2.1 g) and dried tetrahydrofuran (10 ml). To the product is added dropwise a solution of 1-methyl-5-(3-cyanopropyl)thio-1,2,3,4-tetrazole (1.8 g) in dried tetrahydrofuran (10 ml) with stirring under ice-cooling. After the solution is added, the mixture is stirred at room temperature for 3 hours. To the mixture is added 1 N-HCl (50 ml) under ice-cooling and the mixture is stirred for 1 hour. The reaction mixture is diluted with water and extracted with chloroform. The chloroform solution is washed with saturated aqueous sodium bicarbonate and saturated aqueous sodium chloride and dried over sodium sulfate. After chloroform is distilled off, the residue is purified by column chromatography (Kieselgel 60) and eluted with benzene-ether (10:1) to give 1-methyl-5-[3-(2-pyridylcarbonyl)propyl]thio-1,2,3,4-tetrazole (0.6 g) as colorless needles (hexane-ether) m.p. 73°–75° C.

EXAMPLE 59

In the same manner as described in Example 58, the following compounds are prepared.

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recristallized from hexane-ether), m.p. 67°–68.5° C.

EXAMPLE 60

Magnesium (0.3 g) is suspended in dried tetrahydrofuran (5 ml). To the suspension is added a small piece of iodine with stirring in nitrogen gas flow, and further added 1-methyl-5-(3-chloropropyl)thio-1,2,3,4-tetrazole (0.3 g). To the mixture is added ethyl bromide (0.1 ml), and the reaction is started by heating the mixture from outside. A solution of 1-methyl-5-(3-chloropropyl)thio-1,2,3,4-tetrazole (1.8 g) in dried tetrahydrofuran (15 ml) is additionally added dropwise to the mixture. After the solution is added, the mixture is refluxed for 1 hour. To the obtained Grignard reagent is added dropwise a solution of propionitrile (0.5 g) in dried tetrahydrofuran (5 ml) with stirring under ice-cooling, and the mixture is stirred for 3 hours at room temperature. To the mixture is added 1 N-HCl (20 ml) under ice-cooling and the mixture is stirred for 1 hour. The reaction mixture is diluted with water and extracted with chloroform. The chloroform solution is washed with saturated aqueous sodium bicarbonate and saturated aqueous sodium chloride and dried over sodium sulfate. After chloroform is distilled off, the residue is purified by silica gel column chromatography (Kieselgel 60) and eluted with benzene-ether (10:1) to give 1-methyl-5-(3-propionylpropyl)thio-1,2,3,4-tetrazole (0.5 g) as colorless liquid, $n_D^{25} = 1.5042$.

EXAMPLE 61

In the same manner as described in Example 60, the following compounds are prepared.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid $n_D^{12} = 1.5282$ 1-Methyl-5-acetylmethylthio-1,2,3,4-tetrazole, colorless needles (recrystallized from methanol-ether), m.p. 31° C.

1-Methyl-5-(3-cyclohexylcarbonylpropyl)thio-1,2,3,4-tetrazole, colorless liquid, $n_D^{12} = 1.5267$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Methyl-5-benzolymethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-(3-acetylpropyl)thio-1,2,3,4-tetrazole, colorless liquid, $n_D^{20} = 1.5194$ 1-Methyl-5-(3-pentanoylpropyl)thio-1,2,3,4-tetrazole, colorless liquid, $n_D^{23.5} = 1.5059$ 1-Methyl-5-(3-cyclopentylcarbonylpropyl)thio-1,2,3,4-tetrazole, colorless liquid, $n_D^{25} = 1.5256$

EXAMPLE 62

Magnesium (0.3 g) is suspended in dried tetrahydrofuran (5 ml). To the suspension is added a small piece of iodine with stirring in nitrogen gas flow, and further added 1-methyl-5-(3-chloropropyl)thio-1,2,3,4-tetrazole (0.3 g). To the mixture is added ethyl bromide (0.1 ml), and the reaction is started by heating the mixture from outside. A solution of 1-methyl-5-(3-chloropropyl)thio-1,2,3,4-tetrazole (1.8 g) in dried tetrahydrofuran (15 ml) is additionally added dropwise to the mixture. After the solution is added, the mixture is refluxed for 1 hour. To the obtained Grignard reagent is added dropwise a solution of 1-cyano-4-ethylbenzene (1.1 g) in dried tetrahydrofuran (5 ml) with stirring under ice-cooling, and the mixture is stirred for 3 hours at room temperature. To the mixture is added 1 N-HCl (20 ml) under ice-cooling and the mixture is stirred for 1 hour. The reaction mixture is diluted with water and extracted with chloroform. The chloroform solution is washed with saturated aqueous sodium bicarbonate and saturated aqueous sodium chloride and dried over sodium sulfate. After chloroform is distilled off, the residue is purified by silica gel column chromatography (Kieselgel 60) and eluted with benzene-ether 10:1) to give 1-methyl-5-[3-(4-ethylbenzoyl)propyl]thio-1,2,3,4-tetrazole (0.7 g) as colorless needles (recrystallized from hexane-ether), m.p. 68°–69° C.

EXAMPLE 63

In the same manner as described in Example 62, the following compounds are prepared.
1-Methyl-5-[3-(3,4-dimethoxybenzoyl)propyl]thio-1,2,3,4-tetrazole, colorless prisms (recrystallized from hexane-ethyl acetate), m.p. 86°–87° C.
1-Methyl-5-[3-(4-chlorobenzoyl)propyl]thio-1,2,3,4-tetrazole, colorless prisms (recrystallized from methanol-water), m.p. 139°–140° C.
1-Methyl-5-[3-(4-methoxybenzoyl)propyl]thio-1,2,3,4-tetrazole, colorless flakes (recrystallized from hexane-ethyl acetate), m.p. 107°–108° C.
1-Methyl-5-[3-(2-naphthoyl)propyl]thio-1,2,3,4-tetrazole, colorless prisms (recrystallized from ethanol), m.p. 118°–120° C.
1-Methyl-5-[3-(benzylcarbonyl)propyl]thio-1,2,3,4-tetrazole, colorless liquid, $n_D^{25} = 1.5610$
1-Methyl-5-[3-(β-phenethylcarbonyl)propyl]thio-1,2,3,4-tetrazole, colorless liquid, $n_D^{25.5} = 1.5561$

EXAMPLE 64

Magnesium (0.3 g) is suspended in dried tetrahydrofuran (5 ml). To the suspension is added a small piece of iodine with stirring in nitrogen gas flow, and further added 1-methyl-5-(3-chloropropyl)thio-1,2,3,4-tetrazole (0.3 g). To the mixture is added ethyl bromide (0.1 ml), and the reaction is started by heating the mixture from outside. A solution of 1-methyl-5-(3-chloropropyl)thio-1,2,3,4-tetrazole (1.8 g) in dried tetrahydrofuran (15 ml) is additionally added dropwise to the mixture. After the solution is added, the mixture is refluxed for 1 hour. To the obtained Grignard reagent is added dropwise a solution of 2-cyanopyridine (0.9 g) in dried tetrahydrofuran (5 ml) with stirring under ice-cooling, and the mixture is stirred for 3 hours at room temperature. To the mixture is added 1 N-HCl (20 ml) under ice-cooling and the mixture is stirred for 1 hour. The reaction mixture is diluted with water and extracted with chloroform. The chloroform solution is washed with saturated aqueous sodium bicarbonate and saturated aqueous sodium chloride and dried over sodium sulfate. After chloroform is distilled off, the residue is purified by silica gel column chromatography (Kieselgel 60) and eluted with benzene-ether (10:1) to give 1-methyl-5-[3-(2-pyridylcarbonyl)propyl]thio-1,2,3,4-tetrazole (0.6 g) as colorless needles (recrystallized from hexane-ether), m.p. 73°–75° C.

EXAMPLE 65

In the same manner as described in Example 64, the following compounds are prepared.
1-Methyl-5-[3-(2-thenoyl)propyl]thio-1,2,3,4-tetrazole, colorless needles (recrystallized from hexane-ether), m.p. 55°–56° C.
1-Methyl-5-[3-(2-furoyl)propyl]thio-1,2,3,4-tetrazole, colorless needles (recrystallized from hexane-ether), m.p. 41°–42° C.
1-Methyl-5-[3-(5-methyl-2-thenoyl)propyl]thio-1,2,3,4-tetrazole, pale yellow needles (recrystallized from hexane-ethyl acetate), m.p. 78°–80° C.
1-Methyl-5-[3-(5-chloro-2-thenoyl)propyl]thio-1,2,3,4-tetrazole, pale yellow needles (recrystallized from hexane-ethyl acetate), m.p. 91°–92° C.
1-Methyl-5-[3-(2-pyrrolylcarbonyl)propyl]thio-1,2,3,4-tetrazole, pale yellow prisms (recrystallized from hexane-ethyl acetate), m.p. 94°–96° C.
1-Methyl-5-[3-(2,5-dimethyl-3-furoyl)propyl]thio-1,2,3,4-tetrazole, colorless plates (recristallized from hexane-ether), m.p. 67°–68.5° C.

EXAMPLE 66

4-(1-Methyl-1,2,3,4-tetrazol-5-yl)thio-butyric acid (2 g) is dissolved in absolute benzene (20 ml). To the mixture is added dropwise 1.5 N solution of ethyllithium in ether (13.3 ml) with stirring at −70° C. in argon gas flow. The mixture is stirred for 3 hours while it is heated slowly to room temperature. Then, the reaction mixture is stirred overnight at room temperature and is poured into ice-water, and extracted with ether. The ether solution is washed with saturated aqueous sodium bicarbonate and saturated aqueous sodium chloride and dried over magnesium sulfate. After ether is distilled off, the residue is purified by column chromatography (Kieselgel 60) and eluted with benzene-ether (10:1) to give 1-methyl-5-(3-propionylpropyl)thio-1,2,3,4-tetrazole (0.5 g) as colorless liquid, $n_D^{25} = 1.5042$.

EXAMPLE 67

In the same manner as described in Example 66, the following compounds are prepared.
1-Phenyl-5-(3-benzoylpropyl)thio-1,2,3,4-tetrazole, colorless granules (recrystallized from methanol-water), m.p. 71°–72° C.
1-Cyclohexyl-5-(3-cyclohexylcarbonylpropyl)thio-1,2,3,4-tetrazole, pale yellow liquid $n_D^{12} = 1.5282$
1-Methyl-5-acetylmethylthio-1,2,3,4-tetrazole, colorless needles (recrystallized from methanol-ether), m.p. 31° C.
1-Methyl-5-(3-cyclohexylcarbonylpropyl)thio-1,2,3,4-tetrazole, colorless liquid, $n_D^{12} = 1.5267$
1-Methyl-5-(3-benzoylpropyl)thio-1,2,3,4-tetrazole, colorless needles (recrystallized from methanol-water), m.p. 57.5°–58° C.
1-Phenyl-5-(3-cyclohexylcarbonylpropyl)thio-1,2,3,4-tetrazole, colorless granules (recrystallized from methanol-water), m.p. 57.5°–58.5° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-(3-acetylpropyl)thio-1,2,3,4-tetrazole, colorless liquid, $n_D^{20} = 1.5194$ 1-Methyl-5-(3-pentanoylpropyl)thio-1,2,3,4-tetrazole, colorless liquid, $n_D^{23.5} = 1.5059$ 1-Methyl-5-(3-cyclopentylcarbonylpropyl)thio-1,2,3,4-tetrazole, colorless liquid, $n_D^{25} = 1.5256$

EXAMPLE 68

1-Methyl-5-(3-carboxypropyl)thio-1,2,3,4-tetrazole (2 g) is dissolved in absolute benzene (20 ml). To the mixture is added dropwise 1.5 N solution of ethyllithium in ether (13.3 ml) with stirring at −70° C. in argon gas flow. The mixture is stirred for 3 hours while it is heated slowly to room temperature. Then, the reaction mixture is stirred overnight at room temperature and is poured into ice-water, and extracted with ether. The ether solution is washed with saturated aqueous sodium bicarbonate and saturated aqueous sodium chloride and dried over magnesium sulfate. After ether is distilled off, the residue is purified by column chromatography (Kieselgel 60) and eluted with benzene-ether (10:1) to give 1-methyl-5-[3-(4-ethylbenzoyl)propyl]thio-1,2,3,4-tetrazole (0.7 g) as colorless needles (recrystallized from hexane-ether), m.p. 68°–69° C.

EXAMPLE 69

In the same manner as described in Example 68, the following compounds are prepared.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-methoxybenzoyl)propyl]thio-1,2,3,4-tetrazole, colorless flakes (recrystallized from hexane-ethyl acetate), m.p. 107°–108° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25} = 1.5610$ 1-Methyl-5-[3-(β-phenethylcarbonyl)propyl]thio-1,2,3,4-tetrazole, colorless liquid, $n_D^{25.5} = 1.5561$

EXAMPLE 70

1-Methyl-5-(3-carboxypropyl)thio-1,2,3,4-tetrazole (2 g) is dissolved in absolute benzene (20 ml). To the mixture is added dropwise 1.5 N solution of ethyllithium in ether (13.3 ml) with stirring at −70° C. in argon gas flow. The mixture is stirred for 3 hours while it is heated slowly to room temperature. Then, the reaction mixture is stirred overnight at room temperature and is poured into ice-water, and extracted with ether. The ether solution is washed with saturated aqueous sodium bicarbonate and saturated aqueous sodium chloride and dried over magnesium sulfate. After ether is distilled off, the residue is purified by column chromatography (Kieselgel 60) and eluted with benzene-ether (10:1) to give 1-methyl-5-[3-(2-pyridylcarbonyl)propyl]thio-1,2,3,4-tetrazole (0.6 g) as colorless needles (recrystallized from hexane-ether), m.p. 73°–75° C.

EXAMPLE 71

In the same manner as described in Example 70, the following compounds are prepared.

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recristallized from hexane-ether), m.p. 67°–68.5° C.

EXAMPLE 72

2-Ethyl-1,3,-dithian (1,5 g) is dissolved in dried tetrahydrofuran (20 ml) and cooled to −78° C. To the mixture is added dropwise 1.6 N solution of n-butyllithium in n-hexane (6.5 ml) with stirring in argon gas flow. The mixture is stirred at −78° C. for 30 minutes. To the mixture is added dropwise a solution of 1-methyl-5-(3-chloropropyl)thio-1,2,3,4-tetrazole (1.9 g) in dried tetrahydrofuran (5 ml). After stirring at −78° C. for 1 hour, the mixture is stirred 4 hours while it is heated slowly to 0° C. The reaction mixture is poured into ice-water and extracted with ether. The ether solution is washed with water and saturated aqueous sodium chloride and dried over magnesium sulfate. After ether is distilled off, the residue is dissolved in acetonitrile (20 ml). Silver nitrate (7 g) and N-chlorosuccinimide (4.9 g) are dissolved in a mixture of water (40 ml) and acetonitrile (100 ml). To the mixture is added dropwise the dithian solution as above-mentioned with stirring at 0° C. in nitrogen gas flow. After stirring at 0° C. for 30 minutes, the mixture is heated to room temperature and further stirred for 30 minutes. The reaction mixture is diluted with water and extracted with chloroform. The chloroform solution is washed with water and saturated aqueous sodium chloride and dried over magnesium sulfate. After chloroform is distilled off, the residue is purified by column chromatography (Kieselgel 60) and eluted with benzene-ether (10:1) to give 1-methyl-5-(3-propionylpropyl)thio-1,2,3,4-tetrazole (0.3 g) as colorless liquid, $n_D^{25} = 1.5042$

EXAMPLE 73

In the same manner as described in Example 72, the following compounds are prepared.

1-Phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazole, pale yellow liquid $n_D^{12} = 1.5282$ 1-Methyl-5-(3-cyclohexylcarbonylpropyl)thio-1,2,3,4-tetrazole, colorless liquid, $n_D^{12} = 1.5267$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-(3-acetylpropyl)thio-1,2,3,4-tetrazole, colorless liquid, $n_D^{20} = 1.5194$ 1-Methyl-5-(3-pentanoylpropyl)thio-1,2,3,4-tetrazole, colorless liquid, $n_D^{23.5} = 1.5059$ 1-Methyl-5-(3-cyclopentylcarbonylpropyl)thio-1,2,3,4-tetrazole, colorless liquid, $n_D^{25} = 1.5256$

EXAMPLE 74

2-(4-Ethylphenyl)-1,3-dithian (2.3 g) is dissolved in dried tetrahydrofuran (20 ml) and cooled to −78° C. To the mixture is added dropwise 1.6 N solution of n-butyllithium in n-hexane (6.5 ml) with stirring in argon gas flow. The mixture is stirred at −78° C. for 30 minutes. To the mixture is added dropwise a solution of 1-methyl-5-(3-chloropropyl)thio-1,2,3,4-tetrazole (1.9 g) in dried tetrahydrofuran (5 ml). After stirring at −78° C. for 1 hour, the mixture is stirred 4 hours while it is heated slowly to 0° C. The reaction mixture is poured into ice-water and extracted with ether. The ether solution is washed with water and saturated aqueous sodium chloride and dried over magnesium sulfate. After ether is distilled off, the residue is dissolved in acetonitrile (20 ml). Silver nitrate (7 g) and N-chlorosuccinimide (4.9 g) are dissolved in a mixture of water (40 ml) and acetonitrile (100 ml). To the mixture is added dropwise the dithian solution as above-mentioned with stirring at 0° C. in nitrogen gas flow. After stirring at 0° C. for 30 minutes, the mixture is heated to room temperature and further stirred for 30 minutes. The reaction mixture is diluted with water and extracted with chloroform. The chloroform solution is washed with water and saturated aqueous sodium chloride and dried over magnesium sulfate. After chloroform is distilled off, the residue is purified by column chromatography (Kieselgel 60) and eluted with benzene-ether (10:1) to give 1-methyl-5-[3-(4-ethylbenzoyl)propyl]thio-1,2,3,4-tetrazole (0.4 g) as colorless needles (recrystallized from hexane-ether), m.p. 68°–69° C.

EXAMPLE 75

In the same manner as described in Example 74, the following compounds are prepared.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-methoxybenzoyl)propyl]thio-1,2,3,4-tetrazole, colorless flakes (recrystallized from hexane-ethyl acetate), m.p. 107°–108° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25} = 1.5610$ 1-Methyl-5-[3-($\beta$-phenethylcarbonyl)propyl]thio-1,2,3,4-tetrazole, colorless liquid, $n_D^{25.5} = 1.5561$

EXAMPLE 76

2-(2-Pyridyl)-1,3-dithian (2.0 g) is dissolved in dried tetrahydrofuran (20 ml) and cooled to −78° C. To the mixture is added dropwise 1.6 N solution of n-butyllithium in n-hexane (6.5 ml) with stirring in argon gas flow. The mixture is stirred at −78° C. for 30 minutes. To the mixture is added dropwise a solution of 1-methyl-5-(3-chloropropyl)thio-1,2,3,4-tetrazole (1.9 g) in dried tetrahydrofuran (5 ml). After stirring at −78° C. for 1 hour, the mixture is stirred 4 hours while it is heated slowly to 0° C. The reaction mixture is poured into ice-water and extracted with ether. The ether solution is washed with water and saturated aqueous sodium chloride and dried over magnesium sulfate. After ether is distilled off, the residue is dissolved in acetonitrile (20 ml). Silver nitrate (7 g) and N-chlorosuccinimide (4.9 g) are dissolved in a mixture of water (40 ml) and acetonitrile (100 ml). To the mixture is added dropwise the dithian solution as above-mentioned with stirring at 0° C. in nitrogen gas flow. After stirring at 0° C. for 30 minutes, the mixture is heated to room temperature and further stirred for 30 minutes. The reaction mixture is diluted with water and extracted with chloroform. The chloroform solution is washed with water and saturated aqueous sodium chloride and dried over magnesium sulfate. After chloroform is distilled off, the residue is purified by column chromatography (Kieselgel 60) and eluted with benzene-ether (10:1) to give 1-methyl-5-[3-(2-pyridylcarbonyl)propyl]thio-1,2,3,4-tetrazole (0.4 g) as colorless needles (recrystallized from hexane-ether), m.p. 73°–75° C.

EXAMPLE 77

In the same manner as described in Example 76, the following compounds are prepared.

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recristallized from hexane-ether), m.p. 67°–68.5° C.

EXAMPLE 78

(a) Thionyl chloride (5 ml) is added to 4-(1-methyl-1,2,3,4-tetrazol-5-yl)thio-butyric acid (2 g) and the mixture is stirred at 40°–50° C. for 1 hour. An excess of thionyl chloride is distilled off under reduced pressure. Dried benzene is added to the mixture and water is distilled off by azeotropic distillation, and the obtained mixture is supplied to the following reaction as it is.

(b) Copper iodide (571 mg) is added into a closed two-necked distillation flask. After degassing under reduced pressure, the flask is filled with nitrogen gas. Absolute ether (10 ml) is poured into the flask and the whole is cooled to −40° C. Into the flask is added 1.32 M solution of ethyllithium in ether (5 ml). After stirring at −40° C. for 5 minutes, the mixture is cooled to −78° C. Into the mixture is poured into a cooled solution of 4-(1-methyl-1,2,3,4-tetrazol-5-yl)thio-butyryl chloride (230 mg), which is obtained in the above (a), in absolute ether (5 ml) and the mixture is stirred at −78° C. for 15 minutes. Absolute methanol (35 ml) is poured into the mixture and the temperature of the flask is brought back to room temperature. The reaction mixture is poured into saturated aqueous ammonium chloride and extracted with ether. After the ether solution is dried over magnesium sulfate, ether is distilled off. The residue is purified by column chromatography (Kieselgel 60) and eluted with benzene-ether (10:1) to give 1-methyl-5-(3-propionylpropyl)thio-1,2,3,4-tetrazole (0.1 g) as colorless liquid, $n_D^{25}=1.5042$

EXAMPLE 79

In the same manner as described in Example 78, the following compounds are prepared.

1-phenyl-5-(3-benzoylpropyl)thio-1,2,3,4-tetrazole, colorless granules (recrystallized from methanol-water), m.p. 71°–72° C.

1-Cyclohexyl-5-(3-cyclohexylcarbonylpropyl)thio-1,2,3,4-tetrazle, pale yellow liquid $n_D^{12}=1.5282$ 1-Methyl-5-acetylmethylthio-1,2,3,4-tetrazole, colorless needles (recrystallized from methanol-ether), m.p. 31° C.

1-Methyl-5-(3-cyclohexylcarbonylpropyl)thio-1,2,3,4-tetrazole, colorless liquid, $n_D^{12}=1.5267$ 1-Methyl-5-(3-benzoylpropyl)thio-1,2,3,4-tetrazole, colorless needles (recrystallized from methanol-water), m.p. 57.5°–58° C.

1-Phenyl-5-(3-cyclohexylcarbonylpropyl)thio-1,2,3,4-tetrazole, colorless granules (recrystallized from methanol-water), m.p. 57.5°–58.5° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-(3-acetylpropyl)thio-1,2,3,4-tetrazole, colorless liquid, $n_D^{20}=1.5194$ 1-Methyl-5-(3-pentanoylpropyl)thio-1,2,3,4-tetrazole, colorless liquid, $n_D^{23.5}=1.5059$ 1-Methyl-5-(3-cyclopentylcarbonylpropyl)thio-1,2,3,4-tetrazole, colorless liquid, $n_D^{25}=1.5256$

EXAMPLE 80

(a) Thionyl chloride (5 ml) is added to 1-methyl-5-(3-carboxypropyl)thio-1,2,3,4-tetrazole (2 g) and the mixture is stirred at 40°–50° C. for 1 hour. An excess of thionyl chloride is distilled off under reduced pressure. Dried benzene is added to the mixture and water is distilled off by azeotropic distillation, and the obtained mixture is supplied to the following reaction as it is.

(b) Copper iodide (571 mg) is added into a closed two-necked distillation flask. After degassing under reduced pressure, the flask is filled with nitrogen gas. Absolute ether (10 ml) is poured into the flask and the whole is cooled to −40° C. Into the flask is added 1.32 M solution of 4-ethylphenyllithiun in ether (5 ml). After stirring at −40° C. for 5 minutes, the mixture is cooled to −78° C. Into the mixture is poured into a cooled solution of 4-(1-methyl-1,2,3,4-tetrazol-5-yl)thio-butyryl chloride (230 mg), which is obtained in the above (a), in absolute ether (5 ml) and the mixture is stirred at −78° C. for 15 minutes. Absolute methanol (35 ml) is poured into the mixture and the temperature of the flask is brought back to room temperature. The reaction mixture is poured into saturated aqueous ammonium chloride and extracted with ether. After the ether solution is dried over magnesium sulfate, ether is distilled off. The residue is purified by column chromatography (Kieselgel 60) and eluted with benzene-ether (10:1) to give 1-methyl-5-[3-(4-ethylbenzoyl)propyl]thio-1,2,3,4-tetrazole (0.1 g) as colorless needles (recrystallized from hexane-ether), m.p. 68°–69° C.

EXAMPLE 81

In the same manner as described in Example 80, the following compounds are prepared.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-methoxybenzoyl)propyl]thio-1,2,3,4-tetrazole, colorless flakes (recrystallized from hexane-ethyl acetate), m.p. 107°–108° C.

1-Methyl-5-[3-(2-naphthoyl)propyl]thio-1,2,3,4-tetrazole, colorless prisms (recrystallized from ethanol), m.p. 118°–120° C.

1-Methyl-5-[3-(benzylcarbonyl)propyl]thio-1,2,3,4-tetrazole, colorless liquid, $n_D^{25}=1.5610$ 1-Methyl-5-[3-(β-phenethylcarbonyl)propyl]thio-1,2,3,4-tetrazole, colorless liquid, $n_D^{25.5}=1.5561$

EXAMPLE 82

(a) Thionyl chloride (5 ml) is added to 1-methyl-5-(3-carboxypropyl)thio-1,2,3,4-tetrazole (2 g) and the mixture is stirred at 40°–50° C. An excess of thionyl chloride is distilled off under reduced pressure. Dried benzene is added to the mixture and water is distilled off by azeotropic distillation, and the obtained mixture is supplied to the following reaction as it is.

(b) Copper iodide (571 mg) is added into a closed two-necked distillation flask. After degassing under reduced pressure, the flask is filled with nitrogen gas. Absolute ether (10 ml) is poured into the flask and the whole is cooled to −40° C. Into the flask is added 1.32 M solution of 2-pyridyllithium in ether (5 ml). After stirring at −40° C. for 5 minutes, the mixture is cooled to −78° C. Into the mixture is poured into a cooled solution of 4-(1-methyl-1,2,3,4-tetrazol-5-yl)thio-butyryl chloride (230 mg), which is obtained in the above (a), in absolute ether (5 ml) and the mixture is stirred at −78° C. for 15 minutes. Absolute methanol (35 ml) is poured into the mixture and the temperature of the flask is brought back to room temperature. The reaction mixture is poured into saturated aqueous ammonium chloride and extracted with ether. After the ether solution is dried over magnesium sulfate, ether is distilled off. The residue is purified by column chromatography (Kieselgel 60) and eluted with benzene-ether (10:1) to give 1-methyl-5-[3-(2-pyridylcarbonyl)propyl]thio-1,2,3,4-tetrazole (0.1 g) as colorless needles (recrystallized from hexane-ether), m.p. 73°–75° C.

EXAMPLE 83

In the same manner as described in Example 82, the following compounds are prepared.

1-Methyl-5-[3-(2-thenoyl)propyl]thio-1,2,3,4-tetrazole, colorless needles (recrystallized from hexane-ether), m.p. 55°–56° C.

1-Methyl-5-[3-(2-furoyl)propyl]thio-1,2,3,4-tetrazole, colorless needles (recrystallized from hexane-ether), m.p. 41°–42° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recristallized from hexane-ether), m.p. 67°–68.5° C.

EXAMPLE 84

1-Methyl-5-[3-(4-methoxybenzoyl)propyl]thio-1,2,3,4-tetrazole (2 g) is added to 47% hydrobromic acid (40 ml) and the mixture is refluxed for 5 hours. After cooling, the mixture is poured into ice-water and extracted with ethyl acetate. The organic layer is washed with water and saturated aqueous sodium chloride and dried over magnesium sulfate. After ethyl acetate is distilled off, the residue is purified by silica gel column chromatography (Wakogen C-200) and eluted with hexane-ethyl acetate (1:1) to give 1-methyl-5-[3-(4-hydroxybenzoyl)propyl]thio-1,2,3,4-tetrazole (0.3 g) as colorless needles (recrystallized from water), m.p. 128.5°–129.5° C.

EXAMPLE 85

Aluminum chloride (16 g) is suspended in carbon tetrachloride (100 ml) and 4-(1-methyl-1,2,3,4-tetrazol-5-yl)thio-butyryl chloride (26.5 g) is added dropwise to the suspension under ice-cooling. After the mixture is stirred for 30 minutes, benzene (7.8 g) is added dropwise to the mixture at lower than 5° C. and the mixture is stirred at the same temperature for 1 hour. The reaction mixture is poured into hydrochloric acid-ice and extracted with chloroform. The chloroform solution is washed with saturated aqueous sodium bicarbonate and saturated aqueous sodium chloride and dried over magnesium sulfate. After chloroform is distilled off, the residue is purified by column chromatography (Kieselgel 60, eluting agent, chloroform). The resulting eluate is recrystallized from methanol-water to give 1-methyl-5-(3-benzoylpropyl)thio-1,2,3,4-tetrazole (10.5 g) as colorless needles, m.p. 57.5°–58° C.

EXAMPLE 86

In the same manner as described in Example 85, the following compounds are prepared.

1-Phenyl-5-(3-benzoylpropyl)thio-1,2,3,4-tetrazole, colorless granules (recrystallized from methanol-water), m.p. 71°–72° C.

1-Methyl-5-[3-(4-ethylbenzoyl)propyl]thio-1,2,3,4-tetrazole, colorless needles (recrystallized from hexane-ether), m.p. 68°–69° C.

1-Methyl-5-benzoylmethylthio-1,2,3,4-tetrazole, colorless granules (recrystallized from methanol), m.p. 130.5°–131.5° C.

1-Methyl-5-(2-benzoylethyl)thio-1,2,3,4-tetrazole, colorless plates (recrystallized from ligroin), m.p. 78°–80° C.

1-Methyl-5-(4-benzoylbutyl)thio-1,2,3,4-tetrazole, colorless flakes (recrystallized from methanol-water), m.p. 72°–73.5° C.

1-Methyl-5-(5-benzoylpentyl)thio-1,2,3,4-tetrazole, colorless plates (recrystallized from hexane-ether), m.p. 44° C.

1-Methyl-5-[3-(4-acetylaminobenzoyl)propyl]thio-1,2,3,4-tetrazole, colorless needles (recrystallized from ethanol), m.p. 170°–172° C.

1-Methyl-5-[3-(3,4-dimethoxybenzoyl)propyl]thio-1,2,3,4-tetrazole, colorless prisms (recrystallized from hexane-ethyl acetate), m.p. 86°–87° C.

1-Methyl-5-[3-(4-chlorobenzoyl)propyl]thio-1,2,3,4-tetrazole, colorless prisms (recrystallized from methanol-water), m.p. 139°–140° C.

1-Methyl-5-[3-(4-methoxybenzoyl)propyl]thio-1,2,3,4-tetrazole, colorless flakes (recrystallized from hexane-ethyl acetate), m.p. 107°–108° C.

1-Methyl-5-[3-(4-hydroxybenzoyl)propyl]thio-1,2,3,4-tetrazole, colorless needles (recrystallized from water), m.p. 128.5°–129.5° C.

1-Methyl-5-[3-(2-naphthoyl)propyl]thio-1,2,3,4-tetrazole, colorless prisms (recrystallized from ethanol), m.p. 118°–120° C.

EXAMPLE 87

Aluminum chloride (4 g) is suspended in carbon disulfide (20 ml) and furan (1.5 g) is added to the suspension. 4-(1-Methyl-1,2,3,4-tetrazol-5-yl)thiobutyryl chloride (4.4 g) added dropwise to the mixture with stirring under ice-cooling, and the mixture is stirred at the same temperature for 1 hour. The reaction mixture is poured into hydrochloric acid-ice and extracted with chloroform. The chloroform solution is washed with saturated aqueous sodium bicarbonate and saturated aqueous sodium chloride and dried over magnesium sulfate. After chloroform is distilled off, the residue is purified by column chromatography (Wakogel C-200, eluting agent, chloroform), the eluate is recrystallized from hexane-ether to give 1-methyl-5-[3-(2-furoyl)propyl]thio-1,2,3,4-tetrazole (0.8 g) as colorless needles, m.p. 41°–42° C.

EXAMPLE 88

In the same manner as described in Example 87, the following compounds are prepared.

1-Methyl-5-[3-(2-thenoyl)propyl]thio-1,2,3,4-tetrazole, colorless needles (recrystallized from hexane-ether), m.p. 55°–56° C.

1-Methyl-5-[3-(5-methyl-2-thenoyl)propyl]thio-1,2,3,4-tetrazole, pale yellow needles (recrystallized from hexane-ethyl acetate), m.p. 78°–80° C.

1-Methyl-5-[3-(5-chloro-2-thenoyl)propyl]thio-1,2,3,4-tetrazole, pale yellow needles (recrystallized from hexane-ethyl acetate), m.p. 91°–92° C.

1-Methyl-5-[3-(2-pyrrolylcarbonyl)propyl]thio-1,2,3,4-tetrazole, pale yellow prisms (recrystallized from hexane-ethyl acetate), m.p. 94°–96° C.

1-Methyl-5-[3-(2,5-dimethyl-3-furoyl)propyl]thio-1,2,3,4-tetrazole, colorless plates (recristallized from hexane-ether), m.p. 67°–68.5° C.

1-Methyl-5-{3-[(3,4-dihydrocarbostyril-6-yl)carbonyl]propyl}thio-1,2,3,4-tetrazole, colorless needles (recrystallized from ethanol), m.p. 188°–190° C.

1-Methyl-5-{3-[(1-methyl-3,4-dihydrocarbostyril-6-yl)carbonyl]propyl}thio-1,2,3,4-tetrazole, colorless needles (recrystallized from hexane-ethyl acetate), m.p. 110°–113.5° C.

EXAMPLE 89

1-Methyl-5-(3-chloropropyl)thio-1,2,3,4-tetrazole (1.9 g) and thiophenol (1.1 g) are dissolved in acetone (50 ml). To the mixture are added potassium carbonate (1.5 g) and potassium iodide (0.1 g), and the mixture is refluxed for 3 hours. After acetone is distilled off, water is added to the residue, and the mixture is extracted with ether. The ether solution is washed with diluted aqueous sodium hydroxide and saturated aqueous sodium chloride and dried over sodium sulfate. After ether is distilled off, the residue is purified by silica gel column chromatography (Kieselgel 60), followed by eluting with benzene-chloroform (3:2) to give 1-methyl-5-(3-phenylthiopropyl)thio-1,2,3,4-tetrazole (2.5 g) as colorless liquid, $n_D^{18} = 1.6008$.

Elemental analysis for $C_{11}H_{14}N_4S_2$: Calcd (%): C, 49.60; H, 5.30; N, 21.03. Found (%): C, 49.34; H, 5.12; N, 20.85.

EXAMPLE 90

In the same manner as described in Example 89, the following compounds are prepared.

1-Methyl-5-(3-cyclohexylthiopropyl)thio-1,2,3,4-tetrazole, colorless liquid, $n_D^{18} = 1.5433$ 1-Methyl-5-[3-(2-pyridyl)thiopropyl]thio-1,2,3,4-tetrazole, pale yellow liquid, $n_D^{18} = 1.6022$ 1-Cyclohexyl-5-(3-ethylthiopropyl)thio-1,2,3,4-tetrazole, colorless liquid, $n_D^{14} = 1.5433$ 1-Methyl-5-[3-(1-methyl-1,2,3,4-tetrazol-5-yl)thiopropyl]thio-1,2,3,4-tetrazole, colorless prisms (recrystallized from ethanol), m.p. 141.5°-143.5° C.

1-Methyl-5-[4-(1-methyl-1,2,3,4-tetrazol-5-yl)thiobutyl]thio-1,2,3,4-tetrazole, colorless needles (recrystallized from ethanol), m.p. 122°-123° C.

1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°-128.5° C.

1-Methyl-5-[3-(1-cyclohexyl-1,2,3,4-tetrazol-5-yl)thiopropyl]thio-1,2,3,4-tetrazole, pale yellow liquid, $n_D^{18} = 1.5653$ 1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°-82° C.

1-Methyl-2-[3-(1-methylimidazol-2-yl)thiopropyl]thio-1,2,3,4-tetrazole, colorless needles (recrystallized from ether), m.p. 59.5°-60.5° C.

EXAMPLE 91

1-Methyl-5-(3-chloropropyl)thio-1,2,3,4-tetrazole (1.9 g) and 3-hydroxy-2-mercaptopyridine (1.3 g) are dissolved in acetone (50 ml). To the mixture are added potassium carbonate (1.4 g) and potassium iodide (0.1 g), and the mixture is refluxed for 5 hours. After acetone is distilled off, water is added to the residue, and the mixture is extracted with chloroform. The chloroform solution is washed with saturated aqueous sodium chloride and dried over magnesium sulfate. After chloroform is distilled off, the residue is purified by column chromatography (Kieselgel 60), followed by eluting with chloroform-methanol and recrystallizing from ethyl acetate-n-hexane to give 1-methyl-5-[3-(3-hydroxy-2-pyridyl)thiopropyl]thio-1,2,3,4-tetrazole (1.2 g) as pale yellow granules, m.p. 87.5°-88.5° C.

Elemental analysis for $C_{10}H_{13}N_5OS_2$: Calcd (%): C, 42.40; H, 4.59; N, 24.73. Found (%): C, 42.29; H, 4.70; N, 24.66.

EXAMPLE 92

In the same manner as described in Example 91, the following compounds are prepared.

1-Methyl-5-[2-(2-pyridyl)thioethyl]thio-1,2,3,4-tetrazole, colorless prisms, m.p. 77°-79.5° C. (ethanol)

1-Methyl-5-[4-(2-pyridyl)thiobutyl]thio-1,2,3,4-tetrazole, pale yellow prisms, m.p. 49°-51.5° C. (ethanol-water)

1-Methyl-5-[5-(2-pyridyl)thiopentyl]thio-1,2,3,4-tetrazole, colorless liquid, $n_D^{19} = 1.5853$ 1-Methyl-5-[6-(2-pyridyl)thiohexyl]thio-1,2,3,4-tetrazole, colorless prisms, m.p. 58°-60° C. (ethanol)

1-Methyl-5-[3-(4-methyl-2-pyrimidyl)thiopropyl]thio-1,2,3,4-tetrazole, colorless liquid, $n_D^{25.5} = 1.5853$ 1-Methyl-2-[4-(1-methyl-1,2,3,4-tetrazol-5-yl)thiobutyl]isothiourea hydrobromide, white powdery crystals (acetone), m.p. 116.5°-118° C. (decomp.)

1-Methyl-5-[3-(2-benzimidazolyl)thiopropyl]thio-1,2,3,4-tetrazole, colorless needles (ethanol), m.p. 137°-139° C.

1-Methyl-5-[3-(3,5-di-tert-butyl-4-hydroxyphenyl)thiopropyl]thio-1,2,3,4-tetrazole, pale yellow needles (methanol-water), m.p. 76°-77° C.

1-Methyl-5-[3-(5-amino-1,3,4-thiadiazol-2-yl)thiopropyl]thio-1,2,3,4-tetrazole, colorless prisms (ethanol), m.p. 120.5°-122° C.

1-Methyl-5-[3-(5-methyl-1,3,4-oxadiazol-2-yl)thiopropyl]thio-1,2,3,4-tetrazole, colorless liquid, $n_D^{25.5} = 1.5644$ 1-Methyl-5-[3-(β-naphthyl)thiopropyl]thio-1,2,3,4-tetrazole, colorless needles (ethanol), m.p. 56°-58° C.

1-Methyl-5-[3-(2-quinolyl)thiopropyl]thio-1,2,3,4-tetrazole, pale yellow needles (methanol), m.p. 87°-89° C.

1-Methyl-5-(4-phenylthiobutyl)thio-1,2,3,4-tetrazole, colorless prisms (ethanol) m.p. 51.5°-53° C.

1-Methyl-5-[4-(2-carboxyphenyl)thiobutyl]thio-1,2,3,4-tetrazole, pale yellow prisms (ethanol), m.p. 143.5°-144.5° C.

1-Methyl-5-[4-(2-methylphenyl)thiobutyl]thio-1,2,3,4-tetrazole, colorless liquid, $n_D^{29} = 1.5786$ 1-Methyl-5-[4-(2-aminophenyl)thiobutyl]thio-1,2,3,4-tetrazole, yellow liquid, $n_D^{29} = 1.5961$ 1-Methyl-5-[4-(4-chlorophenyl)thiobutyl]thio-1,2,3,4-tetrazole, colorless liquid, $n_D^{29} = 1.5971$ 1-Methyl-5-[3-(2-furylmethyl)thiopropyl]thio-1,2,3,4-tetrazole, brown liquid, $n_D^{26.5} = 1.5641$ 1-Methyl-5-(3-benzylthiopropyl)thio-1,2,3,4-tetrazole, colorless liquid, $n_D^{26.5} = 1.5856$ 1-Methyl-5-[3-(4-chlorobenzyl)thiopropyl]thio-1,2,3,4-tetrazole, colorless liquid, $n_D^{29} = 1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°-77° C.

1-Methyl-5-[3-(quinazolin-4-on-2-yl)thiopropyl]thio-1,2,3,4-tetrazole, colorless scales (ethanol-hexane), m.p. 132.5°-134.5° C.

1-Methyl-5-[4-(3H,4H-1,3,4-benzotriazepin-5-on-2-yl)thiobutyl]thio-1,2,3,4-tetrazole, colorless prisms, m.p. 94°-95° C. (methanol)

1-Methyl-5-(3-ethylthiopropyl)thio-1,2,3,4-tetrazole, colorless liquid, $n_D^{29} = 1.5385$ 1-Methyl-5-(3-n-butylthiopropyl)thio-1,2,3,4-tetrazole, yellow liquid, $n_D^{29} = 1.5192$ 1-Methyl-5-(3-cyclopentylthiopropyl)thio-1,2,3,4-tetrazole, pale yellow liquid, $n_D^{29}=1.5469$ 1-Methyl-5-[3-(2-pyridylmethyl)thiopropyl]thio-1,2,3,4-tetrazole, brown liquid, $n_D^{29}=1.5820$ 1-Methyl-5-[3-(4-methyl-2-thiazolyl)thiopropyl]thio-1,2,3,4-tetrazole, colorless liquid, $n_D^{29}=1.5919$ 1-Methyl-5-[3-(4-pyridyl)thiopropyl]thio-1,2,3,4-tetrazole, pale yellow liquid, $n_D^{26}=1.6017$ 1-Methyl-5-[3-(5-nitro-2-pyridyl)thiopropyl]thio-1,2,3,4-tetrazole, pale brown liquid, $n_D^{29}=1.6289$ 1-Methyl-5-[3-(2-amino-4-methyl-6-pyrimidyl)thiopropyl]thio-1,2,3,4-tetrazole, colorless powdery crystals (methanol), m.p. 119°–120° C.

1-Methyl-5-[2-(2-furylmethyl)thioethyl]thio-1,2,3,4-tetrazole, pale brown liquid, $n_D^{29}=1.5711$ 1-Methyl-5-{3-[(2-amino-4-thiazolyl)methyl]thiopropyl}thio-1,2,3,4-tetrazole, yellow prisms (methanol-water), m.p. 117°–118.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°–89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°–90.5° C.

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

1-Methyl-5-[2-methyl-3-(2-pyridyl)thiopropyl]thio-1,2,3,4-tetrazole, pale yellow liquid, $n_D^{25.5}=1.5936$ 1-Methyl-5-[4-(4-methoxyphenyl)thiobutyl]thio-1,2,3,4-tetrazole, colorless liquid, NMR (90 MHz, CDCl$_3$): δ1.50–2.20 (4H, m), 2.83 (2H, t, J=6 Hz), 3.30 (2H, t, J=6 Hz), 3.77 (3H, s), 3.87 (3H, s) 6.82 (2H, d, J=9 Hz), 7.32 (2H, d, J=9 Hz)

EXAMPLE 93

1-Methyl-5-mercapto-1,2,3,4-tetrazole (4.6 g) and 1,3-dibromopropane (4 g) are dissolved in acetone (50 ml). To the mixture is added potassium carbonate (5.5 g), and the mixture is refluxed for 3 hours. After acetone is distilled off, water is added to the residue, and the precipitated crystals are separated by filtration and recrystallized from ethanol to give 1-methyl-5-[3-(1-methyl-1,2,3,4-tetrazol-5-yl)thiopropyl]thio-1,2,3,4-tetrazole (3.6 g) as colorless prisms, m.p. 141.5°–143.5° C.

Elemental analysis for $C_7H_{12}N_8S_2$: Calcd (%): C, 30.87; H, 4.44; N, 41.14. Found (%): C, 30.68; H, 4.37; N, 41.32.

EXAMPLE 94

In the same manner as described in Example 93, the following compounds are prepared.

1-Methyl-5-[4-(1-methyl-1,2,3,4-tetrazol-5-yl)thiobutyl]thio-1,2,3,4-tetrazole, colorless needles (recrystallized from ethanol), m.p. 122°–123° C.

1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°–82° C.

1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°–128.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°–89.5° C.)

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

EXAMPLE 95

1-Methyl-5-(3-mercaptopropyl)thio-1,2,3,4-tetrazole (1.9 g) is dissolved in 1 N aqueous sodium hydroxide (30 ml), and thereto is added dropwise a solution of cyclohexyl bromide (2.0 g) in acetone (20 ml) with stirring under ice-cooling. After the addition, the mixture is stirred at room temperature for 3 hours. Acetone is distilled off and water is added to the residue, and the mixture is extracted with ether. The ether solution is washed with diluted aqueous sodium hydroxide and saturated aqueous sodium chloride, and dried over sodium sulfate. After ether is distilled off, the residue is purified by column chromatography (Kieselgel 60), followed by eluting with n-hexane-ether (4:1) to give 1-methyl-5-(3-cyclohexylthiopropyl)thio-1,2,3,4-tetrazole (1.5 g), colorless liquid, $n_D^{18}=1.5433$.

Elemental analysis for $C_{11}H_{20}N_4S_2$: Calcd (%): C. 48.53; H, 7.35: N, 20.59. Found (%): C, 48.40; H, 7.58; N, 20.41.

EXAMPLE 96

In the same manner as described in Example 95, there is prepared 1-cyclohexyl-5-(3-ethylthiopropyl)thio-1,2,3,4-tetrazole, colorless liquid, $n_D^{14}=1.5433$.

EXAMPLE 97

1-Methyl-5-(3-mercaptopropyl)thio-1,2,3,4-tetrazole (1.9 g) is dissolved in 1 N aqueous sodium hydroxide (30 ml), and thereto is added dropwise a solution of 5-nitro-2-chloropyridine (1.9 g) in acetone (20 ml) under ice-cooling. After the addition, the mixture is stirred at room temperature for 3 hours. Acetone is distilled off and water is added to the residue. The mixture is extracted with ether, and the ether solution is washed with diluted aqueous sodium hydroxide and saturated aqueous sodium chloride and dried over sodium sulfate. After ether is distilled off, the residue is purified by column chromatography (Kieselgel 60), followed by eluting with n-hexane-ether (4:1) to give 1-methyl-5-[3-(5-nitro-2-pyridyl)thiopropyl]thio-1,2,3,4-tetrazole (1.4 g), pale brown liquid, $n_D^{29}=1.6289$.

Elemental analysis for $C_{10}H_{12}N_6O_2$: Calcd (%): C, 38.46; H, 3.85; N, 26.92. Found (%): C, 38.46; H, 3.68; N, 27.01.

EXAMPLE 98

In the same manner as described in Example 97, the following compounds are prepared.

1-Methyl-5-[3-(2-pyridyl)thiopropyl]thio-1,2,3,4-tetrazole, pale yellow liquid, $n_D^{18}=1.6022$ 1-Methyl-5-[4-(2-pyridyl)thiobutyl]thio-1,2,3,4-tetrazole, pale yellow prisms, m.p. 49°–51.5° C. (ethanol-water)

1-Methyl-5-[5-(2-pyridyl)thiopentyl]thio-1,2,3,4-tetrazole, colorless liquid, $n_D^{19}=1.5853$ 1-Methyl-5-[6-(2-pyridyl)thiohexyl]thio-1,2,3,4-tetrazole, colorless prisms, m.p. 58°–60° C. (ethanol)

1-Methyl-5-[3-(3-hydroxy-2-pyridyl)thiopropyl]thio-1,2,3,4-tetrazole, pale yellow granules, m.p. 87.5°–88.5° C.

1-Methyl-5-[3-(4-methyl-2-pyrimidyl)thiopropyl]thio-1,2,3,4-tetrazole, colorless liquid, $n_D^{25.5}=1.5853$ 1-Methyl-5-[3-(2-benzimidazolyl)thiopropyl]thio-1,2,3,4-tetrazole, colorless needles (ethanol), m.p. 137°–139° C.

1-Methyl-5-[3-(3,5-di-tert-butyl-4-hydroxyphenyl)thiopropyl]thio-1,2,3,4-tetrazole, pale yellow needles (methanol-water), m.p. 76°–77° C.

1-Methyl-5-[3-(5-amino-1,3,4-thiadiazol-2-yl)thiopropyl]thio-1,2,3,4-tetrazole, colorless prisms (ethanol), m.p. 120.5°–122° C.

1-Methyl-5-[3-(5-methyl-1,3,4-oxadiazol-2-yl)thiopropyl]thio-1,2,3,4-tetrazole, colorless liquid, $n_D^{25.5}=1.5644$ 1-Methyl-5-[3-(β-naphthyl)thiopropyl]thio-1,2,3,4-tetrazole, colorless needles (ethanol), m.p. 56°–58° C.

1-Methyl-5-[3-(2-quinolyl)thiopropyl]thio-1,2,3,4-tetrazole, pale yellow needles (methanol), m.p. 87°–89° C.

1-Methyl-5-(4-phenylthiobutyl)thio-1,2,3,4-tetrazole, colorless prisms (ethanol) m.p. 51.5°–53° C.

1-Methyl-5-[4-(2-carboxyphenyl)thiobutyl]thio-1,2,3,4-tetrazole, pale yellow prisms (ethanol), m.p. 143.5°–144.5° C.

1-Methyl-5-[4-(2-methylphenyl)thiobutyl]thio-1,2,3,4-tetrazole, colorless liquid, $n_D^{29}=1.5786$ 1-Methyl-5-[4-(2-aminophenyl)thiobutyl]thio-1,2,3,4-tetrazole, yellow liquid, $n_D^{29}=1.5961$ 1-Methyl-5-[4-(4-chlorophenyl)thiobutyl]thio-1,2,3,4-tetrazole, colorless liquid, $n_D^{29}=1.5971$ 1-Methyl-5-[3-(2-furylmethyl)thiopropyl]thio-1,2,3,4-tetrazole, brown liquid, $n_D^{26.5}=1.5641$ 1-Methyl-5-(3-benzylthiopropyl)thio-1,2,3,4-tetrazole, colorless liquid, $n_D^{26.5}=1.5856$ 1-Methyl-5-[3-(4-chlorobenzyl)thiopropyl]thio-1,2,3,4-tetrazole, colorless liquid, $n_D^{29}=1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°–77° C.

1-Methyl-5-[3-(quinazolin-4-on-2-yl)thiopropyl]thio-1,2,3,4-tetrazole, colorless scales (ethanol-hexane), m.p. 132.5°–134.5° C.

1-Methyl-5-[4-(3H,4H-1,3,4-benzotriazepin-5-on-2-yl)thiobutyl]thio-1,2,3,4-tetrazole, colorless prisms, m.p. 94°–95° C. (methanol)

1-Methyl-5-(3-ethylthiopropyl)thio-1,2,3,4-tetrazole, colorless liquid, $n_D^{29}=1.5385$ 1-Methyl-5-(3-n-butylthiopropyl)thio-1,2,3,4-tetrazole, yellow liquid, $n_D^{29}=1.5192$ 1-Methyl-5-(3-cyclopentylthiopropyl)thio-1,2,3,4-tetrazole, pale yellow liquid, $n_D^{29}=1.5469$ 1-Methyl-5-[3-(2-pyridylmethyl)thiopropyl]thio-1,2,3,4-tetrazole, brown liquid, $n_D^{29}=1.5820$ 1-Methyl-5-[3-(4-methyl-2-thiazolyl)thiopropyl]thio-1,2,3,4-tetrazole, colorless liquid, $n_D^{29}=1.5919$ 1-Methyl-5-[3-(4-pyridyl)thiopropyl]thio-1,2,3,4-tetrazole, pale yellow liquid, $n_D^{26}=1.6017$ 1-Methyl-5-[3-(2-amino-4-methyl-6-pyrimidyl)thiopropyl]thio-1,2,3,4-tetrazole, colorless powdery crystals (methanol), m.p. 119°–120° C.

1-Methyl-5-[2-(2-furylmethyl)thioethyl]thio-1,2,3,4-tetrazole, pale brown liquid, $n_D^{29}=1.5711$ 1-Methyl-5-{3-[(2-amino-4-thiazolyl)methyl]thiopropyl}thio-1,2,3,4-tetrazole, yellow prisms (methanol-water), m.p. 117°–118.5° C.

1-Cyclohexyl-5-[3-(1-cyclhexyl-1,2,3,4-tetrazol-5-yl)thiopropyl]thio-1,2,3,4-tetrazole, pale yellow granules (ether-ethanol), m.p. 88.5°–89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°–90.5° C.

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

1-Methyl-5-[2-methyl-3-(2-pyridyl)thiopropyl]thio-1,2,3,4-tetrazole, pale yellow liquid, $n_D^{25.5}=1.5936$ 1-Methyl-5-[4-(4-methoxyphenyl)thiobutyl]thio-1,2,3,4-tetrazole, colorless liquid, NMR (90 MHz, CDCl$_3$): δ1.50–2.20 (4H, m), 2.83 (2H, t, J=6 Hz), 3.30 (2H, t, J=6 Hz), 3.77 (3H, s) 6.82 (2H, d, J=9 Hz), 7.32 (2H, d, J=9 Hz)

EXAMPLE 99A

2-Mercaptopyridine (1.3 g) and 1-methyl-5-(4-bromobutyl)thio-1,2,3,4-tetrazole (2 g) are dissolved in acetone (50 ml). To the mixture is added potassium carbonate (1.4 g), and the mixture is refluxed for 2 hours. After acetone is distilled off, water is added to the residue, and the precipitated crystals are separated by filtration and recrystallized from ethanol-water to give 1-methyl-5-[4-(2-pyridyl)thiobutyl]thio-1,2,3,4-tetrazole (1.7 g) as pale yellow prisms, m.p. 49°–51.5° C.

Elemental analysis for $C_{11}H_{15}N_5S_2$: Calcd (%): C, 46.98; H, 5.34; N, 24.91. Found (%): C, 46.67; H, 5.27; N, 24.94.

EXAMPLE 99B

Mercaptobenzene (1.3 g) and 5-(3-bromopropyl)thio-1,2,3,4-tetrazole (1.8 g) are dissolved in acetone (50 ml), and thereto is added potassium carbonate (1.4 g), and the mixture is refluxed for 2 hours. After acetone is distilled off, water is added to the residue, and the mixture is extracted with chloroform. The chloroform layer is washed with 5% aqueous sodium hydroxide and saturated aqueous sodium chloride and dried over magnesium sulfate. After chloroform is distilled off, the residue is purified by column chromatography (Wakogel C-200, eluting agent, chloroform) to give 5-(3-phenylthiopropyl)thio-1,2,3,4-tetrazole (1.5 g) as colorless liquid.

Elemental analysis for $C_{10}H_{12}N_4S_2$: Calcd (%): C, 47.59; H, 4.79; N, 22.20. Found (%): C, 47.62; H, 4.80; N, 22.15.

EXAMPLE 100

In the same manner as described in Example 99A, the following compounds are prepared.

1-Methyl-5-(3-cyclohexylthiopropyl)thio-1,2,3,4-tetrazole, colorless liquid, $n_D^{18}=1.5433$ 1-Methyl-5-[3-(2-pyridyl)thiopropyl]thio-1,2,3,4-tetrazole, pale yellow liquid, $n_D^{18}=1.6022$ 1-Cyclohexyl-5-(3-ethylthiopropyl)thio-1,2,3,4-tetrazole, colorless liquid, $n_D^{14}=1.5433$ 1-Methyl-5-[3-(1-methyl-1,2,3,4-tetrazol-5-yl)thiopropyl]thio-1,2,3,4-tetrazole, colorless prisms (recrystallized from ethanol), m.p. 141.5°–143.5° C.

1-Methyl-5-[4-(1-methyl-1,2,3,4-tetrazol-5-yl)thiobutyl]thio-1,2,3,4-tetrazole, colorless needles (recrystallized from ethanol), m.p. 122°–123° C.

1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°–128.5° C.

1-Methyl-5-[3-(1-cyclohexyl-1,2,3,4-tetrazol-5-yl)thiopropyl]thio-1,2,3,4-tetrazole, pale yellow liquid, $n_D^{18}=1.5653$ 1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°–82° C.

1-Methyl-2-[3-(1-methylimidazol-2-yl)thiopropyl]thio-1,2,3,4-tetrazole, colorless needles (recrystallized from ether), m.p. 59.5°–60.5° C.

1-Methyl-5-(3-phenylthiopropyl)thio-1,2,3,4-tetrazole, colorless liquid, $n_D^{18}=1.6008$ 1-Methyl-5-[2-(2-pyridyl)thioethyl]thio-1,2,3,4-tetrazole, colorless prisms, m.p. 77°–79.5° C. (ethanol)

1-Methyl-5-[5-(2-pyridyl)thiopentyl]thio-1,2,3,4-tetrazole, colorless liquid, $n_D^{19}=1.5853$ 1-Methyl-5-[6-(2-pyridyl)thiohexyl]thio-1,2,3,4-tetrazole, colorless prisms, m.p. 58°–60° C. (ethanol)

1-Methyl-5-[3-(3-hydroxy-2-pyridyl)thiopropyl]thio-1,2,3,4-tetrazole, pale yellow granules, m.p. 87.5°–88.5° C. (hexane-ethyl acetate)

1-Methyl-5-[3-(4-methyl-2-pyrimidyl)thiopropyl]thio-1,2,3,4-tetrazole, colorless liquid, $n_D^{25.5}=1.5853$ 1-Methyl-2-[4-(1-methyl-1,2,3,4-tetrazol-5-yl)thiobutyl]isothiourea hydrobromide, white powdery crystals (acetone), m.p. 116.5°–118° C. (decomp.)

1-Methyl-5-[3-(2-benzimidazolyl)thiopropyl]thio-1,2,3,4-tetrazole, colorless needles (ethanol), m.p. 137°–139° C.

1-Methyl-5-[3-(3,5-di-tert-butyl-4-hydroxyphenyl)thiopropyl]thio-1,2,3,4-tetrazole, pale yellow needles (methanol-water), m.p. 76°–77° C.

1-Methyl-5-[3-(5-amino-1,3,4-thiadiazol-2-yl)thiopropyl]thio-1,2,3,4-tetrazole, colorless prisms (ethanol), m.p. 120.5°–122° C.

1-Methyl-5-[3-(5-methyl-1,3,4-oxadiazol-2-yl)thiopropyl]thio-1,2,3,4-tetrazole, colorless liquid, $n_D^{25.5}=1.5644$ 1-Methyl-5-[3-(β-naphthyl)thiopropyl]thio-1,2,3,4-tetrazole, colorless needles (ethanol), m.p. 56°–58° C.

1-Methyl-5-(3-(2-quinolyl)thiopropyl)thio-1,2,3,4-tetrazole, pale yellow needles (methanol), m.p. 87°–89° C.

1-Methyl-5-(4-phenylthiobutyl)thio-1,2,3,4-tetrazole, colorless prisms (ethanol) m.p. 51.5°–53° C.

1-Methyl-5-[4-(2-carboxyphenyl)thiobutyl]thio-1,2,3,4-tetrazole, pale yellow prisms (ethanol), m.p. 143.5°–144.5° C.

1-Methyl-5-[4-(2-methylphenyl)thiobutyl]thio-1,2,3,4-tetrazole, colorless liquid, $n_D^{29}=1.5786$ 1-Methyl-5-[4-(2-aminophenyl)thiobutyl]thio-1,2,3,4-tetrazole, yellow liquid, $n_D^{29}=1.5961$ 1-Methyl-5-[4-(4-chlorophenyl)thiobutyl]thio-1,2,3,4-tetrazole, colorless liquid, $n_D^{29}=1.5971$ 1-Methyl-5-[3-(2-furylmethyl)thiopropyl]thio-1,2,3,4-tetrazole, brown liquid, $n_D^{26.5}=1.5641$ 1-Methyl-5-(3-benzylthiopropyl)thio-1,2,3,4-tetrazole, colorless liquid, $n_D^{26.5}=1.5856$ 1-Methyl-5-[3-(4-chlorobenzyl)thiopropyl]thio-1,2,3,4-tetrazole, colorless liquid, $n_D^{29}=1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°–77° C.

1-Methyl-5-[3-(quinazolin-4-on-2-yl)thiopropyl]thio-1,2,3,4-tetrazole, colorless scales (ethanol-hexane), m.p. 132.5°–134.5° C.

1-Methyl-5-[4-(3H,4H-1,3,4-benzotriazepin-5-on-2-yl)thiobutyl]thio-1,2,3,4-tetrazole, colorless prisms, m.p. 94°–95° C. (methanol)

1-Methyl-5-(3-ethylthiopropyl)thio-1,2,3,4-tetrazole, colorless liquid, $n_D^{29}=1.5385$ 1-Methyl-5-(3-n-butylthiopropyl)thio-1,2,3,4-tetrazole, yellow liquid, $n_D^{29}=1.5192$ 1-Methyl-5-(3-cyclopentylthiopropyl)thio-1,2,3,4-tetrazole, pale yellow liquid, $n_D^{29}=1.5469$ 1-Methyl-5-[3-(2-pyridylmethyl)thiopropyl]thio-1,2,3,4-tetrazole, brown liquid, $n_D^{29}=1.5820$ 1-Methyl-5-[3-(4-methyl-2-thiazolyl)thiopropyl]thio-1,2,3,4-tetrazole, colorless liquid, $n_D^{29}=1.5919$ 1-Methyl-5-[3-(4-pyridyl)thiopropyl]thio-1,2,3,4-tetrazole, pale yellow liquid, $n_D^{26}=1.6017$ 1-Methyl-5-[3-(2-amino-4-methyl-6-pyrimidyl)thiopropyl]thio-1,2,3,4-tetrazole, colorless powdery crystals (methanol), m.p. 119°–120° C.

1-Methyl-5-[2-(2-furylmethyl)thioethyl]thio-1,2,3,4-tetrazole, pale brown liquid, $n_D^{29}=1.5711$ 1-Methyl-5-{3-[(2-amino-4-thiazolyl)methyl]thiopropyl}thio-1,2,3,4-tetrazole, yellow prisms (methanol-water), m.p. 117°–118.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°–89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°–90.5° C.

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[3-(5-nitro-2-pyridyl)thiopropyl]thio-1,2,3,4-tetrazole, pale brown liquid, $n_D^{29}=1.6289$ 1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

1-Methyl-5-[2-methyl-3-(2-pyridyl)thiopropyl]thio-1,2,3,4-tetrazole, pale yellow liquid, $n_D^{25.5}=1.5936$ 1-Methyl-5-[4-(4-methoxyphenyl)thiobutyl]thio-1,2,3,4-tetrazole, colorless liquid, NMR (0 MHz, CDCl$_3$): δ1.50–2.20 (4H, m), 2.83 (2H, t, J=6 Hz), 3.30 (2H, t, J=6 Hz), 3.77 (3H, s), 3.87 (3H, s) 6.82 (2H, d, J=9 Hz), 7.32 (2H, d, J=9 Hz)

EXAMPLE 101

1-Methyl-5-(4-chlorobutyl)thio-1,2,3,4-tetrazole (2.00 g) and 2-mercapto-3H,4H-benzotriazepin-5-one (2.2 g) are dissolved in methanol (50 ml), and thereto is added sodium hydroxide (4.8 g), and the mixture is refluxed at 2.5 hours. After the solvent is distilled off, water is added to the residue, and the mixture is extracted with chloroform. The chloroform layer is washed with 5% aqueous sodium hydroxide and saturated aqueous sodium chloride and dried over magnesium sulfate. After chloroform is distilled off, the residue is recrystallized from methanol to give 1-methyl-5-[4-(3H,4H-1,3,4-benzotriazepin-5-on-2-yl)thiobutyl]thio-1,2,3,4-tetrazole (2.4 g) as colorless prisms, m.p. 94°–95° C.

Elemental analysis for $C_{14}H_{17}N_7OS_2$: Calcd (%): C, 46.29; H, 4.68; N, 27.00. Found (%): C, 46.14; H, 4.45; N, 26.89.

EXAMPLE 102

In the same manner as described in Example 101, the following compounds are prepared.

1-Methyl-5-(3-cyclohexylthiopropyl)thio-1,2,3,4-tetrazole, colorless liquid, $n_D^{18} = 1.5433$ 1-Methyl-5-[3-(2-pyridyl)thiopropyl]thio-1,2,3,4-tetrazole, pale yellow liquied, $n_D^{18} = 1.6022$ 1-Cyclohexyl-5-(3-ethylthiopropyl)thio-1,2,3,4-tetrazole, colorless liquid, $n_D^{14} = 1.5433$ 1-Methyl-5-[3-(1-methyl-1,2,3,4-tetrazol-5-yl)thiopropyl]thio-1,2,3,4-tetrazole, colorless prisms (recrystallized from ethanol), m.p. 141.5°–143.5° C.

1-Methyl-5-[4-(1-methyl-1,2,3,4-tetrazol-5-yl)thiobutyl]thio-1,2,3,4-tetrazole, colorless needles (recrystallized from ethanol), m.p. 122°–123° C.

1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°–128.5° C.

1-Methyl-5-[3-(1-cyclohexyl-1,2,3,4-tetrazol-5-yl)thiopropyl]thio-1,2,3,4-tetrazole, pale yellow liquid, $n_D^{18} = 1.5653$ 1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°–82° C.

1-Methyl-2-[3-(1-methylimidazol-2-yl)thiopropyl]thio-1,2,3,4-tetrazole, colorless needles (recrystallized from ether), m.p. 59.5°–60.5° C.

1-Methyl-5-(3-phenylthiopropyl)thio-1,2,3,4-tetrazole, colorless liquid, $n_D^{18} = 1.6008$ 1-Methyl-5-[2-(2-pyridyl)thioethyl]thio-1,2,3,4-tetrazole, colorless prisms, m.p. 77°–79.5° C. (ethanol)

1-Methyl-5-[4-(2-pyridyl)thiobutyl]thio-1,2,3,4-tetrazole, pale yellow prisms, m.p. 49°–51.5° C. (ethanol-water)

1-Methyl-5-[5-(2-pyridyl)thiopentyl]thio-1,2,3,4-tetrazole, colorless liquid, $n_D^{19} = 1.5853$ 1-Methyl-5-[6-(2-pyridyl)thiohexyl]thio-1,2,3,4-tetrazole, colorless prisms, m.p. 58°–60° C. (ethanol)

1-Methyl-5-[3-(3-hydroxy-2-pyridyl)thiopropyl]thio-1,2,3,4-tetrazole, pale yellow granules, m.p. 87.5°–88.5° C.

1-Methyl-5-[3-(4-methyl-2-pyrimidyl)thiopropyl]thio-1,2,3,4-tetrazole, colorless liquid, $n_D^{25.5} = 1.5853$ 1-Methyl-5-[3-(2-benzimidazolyl)thiopropyl]thio-1,2,3,4-tetrazole, colorless needles (ethanol), m.p. 137°–139° C.

1-Methyl-5-[3-(3,5-di-tert-butyl-4-hydroxyphenyl)thiopropyl]thio-1,2,3,4-tetrazole, pale yellow needles (methanol-water), m.p. 76°–77° C.

1-Methyl-5-[3-(5-amino-1,3,4-thiadiazol-2-yl)thiopropyl]thio-1,2,3,4-tetrazole, colorless prisms (ethanol), m.p. 120.5°–122° C.

1-Methyl-5-[3-(5-methyl-1,3,4-oxadiazol-2-yl)thiopropyl]thio-1,2,3,4-tetrazole, colorless liquid, $n_D^{25.5} = 1.5644$ 1-Methyl-5-[3-(β-naphthyl)thiopropyl]thio-1,2,3,4-tetrazole, colorless needles (ethanol), m.p. 56°–58° C.

1-Methyl-5-[3-(2-quinolyl)thiopropyl]thio-1,2,3,4-tetrazole, pale yellow needles (methanol), m.p. 87°–89° C.

1-Methyl-5-(4-phenylthiobutyl)thio-1,2,3,4-tetrazole, colorless prisms (ethanol) m.p. 51.5°–53° C.

1-Methyl-5-[4-(2-carboxyphenyl)thiobutyl]thio-1,2,3,4-tetrazole, pale yellow prisms (ethanol), m.p. 143.5°–144.5° C.

1-Methyl-5-[4-(2-methylphenyl)thiobutyl]thio-1,2,3,4-tetrazole, colorless liquid, $n_D^{29} = 1.5786$ 1-Methyl-5-[4-(2-aminophenyl)thiobutyl]thio-1,2,3,4-tetrazole, yellow liquid, $n_D^{29} = 1.5961$ 1-Methyl-5-[4-(4-chlorophenyl)thiobutyl]thio-1,2,3,4-tetrazole, colorless liquid, $n_D^{29} = 1.5971$ 1-Methyl-5-[3-(2-furylmethyl)thiopropyl]thio-1,2,3,4-tetrazole, brown liquid, $n_D^{26.5} = 1.5641$ 1-Methyl-5-(3-benzylthiopropyl)thio-1,2,3,4-tetrazole, colorless liquid, $n_D^{26.5} = 1.5856$ 1-Methyl-5-[3-(4-chlorobenzyl)thiopropyl]thio-1,2,3,4-tetrazole, colorless liquid, $n_D^{29} = 1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°–77° C.

1-Methyl-5-[3-(quinazolin-4-on-2-yl)thiopropyl]thio-1,2,3,4-tetrazole, colorless scales (ethanol-hexane), m.p. 132.5°–134.5° C.

1-Methyl-5-(3-ethylthiopropyl)thio-1,2,3,4-tetrazole, colorless liquid, $n_D^{29} = 1.5385$ 1-Methyl-5-(3-n-butylthiopropyl)thio-1,2,3,4-tetrazole, yellow liquid, $n_D^{29} = 1.5192$ 1-Methyl-5-(3-cyclopentylthiopropyl)thio-1,2,3,4-tetrazole, pale yellow liquid, $n_D^{29} = 1.5469$ 1-Methyl-5-[3-(2-pyridylmethyl)thiopropyl]thio-1,2,3,4-tetrazole, brown liquid, $n_D^{29} = 1.5820$ 1-Methyl-5-[3-(4-methyl-2-thiazolyl)thiopropyl]-thio-1,2,3,4-tetrazole, colorless liquid, $n_D^{29} = 1.5919$ 1-Methyl-5-[3-(4-pyridyl)thiopropyl]thio-1,2,3,4-tetrazole, pale yellow liquid, $n_D^{26} = 1.6017$ 1-Methyl-5-[3-(5-nitro-2-pyridyl)thiopropyl]thio-1,2,3,4-tetrazole, pale brown liquid, $n_D^{29} = 1.6289$ 1-Methyl-5-[3-(2-amino-4-methyl-6-pyrimidyl)thiopropyl]thio-1,2,3,4-tetrazole, colorless powdery crystals (methanol), m.p. 119°–120° C.

1-Methyl-5-[2-(2-furylmethyl)thioethyl]thio-1,2,3,4-tetrazole, pale brown liquid, $n_D^{29} = 1.5711$ 1-Methyl-5-{3-[(2-amino-4-thiazolyl)methyl]thiopropyl}thio-1,2,3,4-tetrazole, yellow prisms (methanol-water), m.p. 117°–118.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°–89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°–90.5° C.

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

1-Methyl-5-[2-methyl-3-(2-pyridyl)thiopropyl]thio-1,2,3,4-tetrazole, pale yellow liquid, $n_D^{25.5} = 1.5936$ 1-Methyl-5-[4-(4-methoxyphenyl)thiobutyl]thio-1,2,3,4-tetrazole, colorless liquid, NMR (90 MHz, CDCl$_3$): δ1.50–2.20 (4H, m), 2.83 (2H, t, J=6 Hz), 3.30 (2H, t, J=6 Hz), 3.77 (3H, s), 3.87 (3H, s), 6.82 (2H, d, J=9 Hz), 7.32 (2H, d, J=9 Hz)

EXAMPLE 103

1-Methyl-5-[(3-iodopropylthio]-1,2,3,4-tetrazole (2.8 g) and thiourea (0.8 g) are dissolved in ethanol (50 ml), and the mixture is refluxed for 2 hours. After cooling, the precipitated crystals are collected by filtration and dried, and are dissolved in ethanol (50 ml). To the mixture are added cyclopentyl bromide (1.3 g) and 10% aqueous sodium hydroxide (5 ml), and the mixture is refluxed for 3 hours. After ethanol is distilled off, water is added to the residue. The mixture is extracted with chloroform. The extract is washed with saturated aqueous sodium chloride and dried over magnesium sulfate. After chloroform is distilled off, the residue is purified by column chromatography (Wakogel C-200, eluting agent: chloroform) to give 1-methyl-5-(3-cyclopentylthiopropyl)thio-1,2,3,4-tetrazole (1.8 g), as pale yellow liquid, $n_D^{29} = 1.5469$ Elemental analysis for $C_{10}H_{18}N_4S_2$: Calcd (%): C, 46.48; H, 7.02; N, 21.68. Found (%): C, 46.43; H, 7.10; N, 21.58.

EXAMPLE 104

In the same manner as described in Example 103, the following compounds are prepared.

1-Methyl-5-(3-cyclohexylthiopropyl)thio-1,2,3,4-tetrazole, colorless liquid, $n_D^{18} = 1.5433$ 1-Methyl-5-[3-(2-pyridyl)thiopropyl]thio-1,2,3,4-tetrazole, pale yellow liquid, $n_D^{18} = 1.6022$ 1-Cyclohexyl-5-(3-ethylthiopropyl)thio-1,2,3,4-tetrazole, colorless liquid, $n_D^{14} = 1.5433$ 1-Methyl-5-[3-(1-methyl-1,2,3,4-tetrazol-5-yl)thiopropyl]thio-1,2,3,4-tetrazole, colorless prisms (recrystallized from ethanol), m.p. 141.5°–143.5° C.

1-Methyl-5-[4-(1-methyl-1,2,3,4-tetrazol-5-yl)thiobutyl]thio-1,2,3,4-tetrazole, colorless needles (recrystallized from ethanol), m.p. 122°–123° C.

1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°–128.5° C.

1-Methyl-5-[3-(1-cyclohexyl-1,2,3,4-tetrazol-5-yl)thiopropyl]thio-1,2,3,4-tetrazole, pale yellow liquid, $n_D^{18} = 1.5653$ 1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°–82° C.

1-Methyl-2-[3-(1-methylimidazol-2-yl)thiopropyl]thio-1,2,3,4-tetrazole, colorless needles (recrystallized from ether), m.p. 59.5°–60.5° C.

1-Methyl-5-(3-phenylthiopropyl)thio-1,2,3,4-tetrazole, colorless liquid, $n_D^{18} = 1.6008$

EXAMPLE 105

1-Methyl-5-[(3-iodopropyl)thio]-1,2,3,4-tetrazole (2.8 g) and N-methylthiourea (0.9 g) are dissolved in ethanol (50 ml), and the mixture is refluxed for 2 hours. After cooling, the precipitated crystals are collected by filtration and dried. The crystals are dissolved in ethanol (50 ml) and thereto are added 2-pyridylmethyl chloride (1.14 g) and 10% aqueous sodium hydroxide (10 ml), and the mixture is refluxed for 1.5 hour. After ethanol is distilled off, water is added to the residue, and the mixture is extracted with chloroform. The extract is washed with saturated aqueous sodium chloride and dried over magnesium sulfate. After chloroform is distilled off, the residue is purified by column chromatography [Wakogel C-200, eluting agent; chloroform-methanol (50:1)] to give 1-methyl-5-[3-(2-pyridylmethyl)thiopropyl]thio-1,2,3,4-tetrazole (2.7 g) as brown liquid, $n_D^{29} = 1.5820$.

Elemental analysis for $C_{11}H_{15}N_5S_2$: Calcd (%): C, 46.95; H, 5.37; N, 24.89. Found (%): C, 46.81; H, 5.41; N, 24.78.

EXAMPLE 106

In the same manner as described in Example 105, the following compounds are prepared.

1-Methyl-5-[2-(2-pyridyl)thioethyl]thio-1,2,3,4-tetrazole, colorless prisms, m.p. 77°–79.5° C. (ethanol)

1-Methyl-5-[4-(2-pyridyl)thiobutyl]thio-1,2,3,4-tetrazole, pale yellow prisms, m.p. 49°–51.5° C. (ethanol-water)

1-Methyl-5-[5-(2-pyridyl)thiopentyl]thio-1,2,3,4-tetrazole, colorless liquid, $n_D^{19} = 1.5853$ 1-Methyl-5-[6-(2-pyridyl)thiohexyl]thio-1,2,3,4-tetrazole, colorless prisms, m.p. 58°–60° C. (ethanol)

1-Methyl-5-[3-(3-hydroxy-2-pyridyl)thiopropyl]thio-1,2,3,4-tetrazole, pale yellow granules, m.p. 87.5°–88.5° C. (hexane-ethyl acetate)

1-Methyl-5-[3-(4-methyl-2-pyrimidyl)thiopropyl]thio-1,2,3,4-tetrazole, colorless liquid, $n_D^{25.5} = 1.5853$ 1-Methyl-5-[3-(2-benzimidazolyl)thiopropyl]thio-1,2,3,4-tetrazole, colorless needles (ethanol), m.p. 137°–139° C.

1-Methyl-5-[3-(3,5-di-tert-butyl-4-hydroxyphenyl)thiopropyl]thio-1,2,3,4-tetrazole, pale yellow needles (methanol-water), m.p. 76°–77° C.

1-Methyl-5-[3-(5-amino-1,3,4-thiadiazol-2-yl)thiopropyl]thio-1,2,3,4-tetrazole, colorless prisms (ethanol), m.p. 120.5°–122° C.

1-Methyl-5-[3-(5-methyl-1,3,4-oxadiazol-2-yl)thiopropyl]thio-1,2,3,4-tetrazole, colorless liquid, $n_D^{25.5} = 1.5644$ 1-Methyl-5-[3-(β-naphthyl)thiopropyl]thio-1,2,3,4-tetrazole, colorless needles (ethanol), m.p. 56°–58° C.

1-Methyl-5-[3-(2-quinolyl)thiopropyl]thio-1,2,3,4-tetrazole, pale yellow needles (methanol), m.p. 87°–89° C.

1-Methyl-5-(4-phenylthiobutyl)thio-1,2,3,4-tetrazole, colorless prisms (ethanol) m.p. 51.5°–53° C.

1-Methyl-5-[4-(2-carboxyphenyl)thiobutyl]thio-1,2,3,4-tetrazole, pale yellow prisms (ethanol), m.p. 143.5°–144.5° C.

1-Methyl-5-[4-(2-methylphenyl)thiobutyl]thio-1,2,3,4-tetrazole, colorless liquid, $n_D^{29} = 1.5786$ 1-Methyl-5-[4-(2-aminophenyl)thiobutyl]thio-1,2,3,4-tetrazole, yellow liquid, $n_D^{29} = 1.5961$ 1-Methyl-5-[4-(4-chlorophenyl)thiobutyl]thio-1,2,3,4-tetrazole, colorless liquid, $n_D^{29} = 1.5971$ 1-Methyl-5-[3-(2-furylmethyl)thiopropyl]thio-1,2,3,4-tetrazole, brown liquid, $n_D^{26.5} = 1.5641$ 1-Methyl-5-(3-benzylthiopropyl)thio-1,2,3,4-tetrazole, colorless liquid, $n_D^{26.5} = 1.5856$ 1-Methyl-5-[3-(4-chlorobenzyl)thiopropyl]thio-1,2,3,4-tetrazole, colorless liquid, $n_D^{29} = 1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°–77° C.

1-Methyl-5-[3-(quinazolin-4-on-2-yl)thiopropyl]thio-1,2,3,4-tetrazole, colorless scales (ethanol-hexane), m.p. 132.5°–134.5° C.

1-Methyl-5-[4-(3H,4H-1,3,4-benzotriazepin-5-on-2-yl)thiobutyl]thio-1,2,3,4-tetrazole, colorless prisms, m.p. 94°–95° C. (methanol)

1-Methyl-5-(3-ethylthiopropyl)thio-1,2,3,4-tetrazole, colorless liquid, $n_D^{29} = 1.5385$ 1-Methyl-5-(3-n-butylthiopropyl)thio-1,2,3,4-tetrazole, yellow liquid, $n_D^{29} = 1.5192$ 1-Methyl-5-[3-(4-methyl-2-thiazolyl)thiopropyl]thio-1,2,3,4-tetrazole, colorless liquid, $n_D^{29} = 1.5919$ 1-Methyl-5-[3-(4-pyridyl)thiopropyl]thio-1,2,3,4-tetrazole, pale yellow liquid, $n_D^{26} = 1.6017$ 1-Methyl-5-[3-(5-nitro-2-pyridyl)thiopropyl]thio-1,2,3,4-tetrazole, pale brown liquid, $n_D^{29} = 1.6289$ 1-Methyl-5-[3-(2-amino-4-methyl-6-pyrimidyl)thiopropyl]thio-1,2,3,4-tetrazole, colorless powdery crystals (methanol), m.p. 119°–120° C.

1-Methyl-5-[2-(2-furylmethyl)thioethyl]thio-1,2,3,4-tetrazole, pale brown liquid, $n_D^{29} = 1.5711$ 1-Methyl-5-{3-[(2-amino-4-thiazolyl)methyl]thiopropyl}thio-1,2,3,4-tetrazole, yellow prisms (methanol-water), m.p. 117°–118.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°–89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°–90.5° C.

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

1-Methyl-5-[2-methyl-3-(2-pyridyl)thiopropyl]thio-1,2,3,4-tetrazole, pale yellow liquid, $n_D^{25.5} = 1.5936$ 1-Methyl-5-[4-(4-methoxyphenyl)thiobutyl]thio-1,2,3,4-tetrazole, colorless liquid, NMR (90 MHz, CDCl₃): δ1.50–2.20 (4H, m), 2.83 (2H, t, J=6 Hz), 3.30 (2H, t, J=6 Hz), 3.77 (3H, s), 3.87 (3H, s), 6.82 (2H, d, J=9 Hz), 7.32 (2H, d, J=9 Hz)

EXAMPLE 107

2-Amino-4-methyl-6-chloropyrimidine (1.43 g) and thiourea (0.8 g) are dissolved in ethanol (50 ml), and the mixture is refluxed for 2 hours. After cooling, the precipitated crystals are collected by filtration and dried. The crystals are dissolved in ethanol (50 ml) and thereto are added 1-methyl-5-[(3-chloropropyl)thio]1,2,3,4-tetrazole (1.73 g) and 10% aqueous sodium hydroxide (5 ml), and the mixture is refluxed for 4 hours. After ethanol is distilled off, water is added to the residue, and the mixture is extracted with chloroform. The extract is washed with saturated aqueous sodium chloride and dried over magnesium sulfate. After chloroform is distilled off, the residue is purified by column chromatography [Wakogel C-200, eluting agent; chloroform-methanol (50:1)], followed by recrystallizing from methanol to give 1-methyl-5-[3-(2-amino-4-methyl-6-pyrimidyl)thiopropyl]thio-1,2,3,4-tetrazole (0.7 g), as colorless powdery crystals, m.p. 119°–120° C.

Elemental analysis for $C_{10}H_{15}N_7S_2$: Calcd (%): C, 40.40; H, 5.05; N, 32.99. Found (%): C, 40.28; H, 4.87; N, 33.10.

EXAMPLE 108

In the same manner as described in Example 107, the following compounds are prepared.

1-Methyl-5-[2-(2-pyridyl)thioethyl]thio-1,2,3,4-tetrazole, colorless prisms, m.p. 77°–79.5° C. (ethanol)

1-Methyl-5-[4-(2-pyridyl)thiobutyl]thio-1,2,3,4-tetrazole, pale yellow prisms, m.p. 49°–51.5° C. (ethanol-water)

1-Methyl-5-[5-(2-pyridyl)thiopentyl]thio-1,2,3,4-tetrazole, colorless liquid, $n_D^{19} = 1.5853$ 1-Methyl-5-[6-(2-pyridyl)thiohexyl]thio-1,2,3,4-tetrazole, colorless prisms, m.p. 58°–60° C. (ethanol)

1-Methyl-5-[3-(4-methyl-2-pyrimidyl)thiopropyl]thio-1,2,3,4-tetrazole, colorless liquid, $n_D^{25.5} = 1.5853$ 1-Methyl-5-[3-(2-benzimidazolyl)thiopropyl]thio-1,2,3,4-tetrazole, colorless needles (ethanol), m.p. 137°–139° C.

1-Methyl-5-[3-(3.5-di-tert-butyl-4-hydroxyphenyl)thiopropyl]thio-1,2,3,4-tetrazole, pale yellow needles (methanol-water), m.p. 76°–77° C.

1-Methyl-5-[3-(5-amino-1,3,4-thiadiazol-2-yl)thiopropyl]thio-1,2,3,4-tetrazole, colorless prisms (ethanol), m.p. 120.5°–122° C.

1-Methyl-5-[3-(5-methyl-1,3,4-oxadiazol-2-yl)thiopropyl]thio-1,2,3,4-tetrazole, colorless liquid, $n_D^{25.5} = 1.5644$ 1-Methyl-5-[3-(β-naphthyl)thiopropyl]thio-1,2,3,4-tetrazole, colorless needles (ethanol), m.p. 56°–58° C.

1-Methyl-5-[3-(2-quinolyl)thiopropyl]thio-1,2,3,4-tetrazole, pale yellow needles (methanol), m.p. 87°–89° C.

1-Methyl-5-(4-phenylthiobutyl)thio-1,2,3,4-tetrazole, colorless prisms (ethanol) m.p. 51.5°–53° C.

1-Methyl-5-[4-(2-carboxyphenyl)thiobutyl]thio-1,2,3,4-tetrazole, pale yellow prisms (ethanol), m.p. 143.5°–144.5° C.

1-Methyl-5-[4-(2-methylphenyl)thiobutyl]thio-1,2,3,4-tetrazole, colorless liquid, $n_D^{29} = 1.5786$ 1-Methyl-5-[4-(2-aminophenyl)thiobutyl]thio-1,2,3,4-tetrazole, yellow liquid, $n_D^{29} = 1.5961$ 1-Methyl-5-[4-(4-chlorophenyl)thiobutyl]thio-1,2,3,4-tetrazole, colorless liquid, $n_D^{29} = 1.5971$ 1-Methyl-5-[3-(2-furylmethyl)thiopropyl]thio-1,2,3,4-tetrazole, brown liquid, $n_D^{26.5} = 1.5641$ 1-Methyl-5-(3-benzylthiopropyl)thio-1,2,3,4-tetrazole, colorless liquid, $n_D^{26.5} = 1.5856$ 1-Methyl-5-[3-(4-chlorobenzyl)thiopropyl]thio-1,2,3,4-tetrazole, colorless liquid, $n_D^{29} = 1.5858$ 1-Methyl-5-[3-(4,5-dimethyl-1,2,4-triazol-3-yl)thiopropyl]thio-1,2,3,4-tetrazole, colorless prisms (ethanol-hexane), m.p. 74°–77° C.

1-Methyl-5-[3-(quinazolin-4-on-2-yl)thiopropyl]thio-1,2,3,4-tetrazole, colorless scales (ethanol-hexane), m.p. 132.5°–134.5° C.

1-Methyl-5-[4-(3H,4H-1,3,4-benzotriazepin-5-on-2-yl)thiobutyl]thio-1,2,3,4-tetrazole, colorless prisms, m.p. 94°–95° C. (methanol)

1-Methyl-5-(3-ethylthiopropyl)thio-1,2,3,4-tetrazole, colorless liquid, $n_D^{29} = 1.5385$ 1-Methyl-5-(3-n-butylthiopropyl)thio-1,2,3,4-tetrazole, yellow liquid, $n_D^{29} = 1.5192$ 1-Methyl-5-(3-cyclopentylthiopropyl)thio-1,2,3,4-tetrazole, pale yellow liquid, $n_D^{29} = 1.5469$ 1-Methyl-5-[3-(2-pyridylmethyl)thiopropyl]thio-1,2,3,4-tetrazole, brown liquid, $n_D^{29} = 1.5820$ 1-Methyl-5-[3-(4-methyl-2-thiazolyl)thiopropyl]thio-1,2,3,4-tetrazole, colorless liquid, $n_D^{29} = 1.5919$ 1-Methyl-5-[3-(4-pyridyl)thiopropyl]thio-1,2,3,4-tetrazole, pale yellow liquid, $n_D^{26} = 1.6017$ 1-Methyl-5-[3-(5-nitro-2-pyridyl)thiopropyl]thio-1,2,3,4-tetrazole, pale brown liquid, $n_D^{29} = 1.6289$ 1-Methyl-5-[2-(2-furylmethyl)thioethyl]thio-1,2,3,4-tetrazole, pale brown liquid, $n_D^{29} = 1.5711$ 1-Methyl-5-{3-[(2-amino-4-thiazolyl)methyl]thiopropyl}thio-1,2,3,4-tetrazole, yellow prisms (methanol-water), m.p. 117°–118.5° C.

1-Cyclohexyl-5-[3-(1-cyclohexyl-1,2,3,4-tetrazol-5-yl)thiopropyl]thio-1,2,3,4-tetrazole, pale yellow granules (ether-ethanol), m.p. 88.5°–89.5° C.

1-Methyl-5-[3-(1-phenyl-1,2,3,4-tetrazol-5-yl)thiopropyl]thio-1,2,3,4-tetrazole, colorless prisms (ethanol-ligroin), m.p. 89°–90.5° C.

1-Methyl-5-[5-(1-methyl-1,2,3,4-tetrazol-5-yl)thiopentyl]thio-1,2,3,4-tetrazole, colorless prisms (ethanol), m.p. 64°–65° C.

1-Methyl-5-[6-(1-methyl-1,2,3,4-tetrazol-5-yl)thiohexyl]thio-1,2,3,4-tetrazole, colorless prisms (acetone), m.p. 91°–93.5° C.

1-Methyl-5-[2-methyl-3-(1-methyl-1,2,3,4-tetrazol-5-yl)thiopropyl]thio-1,2,3,4-tetrazole, colorless prisms (ethanol), m.p. 87°–89.5° C.

1-Methyl-5-[3-methyl-3-(1-methyl-1,2,3,4-tetrazol-5-yl)thiopropyl]thio-1,2,3,4-tetrazole, colorless needles (ethanol), m.p. 68.5°–70.5° C.

1-Methyl-5-[2-methyl-3-(2-pyridyl)thiopropyl]thio-1,2,3,4-tetrazole, pale yellow liquid, $n_D^{25.5} = 1.5936$ 1-Methyl-5-[4-(4-methoxyphenyl)thiobutyl]thio-1,2,3,4-tetrazole, colorless liquid, NMR (90 MHz, CDCl₃): δ1.50–2.20 (4H, m), 2.83 (2H, t, J=6 Hz), 3.30 (2H, t, J=6 Hz), 3.77 (3H, s), 3.87 (3H, s) 6.82 (2H, d, J=9 Hz), 7.32 (2H, d, J=9 Hz)

1-Methyl-5-(3-cyclohexylthiopropyl)thio-1,2,3,4-tetrazole, colorless liquid, $n_D^{18} = 1.5433$ 1-Methyl-5-[3-(2-pyridyl)thiopropyl]thio-1,2,3,4-tetrazole, pale yellow liquid, $n_D^{18} = 1.6022$ 1-Cyclohexyl-5-(3-ethylthiopropyl)thio-1,2,3,4-tetrazole, colorless liquid, $n_D^{14} = 1.5433$ 1-Methyl-5-[3-(1-methyl-1,2,3,4-tetrazol-5-yl)thiopropyl]thio-1,2,3,4-tetrazole, colorless prisms (recrystallized from ethanol), m.p. 141.5°–143.5° C.

1-Methyl-5-[4-(1-methyl-1,2,3,4-tetrazol-5-yl)thiobutyl]thio-1,2,3,4-tetrazole, colorless needles (recrystallized from ethanol), m.p. 122°–123° C.

1-Phenyl-5-[4-(1-phenyl-1,2,3,4-tetrazol-5-yl)thiobutyl]thio-1,2,3,4-tetrazole, colorless needles (recrystallized from ethanol-chloroform), m.p. 127°–128.5° C.

1-Methyl-5-[3-(1-cyclohexyl-1,2,3,4-tetrazol-5-yl)thiopropyl]thio-1,2,3,4-tetrazole, pale yellow liquid, $n_D^{18} = 1.5653$ 1-Phenyl-5-[3-(1-phenyl-1,2,3,4-tetrazol-5-yl)thiopropyl]thio-1,2,3,4-tetrazole, colorless needles (recrystallized from methanol-chloroform), m.p. 81°–82° C.

1-Methyl-2-[3-(1-methylimidazol-2-yl)thiopropyl]thio-1,2,3,4-tetrazole, colorless needles (recrystallized from ether), m.p. 59.5°–60.5° C.

EXAMPLE 109

1-Methyl-1,2,3,4-tetrazol-5-yl 4-bromobutyl sulfoxide (2.7 g) and 1-methyl-5-mercapto-1,2,3,4-tetrazole (1.4 g) are dissolved in acetone (50 ml), and thereto is added potassium carbonate (1.4 g), and the mixture is refluxed for 2 hours. After acetone is distilled off, water is added to the residue, and the mixture is extracted with chloroform. The chloroform solution is washed with saturated aqueous sodium chloride and dried over magnesium sulfate. After chloroform is distilled off, the residue is purified by column chromatography (Kieselgel 60), eluting with chloroform-methanol (100:1) to give 1-methyl-1,2,3,4-tetrazol-5-yl 4-(1-methyl-1,2,3,4-tetrazol-5-yl)thiobutyl sulfoxide (1.5 g), as colorless liquid, $n_D^{19} = 1.5660$.

Elemental analysis for $C_8H_{14}N_8S_2O$: Calcd (%): C, 31.78; H, 4.67; N, 37.06. Found (%): C, 31.65; H, 4.72; N, 37.12.

EXAMPLE 110

In the same manner as described in Example 109, the following compounds are prepared.

1-Methyl-1,2,3,4-tetrazol-5-yl 4-(1-methyl-1,2,3,4-tetrazol-5-yl)thiobutyl sulfone, colorless needles (ethanol-chloroform), m.p. 70°–72° C.

4-(2-Pyridyl)thiobutyl 1-methyl-1,2,3,4-tetrazol-5-yl sulfoxide, pale yellow liquid, $n_D^{25.5} = 1.5893$ 1-Methyl-1,2,3,4-tetrazol-5-yl 3-(5-methyl-1,3,4-oxadiazol-2-yl)thiopropyl sulfoxide, pale yellow liquid, $n_D^{24.5} = 1.5620$ 1-Methyl-1,2,3,4-tetrazol-5-yl 3-(2-pyridyl)thiopropyl sulfoxide, pale yellow liquid, $n_D^{23.5} = 1.5997$ 1-Methyl-1,2,3,4-tetrazol-5-yl 3-methyl-3-(1-methyl-1,2,3,4-tetrazol-5-yl)thiopropyl sulfoxide, colorless liquid, $n_D^{21.5} = 1.5680$ 1-Methyl-1,2,3,4-tetrazol-5-yl 3-methyl-3-(5-methyl-1,3,4-oxadiazol-5-yl)thiopropyl sulfoxide, pale yellow liquid, $n_D^{20} = 1.5580$ 1-Methyl-1,2,3,4-tetrazol-5-yl 4-(2-pyridyl)thiobutyl sulfone, colorless liquid, $n_D^{27.5} = 1.5743$

EXAMPLE 111

2-Chloropyridine (1.13 g) and thiourea (0.8 g) are dissolved in ethanol (50 ml), and the mixture is refluxed for 1 hour. After cooling, the precipitated crystals are collected by filtration and dried. The crystals are dissolved in ethanol (50 ml) and thereto are added 1-methyl-1,2,3,4-tetrazol-5-yl 4-bromobutyl sulfoxide (2.4 g) and 10% aqueous sodium hydroxide (10 ml), and the mixture is refluxed for 4 hours. After ethanol is distilled off, water is added to the residue, and the mixture is extracted with chloroform. The extract is washed with saturated aqueous sodium chloride and dried over magnesium sulfate. After chloroform is distilled off, the residue is purified by column chromatography (Kieselgel 60, eluting agent, chloroform) to give 4-(2-pyridyl)- thiobutyl 1-methyl-1,2,3,4-tetrazol-5-yl sulfoxide, as pale yellow liquid, $n_D^{25.5}=1.5893$.

Elemental analysis for $C_{11}H_{15}N_5S_2O$: Calcd (%): C, 44.42; H, 5.08; N, 23.55. Found (%): C, 44.32; H, 5.12; N, 23.39.

EXAMPLE 112

In the same manner as described in Example 111, the following compounds are prepared.

1-Methyl-1,2,3,4-tetrazol-5-yl 4-(1-methyl-1,2,3,4-tetrazol-5-yl)thiobutyl sulfoxide, colorless liquid, $n_D^{19}=1.5660$ 1-Methyl-1,2,3,4-tetrazol-5-yl 4-(1-methyl-1,2,3,4-tetrazol-5-yl)thiobutyl sulfone, colorless needles (ethanol), m.p. 70°–72° C.

3-(1-Methyl-1,2,3,4-tetrazol-5-yl)thiopropyl 2-pyridyl sulfoxide, colorless prisms (ethanol), m.p. 88.5°–90.5° C.

3-(1-Methyl-1,2,3,4-tetrazol-5-yl)thiopropyl 2-pyridyl sulfone, colorless prisms (ethanol), m.p. 98.5°–101° C.

EXAMPLE 113

1-Methyl-5-[3-(2-pyridyl)thiopropyl]thio-1,2,3,4-tetrazole (2.2 g) is dissolved in formic acid (20 ml), and thereto is added with stirring 30% hydrogen peroxide (2.2 g) at room temperature. The mixture is stirred at room temperature for 5 hours, and thereto is added sodium hydrogensulfite under ice-cooling in order to decompose excess amount of performic acid. Water is added to the mixture and the mixture is extracted with chloroform. The chloroform solution is washed with water and saturated aqueous sodium bicarbonate and dried over magnesium sulfate. After chloroform is distilled off, the residue is purified by column chromatography [Kieselgel 60, eluting agent, chloroform-methanol (50:1)] to give 3-(1-methyl-1,2,3,4-tetrazol-5-yl)sulfinylpropyl 2-pyridyl sulfoxide (0.5 g) as colorless liquid, $n_D^{28.5}=1.5795$ Elemental analysis for $C_{10}H_{13}N_5S_2O_2$: Calcd (%): C, 40.12; H, 4.38; N, 23.39. Found (%): C, 40.01; H, 4.48; N, 23.28.

EXAMPLE 114

In the same manner as described in Example 113, except that the starting materials are the compounds of the formula (1) wherein the sum of l and m is 0, and the 30% hydrogen peroxide is used in an amount of equimole (in case of introducing one oxygen), 2 moles (in case of introducing two oxygen), 3 moles (in case of introducing three oxygen) or 4 moles (in case of introducing four oxygen), the following compounds are prepared.

4-(1-Methyl-1,2,3,4-tetrazol-5-yl)sulfonylbutyl 1-methyl-1,2,3,4-tetrazol-5-yl sulfone, colorless prisms (dimethylformamide), m.p. 192°–194° C.

1-Methyl-1,2,3,4-tetrazol-5-yl 4-(1-methyl-1,2,3,4-tetrazol-5-yl)thiobutyl sulfoxide, colorless liquid, $n_D^{19}=1.5660$ 1-Methyl-1,2,3,4-tetrazol-5-yl 4-(1-methyl-1,2,3,4-tetrazol-5-yl)thiobutyl sulfone, colorless needles (ethanol-chloroform), m.p. 70°–72° C.

3-(1-Methyl-1,2,3,4-tetrazol-5-yl)thiopropyl 2-pyridyl sulfoxide, colorless prisms (ethanol), m.p. 88.5°–90.5° C.

3-(1-Methyl-1,2,3,4-tetrazol-5-yl)thiopropyl 2-pyridyl sulfone, colorless prisms (ethanol), m.p. 98.5°–101° C.

4-(1-Methyl-1,2,3,4-tetrazol-5-yl)sulfinylbutyl 1-methyl-1,2,3,4-tetrazol-5-yl sulfone, colorless scales (ethanol-chloroform), m.p. 147°–149° C.

4-(2-Pyridyl)thiobutyl 1-methyl-1,2,3,4-tetrazol-5-yl sulfoxide, pale yellow liquid, $n_D^{25.5}=1.5893$

EXAMPLE 115

3-(1-Methyl-1,2,3,4-tetrazol-5-yl)thiopropyl 2-pyridyl sulfoxide (2.8 g) is dissolved in formic acid (20 ml) and thereto is added with stirring 30% hydrogen peroxide (1.3 g) at room temperature, and the mixture is stirred for 5 hours. To the mixture is added sodium hydrogen sulfite under ice-cooling in order to decompose excess performic acid. Water is added to the resulting mixture and it is extracted with chloroform. The chloroform solution is washed with water and saturated aqueous sodium bicarbonate and dried over magnesium sulfate. After chloroform is distilled off, the residue is purified by column chromatography [Wakogel C-200, eluting agent, chloroform-methanol (50:1)] to give 3-(1-methyl-1,2,3,4-tetrazol-5-yl)sulfinylpropyl 2-pyridyl sulfoxide (0.8 g) as colorless liquid, $n_D^{28.5}=1.5795$.

Elemental analysis for $C_{10}H_{13}N_5S_2O_2$: Calcd (%): C, 40.12; H, 4.38; N, 23.39. Found (%): C, 40.31; H, 4.24; N, 23.26.

EXAMPLE 116

In the same manner as described in Example 115, except that the starting materials are the compounds of the formula (1) wherein the sum of l and m is 1, and the 30% hydrogen peroxide is used in an amount of equimole (in case of introducing one oxygen), 2 moles (in case of introducing two oxygen), or 3 moles (in case of introducing three oxygen), the following compounds are prepared.

4-(1-Methyl-1,2,3,4-tetrazol-5-yl)sulfonylbutyl 1-methyl-1,2,3,4-tetrazol-5-yl sulfone, colorless prisms (dimethylformamide), m.p. 192°–194° C.

1-Methyl-1,2,3,4-tetrazol-5-yl 4-(1-methyl-1,2,3,4-tetrazol-5-yl)thiobutyl sulfone, colorless needles (ethanol-chloroform), m.p. 70°–72° C.

3-(1-Methyl-1,2,3,4-tetrazol-5-yl)thiopropyl 2-pyridyl sulfone, colorless prisms (ethanol), m.p. 98.5°–101° C.

4-(1-Methyl-1,2,3,4-tetrazol-5-yl)sulfinylbutyl 1-methyl-1,2,3,4-tetrazol-5-yl sulfone, colorless scales (ethanol-chloroform), m.p. 147°–149° C.

EXAMPLE 117

4-(1-Methyl-1,2,3,4-tetrazol-5-yl)thiobutyl 1-methyl-1,2,3,4-tetrazol-5-yl sulfone (1 g) is dissolved in formic acid (10 ml), and thereto is added with stirring 30% hydrogen peroxide (0.4 g) at room temperature, and the mixture is stirred for 3 hours. Water is added to the mixture and the precipitated crystals are collected by filtration and recrystallized from ethanol-chloroform to give 4-(1-methyl-1,2,3,4-tetrazol-5-yl)sulfinylbutyl 1-methyl-1,2,3,4-tetrazol-5-yl sulfone (0.4 g) as colorless scales, m.p. 147°–149° C.

Elemental analysis for $C_8H_{14}N_8S_2O_3$: Calcd (%): C, 28.74; H, 4.22; N, 33.51. Found (%): C, 28.62; H, 4.31; N, 33.41.

EXAMPLE 118

In the same manner as described in Example 117, except that the starting materials are the compounds of the formula (1) wherein the sum of l and m is 2 and either one of them is 0, and the 30% hydrogen peroxide is used in an amount of equimole (in case of introducing one oxygen), 2 moles (in case of introducing two oxygen), the following compounds are prepared.

4-(1-Methyl-1,2,3,4-tetrazol-5-yl)sulfonylbutyl 1-methyl-1,2,3,4-tetrazol-5-yl sulfone, colorless prisms (dimethylformamide), m.p. 192°-194° C.

EXAMPLE 119

3-(1-Methyl-1,2,3,4-tetrazol-5-yl)sulfinylpropyl 1-methyl-1,2,3,4-tetrazol-5-yl sulfoxide (3.0 g) is dissolved in formic acid (30 ml), and thereto is added with stirring 30% hydrogen peroxide (3.4 g) at room temperature, and the mixture is stirred for 4 hours. Sodium hydrogensulfite is added to the mixture under ice-cooling in order to decompose excess performic acid. Water is added to the mixture and the precipitated crystals are collected by filtration and recrystallized from dimethylformamide to give 4-(1-methyl-1,2,3,4-tetrazol-5-yl)sulfonylbutyl 1-methyl-1,2,3,4-tetrazol-5-yl sulfone (1.8 g), as colorless prisms, m.p. 192°-194° C.

Elemental analysis for $C_8H_{14}N_8S_2O_4$: Calcd (%): C, 27.42; H, 4.03; N, 31.98. Found (%): C, 27.22; H, 4.12; N, 32.12.

EXAMPLE 120

In the same manner as described in Example 119, except that the starting materials are the compounds of the formula (1) wherein the sum of l and m is 1, and the 30% hydrogen peroxide is used in an amount of equimole (in case of introducing one oxygen), 2 moles (in case of introducing two oxygen), the following compounds are prepared.

4-(1-Methyl-1,2,3,4-tetrazol-5-yl)sulfinylbutyl 1-methyl-1,2,3,4-tetrazol-5-yl sulfone, colorless scales (ethanol-chloroform), m.p. 147°-149° C.

EXAMPLE 121

4-(1-Methyl-1,2,3,4-tetrazol-5-yl)sulfinylbutyl 1-methyl-1,2,3,4-tetrazol-5-yl sulfone (3.2 g) is dissolved in formic acid (30 ml), and thereto is added with stirring 30% hydrogen peroxide (2.3 g) at room temperature, and the mixture is stirred for 5 hours. Sodium hydrogensulfite is added to the mixture under ice-cooling in order to decompose excess performic acid. Water is added to the mixture and the precipitated crystals are collected by filtration and recrystallized from N,N-dimethylformamide to give 4-(1-methyl-1,2,3,4-tetrazol-5-yl)sulfonylbutyl 1-methyl-1,2,3,4-tetrazol-5-yl sulfone (2.1 g) as colorless prisms, m.p. 192°-194° C.

Elemental analysis for $C_8H_{14}N_8S_2O_4$: Calcd (%): C, 27.42; H, 4.03; N, 31.98. Found (%): C, 27.50; H, 3.78; N, 31.95.

EXAMPLE 122

1-Methyl-5-(2-pyridyl)methylthio-1,2,3,4-tetrazole (2.0 g) is dissolved in formic acid (20 ml), and thereto is added with stirring 30% hydrogen peroxide (1.3 g) at room temperature, and the mixture is stirred for 5 hours. Sodium hydrogensulfite is added to the mixture under ice-cooling in order to decompose excess performic acid. Water is added to the mixture and it is extracted with chloroform. Chloroform solution is washed with water and saturated aqueous sodium bicarbonate and dried over magnesium sulfate. After chloroform is distilled off, the residue is purified by column chromatography [Wakogel C-200, eluting agent, chloroform-methanol (50:1)] to give 1-methyl-1,2,3,4-tetrazol-5-yl 2-pyridylmethyl sulfoxide as brown liquid, $n_D^{26.5}=1.5810$.

EXAMPLE 123

1-Phenyl-5-[3-(N-benzoylamino)propylthio]-1,2,3,4-tetrazole (1.7 g) is dissolved in dimethylformamide (30 ml). To the mixture is added with stirring 50% oily sodium hydride (0.3 g) at room temperature. After foaming is finished, the mixture is stirred at 60°-70° C. for one hour. After cooling until room temperature, ethyl bromide (0.8 g) is added dropwise to the resulting mixture, and thereafter, the mixture is stirred at 60°-70° C. for 8 hours. After dimethylformamide is distilled off, the residue is purified by column chromatography (Wakogel C-200), followed by eluting with chloroform to give 1-phenyl-5[3-(N-ethyl-N-benzoylamino)propylthio]-1,2,3,4-tetrazole (1.2 g), as a colorless liquid, $n_D^{24}=1.5898$.

EXAMPLE 124

In the same manner as described in Example 123, the following compounds are prepared.

1-Methyl-5-[3-(N-ethyl-N-cyclohexylcarbonylamino)propylthio]-1,2,3,4-tetrazole, colorless liquid, $n_D^{23.5}=1.5267$ 1-Methyl-5-[3-(N-ethyl-N-propionylamino)propylthio]-1,2,3,4-tetrazole, pale yellow liquid, $n_D^{21.5}=1.5220$ 1-Methyl-5-[3-(N-methyl-N-acetylamino)propylthio]-1,2,3,4--tetrazole, pale yellow prisms (hexane-ethyl acetate), m.p. 80°-81° C.

1-Methyl-5-[3-(N-methyl-N-cyclohexylcarbonylamino)propylthio]-1,2,3,4-tetrazole, colorless liquid, $n_D^{19}=1.5268$ 1-Methyl-5-[3-(N-ethyl-N-cyclopentylcarbonylamino)propylthio]-1,2,3,4-tetrazole, colorless liquid, $n_D^{28.5}=1.5240$ 1-Methyl-5-[3-(N-ethyl-N-benzoylamino)propylthio]-1,2,3,4-tetrazole, colorless liquid, $n_D^{26.5}=1.5454$ 1-Methyl-5-{3-[N-ethyl-N-(2-furylcarbonyl)amino]-propylthio}-1,2,3,4-tetrazole, colorless liquid, $n_D^{28.5}=1.5495$ 1-Methyl-5-{3-[N-benzyl-N-propionylamino]propylthio}-1,2,3,4-tetrazole, colorless liquid, $n_D^{26}=1.5538$

EXAMPLE 125

1-Methyl-5-[3-(N-ethylamino)propylthio]-1,2,3,4-tetrazole (1 g) is dissolved in a mixture of acetone (50 ml) and water (10 ml). To the mixture is added potassium carbonate (0.7 g) and thereto is added dropwise with stirring cyclohexanecarboxylic acid chloride (0.9 g) under ice-cooling. Stirring is continued for 2 hours under ice-cooling. After acetone is distilled off, water is added to the resulting residue and the mixture is extracted with chloroform. The chloroform solution is washed with saturated aqueous sodium bicarbonate and saturated aqueous sodium chloride and dried over sodium sulfate. Chloroform is distilled off and then the residue is purified by column chromatography (Wakogel C-200), followed by eluting with chloroform to give 1-methyl-5-[3-(N-ethyl-N-cyclohexylcarbonylamino)propylthio]-1,2,3,4-tetrazole (0.9 g), colorless liquid, $n_D^{23.5}=1.5267$.

Elemental analysis for $C_{14}H_{25}N_5OS$: Calcd (%): C, 53.99; H, 8.09; N, 22.49. Found (%): C, 54.20; H, 7.78; N, 22.56.

EXAMPLE 126

In the same manner as described in Example 125, the following compounds are prepared:

1-Phenyl-5-[3-(N-ethyl-N-benzoylamino)propylthio]-1,2,3,4-tetrazole, colorless liquid, $n_D^{24}=1.5898$ 1-Methyl-5-[3-(N-propionylamino)propylthio]-1,2,3,4-tetrazole, pale yellow liquid, $n_D^{8.5}=1.5311$ 1-Methyl-5-[3-(N-cyclohexylcarbonylamino)propylthio]-1,2,3,4-tetrazole, colorless flakes (hexane-ethyl acetate), m.p. 86.5°–88° C.

1-Methyl-5-[3-(N-ethyl-N-propionylamino)propylthio]-1,2,3,4-tetrazole, pale yellow liquid, $n_D^{21.5}=1.5220$ 1-Phenyl-5-[3-(N-benzoylamino)propylthio]-1,2,3,4-tetrazole, colorless needles (hexane-ethyl acetate), m.p. 105°–107° C.

1-Methyl-5-[3-(N-methyl-N-acetylamino)propylthio]-1,2,3,4-tetrazole, pale yellow prisms (hexane-ethyl acetate), m.p. 80°–81° C.

1-Methyl-5-[3-(N-acetylamino)propylthio]-1,2,3,4-tetrazole, colorless liquid, $n_D^{26.5}=1.5280$ 1-Methyl-5-[3-(N-methyl-N-cyclohexylcarbonylamino)propylthio]-1,2,3,4-tetrazole, colorless liquid, $n_D^{19}=1.5268$ 1-Methyl-5-[3-N-ethyl-N-cyclopentylcarbonylamino)propylthio]-1,2,3,4-tetrazole, colorless liquid, $n_D^{28.5}=1.5240$ 1-Methyl-5-[3-(N-cyclopentylcarbonylamino)propylthio]-1,2,3,4-tetrazole, colorless prisms (ether), m.p. 70°–72° C.

1-Methyl-5-[2-(N-cyclohexylcarbonylamino)ethylthio]-1,2,3,4-tetrazole, colorless needles (ethanol-ligroin), m.p. 115.5°–116.5° C.

1-Methyl-5-[3-(N-ethyl-N-benzoylamino)propylthio]-1,2,3,4-tetrazole, colorless liquid, $n_D^{26.5}=1.5454$ 1-Methyl-5-{3-[N-(2-pyridylcarbonyl)amino]propylthio}-1,2,3,4-tetrazole, brown liquid, $n_D^{26.5}=1.5782$ 1-Methyl-5-{3-[N-ethyl-N-(2-furylcarbonyl)amino]propylthio}-1,2,3,4-tetrazole, colorless liquid, $n_D^{28.5}=1.5495$ 1-Methyl-5-{3-[N-(2-furylcarbonyl)amino]propylthio}-1,2,3,4-tetrazole, colorless prisms (ethanol-hexane), m.p. 80.5°–83° C.

EXAMPLE 127

1-Methyl-5-(3-aminopropylthio)-1,2,3,4-tetrazole (0.9 g) is dissolved in a mixture of acetone (50 ml) and water (10 ml). To the mixture is added potassium carbonate (0.7 g) and thereto is added dropwise with stirring 4-methoxybenzoylchloride (1.1 g) under ice-cooling. Stirring is continued for 2 hours under ice-cooling. After acetone is distilled off, water is added to the resulting residue and the mixture is extracted with chloroform. The chloroform solution is washed with saturated aqueous sodium bicarbonate and saturated aqueous sodium chloride and dried over sodium sulfate. Chloroform is distilled off and then the residue is purified by column chloratography (Wakogel C-200), followed by eluting with chloroform to give 1-methyl-5-{3-[N-(4-methoxybenzoyl)amino]propylthio}-1,2,3,4-tetrazole (0.7 g), colorless needles (ethyl acetate-ethanol), m.p. 118°–122° C.

EXAMPLE 128

In the same manner as described in Example 127, the following compound is prepared:

1-Methyl-5-{3-[N-(3,4,5-trimethoxybenzoyl)amino]propylthio}-1,2,3,4-tetrazole, colorless prisms (ethyl acetate-hexane), m.p. 70.5°–73° C.

EXAMPLE 129

1-Methyl-5-(3-chloropropylthio)-1,2,3,4-tetrazole (3.8 g) is dissolved in dimethylformamide (50 ml). To the mixture are added sodium iodide (3 g) and diethylamine (4.4 g) and the mixture is stirred at 60°–70° C. for 3 hours. Dimethylformamide is distilled off under reduced pressure, and the residue is purified by alumina column chromatography (basic alumina, made by Merk & Co.), followed by eluting with n-hexane to give 1-methyl-5-[3-(N,N-diethylamino)propylthio]-1,2,3,4-tetrazole (1.1 g), colorless liquid, $n_D^{25}=1.5040$.

Elemental analysis for $C_9H_{19}N_5S$: Calcd (%): C, 47.13; H, 8.35; N, 30.54. Found (%): C, 47.27; H, 8.39; N, 30.57.

EXAMPLE 130

In the same manner as described in Example 129, the following compounds are prepared:

1-Methyl-5-[3-(phthalimido)propylthio]-1,2,3,4-tetrazole, colorless prisms (recrystallized from ethanol), m.p. 134°–135.5° C.

1-Methyl-5-(3-aminopropylthio)-1,2,3,4-tetrazole, colorless liquid, $n_D^{21.5}=1.5384$ 1-Methyl-5-{3-[N-(1-methyl-1,2,3,4-tetrazol-5-yl)amino]propylthio}-1,2,3,4-tetrazole, colorless prisms (ethanol), m.p. 146°–148° C.

EXAMPLE 131

1-Methyl-5-[3-(phthalimido)propylthio]-1,2,3,4-tetrazole (3.5 g) is dissolved in ethanol (50 ml). To the mixture is added hydrazine hydrate (85%, 2 g) and the mixture is refluxed for 1 hour. After cooling, the precipitate is filtered off and ethanol is distilled off. The residue is dissolved in ethyl acetate and dried over magnesium sulfate. Ethyl acetate is distilled off, and then the residue is purified by column chromatography (Alminium oxide 60, made by Merk & Co.), followed by eluting with chloroform to give 1-Methyl-5-(3-aminopropylthio)-1,2,3,4-tetrazole (1 g), colorless liquid, $n_D^{21.5}=1.5384$.

Elemental analysis for $C_5H_{11}N_5S$: Calcd (%): C, 34.67; H, 6.64; N, 40.43. Found (%): C, 34.58; H, 6.36; N, 40.21.

EXAMPLE 132

In the same manner as described in Example 131, the following compound is prepared:

1-Phenyl-5-(3-aminopropylthio)-1,2,3,4-tetrazole, colorless liquid, $n_D^{15.5}=1.5930$

EXAMPLE 133

1-Methyl-5-(3-aminopropylthio)-1,2,3,4-tetrazole (1.7 g) and 1,2-dimethylthiourea hydroiodide (2.3 g) are dissolved in methanol (30 ml) and the mixture is refluxed for 3 hours. After methanol is distilled off, the residue is purified by column chromatography (Basic Alumina, activity grade II, made by Merk & Co.), followed by eluting with chloroform-methanol (9:1) to give 1-methyl-5-[3-(3-methylguanidino)propylthio]-1,2,3,4-tetrazole hydroiodide (0.7 g), colorless liquid, $n_D^{28.5}=1.5684$.

EXAMPLE 134

3-(1-Methyl-1,2,3,4-tetrazol-5-yl)thiopropylamine (1.5 g) is dissolved in ethanol (5 ml), and thereto is added dropwise a solution of methyl isothiocyanate (0.8 g) in ethanol (5 ml) with stirring under ice-cooling, and the mixture is refluxed for 1 hour. Ethanol is distilled off, and then the residue is purified by column chromatography (Kieselgel 60), followed by eluting with chloroform-methanol (50:1) to give 1-[3-(1-methyl-1,2,3,4-tetrazol-5-yl)thiopropyl]-3-methylthiourea (0.7 g) which is recrystallized from ethanol-ligroin, pale yellow granules, m.p. 99°-101° C.

EXAMPLE 135

1-[3-(1-Methyl-1,2,3,4-tetrazol-5-yl)thiopropyl]-3-methylthiourea (8 g) is dissolved in methanol (80 ml). To the mixture is added methyl iodide (5.7 g) and the mixture is refluxed for 5 hours. To the reaction mixture is further added hydrazine hydrate (2.4 g) and the mixture is refluxed for 2 hours. After the solvent is distilled off, the resulting crystalline product is recrystallized from ethanol to give 1-amino-2-methyl-3-[3-(1-methyl-1,2,3,4-tetrazol-5-yl)thiopropyl]guanidine hydroiodide (8.5 g), colorless prisms, m.p. 105°-108° C.

Preparation 1

| Ingredients | Amounts |
|---|---|
| N,N—Diethyl-4-(5-methyl-1,2,3,4-tetrazol-1-yl)butylamide | 150 g |
| Avicel (trade mark of microcrystalline cellulose produced by Asahi-Kasei Co., Ltd.) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

The compound of the present invention, Avicel, corn starch and magnesium stearate are mixed, ground and then, compressed into tablets with a punch having a diameter of 10 mm. The tablets thus obtained are coated with the film coating solution consisting of hydroxypropylmethyl cellulose, polyethylene glycol-6000, castor oil and methanol to obtain film coated tablets.

Preparation 2

| Ingredients | Amounts |
|---|---|
| N—Ethyl-N—cyclohexyl-4-(5-methyl-1,2,3,4-tetrazol-1-yl)butyramide | 150 g |
| Citric acid | 1 g |
| Lactose | 33.5 g |
| Calcium secondary phosphate | 70.0 g |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | appropriate amount |

The compound of the present invention, citric acid, lactose, calcium secondary phosphate, Pluronic F-68 and sodium lauryl sulfate are mixed and passed through No. 60 screen. The resulting mixture is granulated with an alcoholic solution containing polyvinyl pyrrolidone, Carbowax 1500 and Carbowax 6000. The powdery mixture is made into paste by adding alcohol, if necessary. Corn starch is added to the wet mass and mixing is continued until uniform granules are formed. The wet granules are passed through No. 10 screen, placed in a try and dried in an oven at 100° C. for 12-14 hours. The dried granules are passed through No. 16 screen, mixed with dry sodium lauryl sulfate and dry magnesium stearate and then, compressed into a desired shape.

The core tablets thus obtained are treated with varnish and thereto is spreaded talc in order to prevent absorption of moisture. Subcoating is applied about the resulting tablets. The tablets are again treated enough times with varnish for oral administration. Further, subcoating and smooth layers are applied about the tablets so as to make them round and smooth. Coloring layer is applied so as to be the tablets in desired color. After drying, polishing produces the tablets having homogeneous gloss.

Preparation 3

| Ingredients | Amounts |
|---|---|
| N—(4-Methoxyphenyl)-4-(5-methyl-1,2,3,4-tetrazol-1-yl)butyramide | 5 g |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved in an about half amount of the distilled water with stirring at 80° C. The resulting solution is cooled to 40° C. and the above compound of the present invention, polyethylene glycol and polyoxyethylene sorbitan monooleate are dissolved in the solution. The remaining distilled water is added to the solution to adjust the volume. The solution is sterilized by filtration with a suitable filter paper to obtain a preparation for injection.

Preparation 4

| Ingredients | Amounts |
|---|---|
| 1-Methyl-5-(3-benzoylpropyl)thio-1,2,3,4-tetrazole | 150 g |
| Avicel (trade mark of microcrystalline cellulose produced by Asahi-Kasei Co., Ltd.) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

The compound of the present invention, Avicel, corn starch and magnesium stearate are mixed, ground and then, compressed into tablets with a punch having a diameter of 10 mm. The tablets thus obtained are coated with the film coating solution consisting of hydroxypropylmethyl cellulose, polyethylene glycol-6000, castor oil and methanol to obtain film coated tablets.

Preparation 5

| Ingredients | Amounts |
|---|---|
| 1-Methyl-5-(3-cyclohexylcarbonylpropyl-thio-1,2,3,4-tetrazole | 150 g |
| Citric acid | 1 g |
| Lactose | 33.5 g |
| Calcium secondary phosphate | 70.0 g |

-continued

| Ingredients | Amounts |
| --- | --- |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | appropriate amount |

The compound of the present invention, citric acid, lactose, calcium secondary phosphate, Pluronic F-68 and sodium lauryl sulfate are mixed and passed through No. 60 screen. The resulting mixture is granulated with an alcoholic solution containing polyvinyl pyrrolidone, Carbowax 1500 and Carbowax 6000. The powdery mixture is made into paste by adding alcohol, if necessary. Corn starch is added to the wet mass and mixing is continued until uniform granules are formed. The wet granules are passed through No. 10 screen, placed in a try and dried in an oven at 100° C. for 12–14 hours. The dried granules are passed through No. 16 screen, mixed with dry sodium lauryl sulfate and dry magnesium stearate and then, compressed into a desired shape.

The core tablets thus obtained are treated with varnish and thereto is spreaded talc in order to prevent absorption of moisture. Subcoating is applied about the resulting tablets. The tablets are again treated enough times with varnish for oral administration. Further, subcoating and smooth layers are applied about the tablets so as to make them round and smooth. Coloring layer is applied so as to be the tablets in desired color. After drying, polishing produces the tablets having homogeneous gloss.

Preparation 6

| Ingredients | Amounts |
| --- | --- |
| 1-Methyl-5-(3-propionylpropyl)thio-1,2,3,4-tetrazole | 5 g |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved in an about half amount of the distilled water with stirring at 80° C. The resulting solution is cooled to 40° C. and the above compound of the present invention, polyethylene glycol and polyoxyethylene sorbitan monooleate are dissolved in the solution. The remaining distilled water is added to the solution to adjust the volume. The solution is sterilized by filtration with a suitable filter paper to obtain a preparation for injection.

Preparation 7

| Ingredients | Amounts |
| --- | --- |
| 1-Methyl-5-[3-(4-ethylbenzoyl)propyl]thio-1,2,3,4-tetrazole | 150 g |
| Avicel (trade mark of microcrystalline cellulose produced by Asahi-Kasei Co., Ltd.) | 40 g |

-continued

| Ingredients | Amounts |
| --- | --- |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

The compound of the present invention, Avicel, corn starch and magnesium stearate are mixed, ground and then, compressed into tablets with a punch having a diameter of 10 mm. The tablets thus obtained are coated with the film coating solution consisting of hydroxypropylmethyl cellulose, polyethylene glycol-6000, castor oil and methanol to obtain film coated tablets.

Preparation 8

| Ingredients | Amounts |
| --- | --- |
| 1-Methyl-5-[3-(2-thenoyl)propyl]thio-1,2,3,4-tetrazole | 150 g |
| Citric acid | 1 g |
| Lactose | 33.5 g |
| Calcium secondary phosphate | 70.0 g |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | appropriate amount |

The compound of the present invention, citric acid, lactose, calcium secondary phosphate, Pluronic F-68 and sodium lauryl sulfate are mixed and passed through No. 60 screen. The resulting mixture is granulated with an alcoholic solution containing polyvinyl pyrrolidone, Carbowax 1500 and Carbowax 6000. The powdery mixture is made into paste by adding alcohol, if necessary. Corn starch is added to the wet mass and mixing is continued until uniform granules are formed. The wet granules are passed through No. 10 screen, placed in a try and dried in an oven at 100° C. for 12–14 hours. The dried granules are passed through No. 16 screen, mixed with dry sodium lauryl sulfate and dry magnesium stearate and then, compressed into a desired shape.

The core tablets thus obtained are treated with varnish and thereto is spreaded talc in order to prevent absorption of moisture. Subcoating is applied about the resulting tablets. The tablets are again treated enough times with varnish for oral administration. Further, subcoating and smooth layers are applied about the tablets so as to make them round and smooth. Coloring layer is applied so as to be the tablets in desired color. After drying, polishing produces the tablets having homogeneous gloss.

Preparation 9

| Ingredients | Amounts |
| --- | --- |
| 1-Methyl-5-[3-(3,4-dimethoxybenzoyl)propyl]thio-1,2,3,4-tetrazole | 5 g |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |

-continued

| Ingredients | Amounts |
| --- | --- |
| Methyl-paraben | 0.18 g |
| Propyl-paraben | 0.02 g |
| Distilled water for injection | 100 ml |

The above parabens, sodium metabisulfite and sodium chloride are dissolved in an about half amount of the distilled water with stirring at 80° C. The resulting solution is cooled to 40° C. and the above compound of the present invention, polyethylene glycol and polyoxyethylene sorbitan monooleate are dissolved in the solution. The remaining distilled water is added to the solution to adjust the volume. The solution is sterilized by filtration with a suitable filter paper to obtain a preparation for injection.

Preparation 10

| Ingredients | Amounts |
| --- | --- |
| 1-Methyl-5-[3-(N—cyclohexylcarbonylamino-propyl]thio-1,2,3,4-tetrazole | 150 g |
| Avicel (trade mark of microcrystalline cellulose produced by Asahi-Kasei Co., Ltd.) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

The compound of the present invention, Avicel, corn starch and magnesium stearate are mixed, ground and then, compressed into tablets with a punch having a diameter of 10 mm. The tablets thus obtained are coated with the film coating solution consisting of hydroxypropylmethyl cellulose, polyethylene glycol-6000, castor oil and methanol to obtain film coated tablets.

Preparation 11

| Ingredients | Amounts |
| --- | --- |
| 1-Methyl-5-[3-(N—methyl-N—acetylamino)-propyl]thio-1,2,3,4-tetrazole | 150 g |
| Citric acid | 1 g |
| Lactose | 33.5 g |
| Calcium secondary phosphate | 70.0 g |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | appropriate amount |

The compound of the present invention, citric acid, lactose, calcium secondary phosphate, Pluronic F-68 and sodium lauryl sulfate are mixed and passed through No. 60 screen. The resulting mixture is granulated with an alcoholic solution containing polyvinyl pyrrolidone, Carbowax 1500 and Carbowax 6000. The powdery mixture is made into paste by adding alcohol, if necessary. Corn starch is added to the wet mass and mixing is continued until uniform granules are formed. The wet granules are passed through No. 10 screen, placed in a try and dried in an oven at 100° C. for 12–14 hours. The dried granules are passed through No. 16 screen, mixed with dry sodium lauryl sulfate and dry magnesium stearate and then, compressed into a desired shape.

The core tablets thus obtained are treated with varnish and thereto is spreaded talc in order to prevent absorption of moisture. Subcoating is applied about the resulting tablets. The tablets are again treated enough times with varnish for oral administration. Further, subcoating and smooth layers are applied about the tablets so as to make them round and smooth. Coloring layer is applied so as to be the tablets in desired color. After drying, polishing produces the tablets having homogeneous gloss.

Preparation 12

| Ingredients | Amounts |
| --- | --- |
| 1-Phenyl-5-[3-(N—benzoylamino)propyl]-thio-1,2,3,4-tetrazole | 5 g |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved in an about half amount of the distilled water with stirring at 80° C. The resulting solution is cooled to 40° C. and the above compound of the present invention, polyethylene glycol and polyoxyethylene sorbitan monooleate are dissolved in the solution. The remaining distilled water is added to the solution to adjust the volume. The solution is sterilized by filtration with a suitable filter paper to obtain a preparation for injection.

Preparation 13

| Ingredients | Amounts |
| --- | --- |
| 1-Methyl-5-[3-(1-methyl-1,2,3,4-tetrazol-5-yl)thiopropyl]thio-1,2,3,4-tetrazole | 150 g |
| Avicel (trade mark of microcrystalline cellulose produced by Asahi-Kasei Co., Ltd.) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Methanol | 40 g |

The compound of the present invention, Avicel, corn starch and magnesium stearate are mixed, ground and then, compressed into tablets with a punch having a diameter of 10 mm. The tablets thus obtained are coated with the film coating solution consisting of hydroxypropylmethyl cellulose, polyethylene glycol-6000, castor oil and methanol to obtain film coated tablets.

Preparation 14

| Ingredients | Amounts |
| --- | --- |
| 1-Phenyl-5-[4-(1-phenyl-1,2,3,4-tetrazol-5-yl)thiobutyl]thio-1,2,3,4-tetrazole | 150 g |
| Citric acid | 1 g |
| Lactose | 33.5 g |
| Calcium secondary phosphate | 70.0 g |
| Pluronic F-68 | 30.0 g |
| Sodium lauryl sulfate | 15.0 g |

| Ingredients | Amounts |
| --- | --- |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | appropriate amount |

The compound of the present invention, citric acid, lactose, calcium secondary phosphate, Pluronic F-68 and sodium lauryl sulfate are mixed and passed through No. 60 screen. The resulting mixture is granulated with an alcoholic solution containing polyvinyl pyrrolidone, Carbowax 1500 and Carbowax 6000. The powdery mixture is made into paste by adding alcohol, if necessary. Corn starch is added to the wet mass and mixing is continued until uniform granules are formed. The wet granules are passed through No. 10 screen, placed in a try and dried in an oven at 100° C. for 12-14 hours. The dried granules are passed through No. 16 screen, mixed with dry sodium lauryl sulfate and dry magnesium stearate and then, compressed into a desired shape.

The core tablets thus obtained are treated with varnish and thereto is spreaded talc in order to prevent absorption of moisture. Subcoating is applied about the resulting tablets. The tablets are again treated enough times with varnish for oral administration. Further, subcoating and smooth layers are applied about the tablets so as to make them round and smooth. Coloring layer is applied so as to be the tablets in desired color. After drying, polishing produces the tablets having homogeneous gloss.

Preparation 15

| Ingredients | Amounts |
| --- | --- |
| 1-Methyl-5-[3-(2-pyridyl)thiopropyl]-thio-1,2,3,4-tetrazole | 150 g |
| Citric acid | 1 g |
| Lactose | 33.5 g |
| Calcium secondary phosphate | 70.0 g |
| Pluronic F-68 | 30.0 g |
| Sodium lauryl sulfate | 15.0 g |
| Polyvinyl pyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | appropriate amount |

The compound of the present invention, citric acid, lactose, calcium secondary phosphate, Pluronic F-68 and sodium lauryl sulfate are mixed and passed through No. 60 screen. The resulting mixture is granulated with an alcoholic solution containing polyvinyl pyrrolidone, Carbowax 1500 and Carbowax 6000. The powdery mixture is made into paste by adding alcohol, if necessary. Corn starch is added to the wet mass and mixing is continued until uniform granules are formed. The wet granules are passed through No. 10 screen, placed in a try and dried in an oven at 100° C. for 12-14 hours. The dried granules are passed through No. 16 screen, mixed with dry sodium lauryl sulfate and dry magnesium stearate and then, compressed into a desired shape.

The core tablets thus obtained are treated with varnish and thereto is spreaded talc in order to prevent absorption of moisture. Subcoating is applied about the resulting tablets. The tablets are again treated enough times with varnish for oral administration. Further, subcoating and smooth layers are applied about the tablets so as to make them round and smooth. Coloring layer is applied so as to be the tablets in desired color. After drying, polishing produces the tablets having homogeneous gloss.

Preparation 16

| Ingredients | Amounts |
| --- | --- |
| 1-Methyl-1,2,3,4-tetrazol-5-yl 4-(1-methyl-1,2,3,4-tetrazol-5-yl)thiobutyl sulfoxide | 5 g |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved in an about half amount of the distilled water with stirring at 80° C. The resulting solution is cooled to 40° C. and the above compound of the present invention, polyethylene glycol and polyoxyethylene sorbitan monooleate are dissolved in the solution. The remaining distilled water is added to the solution to adjust the volume. The solution is sterilized by filtration with a suitable filter paper to obtain a preparation for injection.

Preparation 17

| Ingredients | Amounts |
| --- | --- |
| 1-Methyl-5-[3-phenylthiopropyl]thio-1,2,3,4-tetrazole | 5 g |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved in an about half amount of the distilled water with stirring at 80° C. The resulting solution is cooled to 40° C. and the above compound of the present invention, polyethylene glycol and polyoxyethylene sorbitan monooleate are dissolved in the solution. The remaining distilled water is added to the solution to adjust the volume. The solution is sterilized by filtration with a suitable filter paper to obtain a preparation for injection.

What is claimed is:

1. A tetrazole derivative of the formula:

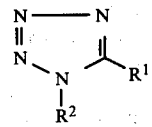

wherein $R^1$ is a lower alkyl, phenyl or a group of the formula: $-S(O)_l-A-(X)_m-R^3$, and $R^2$ is hydrogen, a lower alkyl, phenyl or a cycloalkyl when $R^1$ is the group —S(O)$_l$—A—(X)$_m$—R$^3$, or R$^2$ is a group of the formula: —B—CO—R$^4$ when R$^1$ is a lower alkyl or phenyl; in said formula —S—(O)$_l$—A—(X)$_m$—R$^3$, X is —CO— or S—(O)$_n$—, l and n are each 0, 1 or 2, m is 0 or 1, A is an alkylene having 1 to 8 carbon atoms, and R$^3$ is a lower alkyl, a cycloalkyl, naphthyl, a group of the formula:

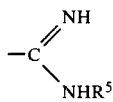

(R$^5$ is a lower alkyl), a phenyl(lower)alkyl which may have a halogen substituent on the phenyl ring, a pheny which may have 1 to 3 substituents selected from the group consisting of a halogen, a lower alkyl, a lower alkoxy, a lower alkanoylamino, hydroxy, carboxy and amino, a heterocyclic group-substituted lower alkyl which may have a substituent selected from a lower alkyl and amino wherein the heterocyclic group is selected from pyridyl, furyl, and thiazolyl, or a heterocyclic group containing 1 to 4 hetero atoms selected from nitrogen, oxygen and sulfur which may have 1 to 2 substituents selected from the group consisting of a lower alkyl, a halogen, carboxy, oxo, amino, a lower alkoxycarbonyl, a lower alkoxy, hydroxy, nitro, phenyl, a cycloalkyl and a lower alkylamino, wherein the heterocyclic group containing 1 to 4 hetero atoms is selected from thienyl, furyl, pyrrolyl, pyridyl, pyranyl, pyrimidyl, quinolyl, 1,2,3,4-tetrahydroquinolyl, imidazolyl, 1,3,4-thiadiazolyl, 1,3,4-oxadiazolyl, 1H-1,2,4-triazolyl, 4H-1,2,4-triazolyl, thiazolyl, 1,2,3,4-tetrazolyl, benzimidazolyl, quinazolyl, 2,4-dihydroquinazolyl, and 3H,4H-1,3,4-benzotriazepinyl, and when m is 0, R$^3$ may also be a group of the formula: —NR$^6$R$^7$ wherein R$^6$ is hydrogen, a lower alkyl or a phenyl (lower)alkyl, and R$^7$ is hydrogen, a lower alkyl, a group —CZ—NHR$^8$ (Z is sulfur or an imino which may be substituted with a lower alkyl, and R$^8$ is a lower alkyl or imino), a tetrazolyl which may have a lower alkyl substituent, or a group —CO—R$^9$, wherein R$^9$ is a lower alkyl, a phenyl which may have 1 to 3 lower alkoxy substituents, a cycloalkyl or a 5- or 6-membered unsaturated heterocyclic group containing one hetero atom selected from nitrogen and oxygen, which group is pyridyl, pyranyl, pyrrolyl or furyl, or the R$^6$ and R$^7$ may combine together with the nitrogen atom to which they are joined to form a group

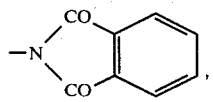

in said formula —B—CO—R$^4$, B is a lower alkylene, and R$^4$ is a group of the formula: —NR$^{10}$R$^{11}$ wherein R$^{10}$ and R$^{11}$ are the same or different and are each a lower alkyl (which may have a substituent selected from the group consisting of hydroxy, furyl, pyridyl, phenyl and a phenyl having 1 to 2 lower alkoxy substituents), a cycloalkyl (which may have a substituent selected from the group consisting of hydroxy or a lower alkoxy), a phenyl (which may have 1 to 2 substituents selected from the group consisting of a lower alkyl, a lower alkoxy, a halogen, nitro, carboxy and a lower alkylamino), or a thiazolyl, or the R$^{10}$ and R$^{11}$ may combine together with the nitrogen atoms to which they are joined with or without being intervened with nitrogen or oxygen to form a 5- or 6-membered saturated heterocyclic group selected from pyrrolidino, morpholino, 1-piperidyl and 1-piperazinyl which may have a lower alkyl substituent, provided that when m is 0, R$^3$ is not substituted phenyl(lower)alkyl or unsubstituted phenyl, and provided that when B is methylene or dimethylmethylene (—C(CH$_3$)$_2$—), R$^4$ excludes di-(lower)alkylamino and 1-piperidyl, or a pharmaceutically acceptable salt thereof.

2. A compound according to claim 1, wherein R$^1$ is as defined herein and R$^2$ is —B—CO—R$^4$ wherein B and R$^4$ are as defined herein.

3. A compound according to claim 2, wherein R$^4$ is a group of the formula

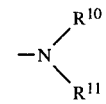

wherein R$^{10}$ and R$^{11}$ are as defined herein.

4. A compound according to claim 2, wherein R$^4$ is hydroxy or a lower alkoxy.

5. A compound according to claim 3, wherein R$^{10}$ and R$^{11}$ are each a member selected from the group consisting of a lower alkyl (which has a substituent selected from hydroxy, furyl, pyridyl or a phenyl which has 1 to 2 lower alkoxy substituents), a cycloalkyl (which has a substituent selected from hydroxy and a lower alkoxy), a phenyl (which may have 1 to 2 substituents selected from a lower alkyl, a lower alkoxy, a halogen, nitro, carboxy and a lower alkylamino) and a thiazolyl, or R$^{10}$ and R$^{11}$ combine together with the nitrogen atom to which they are joined with or without being intervened with nitrogen or sulfur to form a 5- or 6-membered saturated heterocyclic group selected from pyrrolidino, morpholino and 1-piperazinyl which may have a lower alkyl substituent.

6. A compound according to claim 1, wherein R$^1$ is —S(O)$_l$—A—(X)$_m$—R$^3$ wherein A, R$^3$, X, l and m are as defined herein, R$^2$ is as defined herein.

7. A compound according to claim 6, wherein m is 1.

8. A compound according to claim 6, wherein m is 0.

9. A compound according to claim 7, wherein X is —CO—.

10. A compound according to claim 7, wherein X is —S(O)$_n$— wherein n is as defined herein.

11. A compound according to claim 8, wherein R$^3$ is

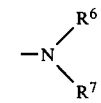

wherein R$^6$ and R$^7$ are as defined herein.

12. A compound according to claim 8, wherein R$^3$ is a member selected from the group consisting of a lower alkyl, a cycloalkyl, naphthyl, a group of the formula

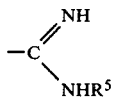

wherein R⁵ is as defined herein, a phenyl(lower)alkyl which may have a halogen substituent on the phenyl ring, a phenyl (which may have 1 to 3 substituents selected from a halogen, a lower alkyl, a lower alkoxy, a lower alkanoylamino, hydroxy, carboxy and amino), a heterocyclic group-substituted lower alkyl (which may have a substituent selected from a lower alkyl and amino) wherein the heterocyclic group is selected from pyridyl, furyl and thiazolyl, and a heterocyclic group containing 1 to 4 hetero atoms selected from nitrogen, oxygen and sulfur wherein the heterocyclic group containing 1 to 4 hetero atoms is selected from thienyl, furyl, pyrrolyl, pyridyl, pyranyl, pyrimidyl, quinolyl, 1,2,3,4-tetrahydroquinolyl, imidazolyl, 1,3,4-thiadiazolyl, 1,3,4-oxadiazolyl, 1H-1,2,4-triazolyl, 4H-1,2,4-triazolyl, thiazolyl, 1,2,3,4-tetrazolyl, benzimidazolyl, quinazolyl, 2,4-dihydroquinazolyl, and 3H,4H-1,3,4-benzotriazepinyl, (which may have 1 to 2 substituents selected from a lower alkyl, a halogen, carboxy, oxo, amino, a lower alkoxycarbonyl, a lower alkoxy, hydroxy, nitro, phenyl, a cycloalkyl and a lower alkylamino).

13. A compound according to claim 9, wherein R² is a lower alkyl, phenyl or a cycloalkyl and R³ is a cycloalkyl, naphthyl, or a phenyl which may have 1 to 3 substituents selected from the group consisting of a halogen, a lower alkyl, a lower alkoxy, a lower alkanoylamino, hydroxy, carboxy, and amino.

14. A compound according to claim 9, wherein R³ is a member selected from the group consisting of a lower alkyl, a group of the formula:

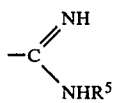

wherein R⁵ is as defined herein, a phenyl(lower)alkyl which may have a halogen substituent on the phenyl ring, a heterocyclic group-substituted lower alkyl (which may have a substituent selected from a lower alkyl and amino) wherein the heterocyclic group is selected from pyridyl, furyl and thiazolyl, and a heterocyclic group containing 1 to 4 hetero atoms selected from nitrogen, oxygen and sulfur which is selected from thienyl, furyl, pyrrolyl, pyridyl, pyranyl, pyrimidyl, quinolyl, 1,2,3,4-tetrahydroquinolyl, imidazolyl, 1,3,4-thiadiazolyl, 1,3,4-oxadiazolyl, 1H-1,2,4-triazolyl, 4H-1,2,4-triazolyl, thiazolyl, 1,2,3,4-tetrazolyl, benzimidazolyl, quinazolyl, 2,4-dihydroquinazolyl, and 3H,4H-1,3,4-benzotriazepinyl (which may have 1 to 2 substituents selected from a lower alkyl, a halogen, carboxy, oxo, amino, a lower alkoxycarbonyl, a lower alkoxy, hydroxy, nitro, phenyl, a cycloalkyl and a lower alkylamino).

15. 1-phenyl-5-(3-cyclohexylcarbonylpropyl)-thio-1,2,3,4-tetrazole.

16. 1-methyl-5-(2-benzoylethyl)thio-1,2,3,4-tetrazole.

17. N,N-diethyl-4-(5-methyl-1,2,3,4-tetrazol-1-yl)butyramide.

18. N,N-dipropyl-4-(5-methyl-1,2,3,4-tetrazol-1-yl)butyramide.

19. N,N-diethyl-5-(5-methyl-1,2,3,4-tetrazol-1-yl)valeramide.

20. N,N-diethyl-4-(5-phenyl-1,2,3,4-tetrazol-1-yl)butyramide.

21. 1-methyl-5-acetylmethylthio-1,2,3,4-tetrazole.

22. 1-methyl-5-[3-(2-pyridyl)carbonylpropyl]thio-1,2,3,4-tetrazole.

23. 1-methyl-5-[3-(2-amino-4-thiazolyl)methylthiopropyl]thio-1,2,3,4-tetrazole.

24. An anti-ulcer composition, which comprises as active ingredient an effective amount of a tetrazole derivative of the formula:

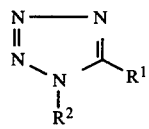 (1)

wherein R¹ is a lower alkyl, phenyl or a group of the formula: —S(O)$_l$—A—(X)$_m$—R³, and R² is hydrogen, a lower alkyl, phenyl or a cycloalkyl when R¹ is the group —S(O)$_l$—A—(X)$_m$—R³, or R² is a group of the formula: —B—CO—R⁴ when R¹ is a lower alkyl or phenyl; in said formula —S(O)$_l$—A—(X)$_m$—R³, X is —CO— or S—(O)$_n$—, l and n are each 0, 1 or 2, m is 0 or 1, A is an alkylene having 1 to 8 carbon atoms, and R³ is a lower alkyl, a cycloalkyl, naphthyl, a group of the formula:

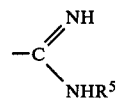

(R⁵ is a lower alkyl), a phenyl(lower)alkyl which may have a halogen substituent on the phenyl ring, a phenyl which may have 1 to 3 substituents selected from the group consisting of a halogen, a lower alkyl, a lower alkoxy, a lower alkanoylamino, hydroxy, carboxy and amino, a heterocyclic group-substituted lower alkyl which may have a substituent selected from a lower alkyl and amino wherein the heterocyclic group is selected from pyridyl, furyl and thiazolyl, or a heterocyclic group containing 1 to 4 hetero atoms selected from nitrogen, oxygen and sulfur which may have 1 to 2 substituents selected from the group consisting of a lower alkyl, a halogen, carboxy, oxo, amino, a lower alkoxycarbonyl, a lower alkoxy, hydroxy, nitro, phenyl, a cycloalkyl and a lower alkylamino, wherein the heterocyclic group containing 1 to 4 hetero atoms is selected from thienyl, furyl, pyrrolyl, pyridyl, pyranyl, pyrimidyl, quinolyl, 1,2,3,4-tetrahydroquinolyl, imidazolyl, 1,3,4-thiadiazolyl, 1,3,4-oxadiazolyl, 1H-1,2,4-triazolyl, 4H-1,2,4-triazolyl, thiazolyl, 1,2,3,4-tetrazolyl, benzimidazolyl, quinazolyl, 2,4-dihydroquinazolyl, and 3H,4H-1,3,4-benzotriazepinyl, and when m is 0, R³ may also be a group of the formula: —NR⁶R⁷ wherein R⁶ is hydrogen, a lower alkyl or a phenyl(lower)alkyl, and R⁷ is hydrogen, a lower alkyl, a group —CZ—NHR⁸ (Z is sulfur or an imino which may be substituted with a lower alkyl, and R⁸ is a lower alkyl or amino, a tetrazolyl which may have a lower alkyl substituent, or a group —CO—R⁹, wherein R⁹ is a lower alkyl, a phenyl which may have 1 to 3 lower alkoxy substituents, a cycloalkyl or a 5- or 6-membered unsaturated heterocyclic group containing one hetero atom selected from nitrogen and oxygen, said group being pyrrolidino, morpholino, 1-piperidinyl or 1-piperazinyl, or the R⁶ and R⁷ may combine together with the nitrogen atom to which they are joined to form a group

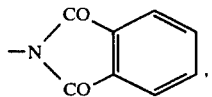

in said formula —B—CO—$R^4$, B is a lower alkylene, and $R^4$ is a group of the formula: —$NR^{10}R^{11}$ wherein $R^{10}$ and $R^{11}$ are the same or different and are each a lower alkyl (which may have a substituent selected from the group consisting of hydroxy, furyl, pyridyl, phenyl and a phenyl having 1 to 2 lower alkoxy substituents), a cycloalkyl (which may have a substituent selected from the group consisting of hydroxy or a lower alkoxy), a phenyl (which may have 1 to 2 substituents selected from the group consisting of a lower alkyl, a lower alkoxy, a halogen, nitro, carboxy and a lower alkylamino), or a thiazolyl, or the $R^{10}$ and $R^{11}$ may combine together with the nitrogen atom to which they are joined with or without being intervened with nitrogen or oxygen to form a 5- or 6-membered saturated heterocyclic group which may have a lower alkyl substituent, provided that when m is 0, $R^3$ is not unsubstituted phenyl(lower)alkyl or unsubstituted phenyl, and provided that when B is methylene or dimethylmethylene (—C(CH$_3$)$_2$—), $R^4$ excludes di-(lower)alkylamino and 1-piperidyl, or a pharmaceutically acceptable salt thereof in admixture with a carrier or diluent.

* * * * *